US011154597B2

(12) United States Patent
Niazi et al.

(10) Patent No.: US 11,154,597 B2
(45) Date of Patent: Oct. 26, 2021

(54) SEQUENCE ARRANGEMENTS AND SEQUENCES FOR NEOEPITOPE PRESENTATION

(71) Applicants: NANTCELL, INC., Culver City, CA (US); NANT HOLDINGS IP, LLC, Culver City, CA (US); NANTOMICS, LLC, Culver City, CA (US)

(72) Inventors: Kayvan Niazi, Agoura Hills, CA (US); Andrew Nguyen, San Jose, CA (US); Shahrooz Rabizadeh, Los Angeles, CA (US); Patrick Soon-Shiong, Los Angeles, CA (US); Stephen Charles Benz, Santa Cruz, CA (US)

(73) Assignees: NantCell, Inc., Culver City, CA (US); Nant Holdings IP, LLC, Culver City, CA (US); NantOmics, LLC, Culver City, CA (US)

( * ) Notice: Subject to any disclaimer, the term of this patent is extended or adjusted under 35 U.S.C. 154(b) by 0 days.

(21) Appl. No.: 15/468,046

(22) Filed: Mar. 23, 2017

(65) Prior Publication Data

US 2017/0312351 A1    Nov. 2, 2017

Related U.S. Application Data

(60) Provisional application No. 62/314,366, filed on Mar. 28, 2016, provisional application No. 62/313,621, filed on Mar. 25, 2016, provisional application No. 62/312,974, filed on Mar. 24, 2016.

(51) Int. Cl.

| A61K 39/00 | (2006.01) |
| A61K 39/39 | (2006.01) |
| C07K 7/06 | (2006.01) |
| C07K 14/74 | (2006.01) |
| C07K 14/705 | (2006.01) |
| C12N 7/00 | (2006.01) |
| C12N 15/86 | (2006.01) |
| G16B 20/00 | (2019.01) |
| G16B 20/20 | (2019.01) |

(52) U.S. Cl.
CPC .......... *A61K 39/0011* (2013.01); *A61K 39/39* (2013.01); *C07K 7/06* (2013.01); *C07K 14/70539* (2013.01); *C07K 14/70596* (2013.01); *C12N 7/00* (2013.01); *C12N 15/86* (2013.01); *A61K 2039/5254* (2013.01); *A61K 2039/5256* (2013.01); *A61K 2039/57* (2013.01); *A61K 2039/572* (2013.01); *A61K 2039/70* (2013.01); *C07K 2319/01* (2013.01); *C07K 2319/06* (2013.01); *C07K 2319/40* (2013.01); *C07K 2319/95* (2013.01); *C12N 2710/10321* (2013.01); *C12N 2710/10334* (2013.01); *C12N 2710/10343* (2013.01); *C12N 2840/002* (2013.01); *G16B 20/00* (2019.02); *G16B 20/20* (2019.02)

(58) Field of Classification Search
None
See application file for complete search history.

(56) References Cited

U.S. PATENT DOCUMENTS

| 7,179,797 | B2 | 2/2007 | McNeel |
| 7,473,532 | B2 | 1/2009 | Darfler et al. |
| 7,758,891 | B2 | 7/2010 | Desai et al. |
| 7,771,751 | B2 | 8/2010 | Desai et al. |
| 7,780,984 | B2 | 8/2010 | Desai et al. |
| 7,981,445 | B2 | 7/2011 | De et al. |
| 8,034,375 | B2 | 10/2011 | Desai et al. |
| 8,445,268 | B2 | 5/2013 | Lee et al. |
| 2005/0095648 | A1 | 5/2005 | Geysen et al. |
| 2007/0123487 | A1 | 5/2007 | McNeel |
| 2010/0196411 | A1 | 8/2010 | Duke et al. |
| 2011/0071214 | A1 | 3/2011 | Allen |
| 2011/0293637 | A1* | 12/2011 | Hacohen ............. C12Q 1/6886 424/173.1 |
| 2012/0059670 | A1 | 3/2012 | Sanborn et al. |
| 2012/0066001 | A1 | 3/2012 | Sanborn et al. |
| 2012/0107347 | A1 | 5/2012 | Hodge et al. |
| 2014/0178438 | A1 | 6/2014 | Sahin et al. |
| 2014/0363465 | A1 | 12/2014 | Letvin et al. |
| 2016/0339090 | A1* | 11/2016 | Hacohen ............ A61K 39/0011 |
| 2017/0224794 | A1 | 8/2017 | Franzusoff et al. |
| 2017/0246276 | A1 | 8/2017 | Palena et al. |
| 2020/0054730 | A1 | 2/2020 | Niazi |

FOREIGN PATENT DOCUMENTS

| CA | 3 018 741 | A1 | 12/2017 |
| CN | 109563521 | A | 4/2019 |
| CN | 110662841 | A | 1/2020 |
| JP | 2016-501870 | A | 1/2016 |

(Continued)

OTHER PUBLICATIONS

Charoentong et al. Cancer Immunol. Immunother. 61:1885-1903 (Year: 2012).*
Brennick et al Immunotherapy, 9, 361-371 (Year: 2017).*
McCluskie Mol. Med. 5:287-300 (Year: 1999).*
Scheerlinck et al Vaccine. 21;19(17-19):2647-56 (Year: 2001).*
Niazi et al Immunology, 122, 522-531 (Year: 2007).*
Kreiter et al The Journal of Immunology, 180: 309-318 (Year: 2008).*
Kim et al Molecular Therapy 16 No. 3, 599-606 (Year: 2008).*

(Continued)

*Primary Examiner* — Lori A. Clow
(74) *Attorney, Agent, or Firm* — Martin Fessenmaier; Umberg Zipser LLP

(57) ABSTRACT

Systems and methods are presented that allow for selection of tumor neoepitopes that are then used to generate a recombinant polytope that is optimized for proper trafficking and processing. In preferred methods, the polytope is encoded in a viral expression system that is used as a therapeutic agent.

4 Claims, 8 Drawing Sheets

Specification includes a Sequence Listing.

(56) References Cited

FOREIGN PATENT DOCUMENTS

| JP | 2019-513021 A | 5/2019 |
|---|---|---|
| KR | 10-2016-0101073 A | 8/2016 |
| KR | 20180117227 A | 10/2018 |
| KR | 10-2019-0137165 A | 12/2019 |
| TW | 201742923 A | 12/2017 |
| WO | 00/78806 A1 | 12/2000 |
| WO | 2009/006479 A3 | 3/2009 |
| WO | 2011/139345 A2 | 11/2011 |
| WO | 2012/159754 A2 | 11/2012 |
| WO | 2013/062505 A1 | 5/2013 |
| WO | 2014/031178 A1 | 2/2014 |
| WO | 2014/082729 A1 | 6/2014 |
| WO | 2014/168874 A2 | 10/2014 |
| WO | 2015095811 A2 | 6/2015 |
| WO | WO 2016/061087 * | 4/2016 |
| WO | 2016/172722 A1 | 10/2016 |
| WO | 2016/187508 A2 | 10/2016 |
| WO | 2016/191545 A1 | 12/2016 |
| WO | 2016/207859 A1 | 12/2016 |
| WO | 2017/035392 A1 | 3/2017 |
| WO | 2017/066256 A2 | 4/2017 |
| WO | 2017/222619 A2 | 12/2017 |
| WO | 2018/094309 A2 | 5/2018 |
| WO | 2018/100389 A1 | 11/2018 |
| WO | 2018/200389 A1 | 11/2018 |
| WO | 2017/222619 A3 | 3/2019 |

OTHER PUBLICATIONS

Li et al., "Mapping short DNA sequencing reads and calling variants using mapping quality scores", Genome Research, 2008, vol. 18, No. 11, pp. 1851-1858 (Cited from Specification).

Goya et al., SNVMix: predicting single nucleotide variants from next-generation sequencing of tumors, Bioinformatics, 2010, vol. 26, No. 6, pp. 730-736 (Cited from Specification).

Sykulev et al., "Evidence that a Single Peptide-MHC Complex on a Target Cell Can Elicit a Cytolytic T Cell Response", Immunity, Jun. 1, 1996, vol. 4, No. 6, pp. 565-571 (Cited from Specification).

Lawrence et al., "Discovery and saturation analysis of cancer genes across 21 tumour types", Nature, Jan. 23, 2014, vol. 505, No. 7484, pp. 495-501 (Cited from Specification).

Reimand et al., "Systematic analysis of somatic mutations in phosphorylation signaling predicts novel cancer drivers", Molecular Systems Biology, 2013, vol. 9, No. 637, p. 1-18 (Cited from Specification).

Dees et al., "MuSiC: Identifying mutational significance in cancer genomes", Genome Research, Jul. 3, 2012, vol. 22, No. 8, pp. 1589-1598 (Cited from Specification).

Tamborero et al., "OncodriveCLUST: exploiting the positional clustering of somatic mutations to identify cancer genes", Bioinformatics, 2013, vol. 29, No. 18, pp. 2238-2244 (Cited from Specification).

Gonzalez-Perez et al., "Functional impact bias reveals cancer drivers", Nucleic Acids Research, Aug. 16, 2012, vol. 40, No. 21, p. 1-10 (Cited from Specification).

Mularoni et al., "OncodriveFML: a general framework to identify coding and non-coding regions with cancer driver mutations", Genome Biology, 2016, vol. 17, No. 1, p. 1-13 (Cited from Specification).

Davoli et al., "Cumulative Haploinsufficiency and Triplosensitivity Drive Aneuploidy Patterns and Shape the Cancer Genome", Cell, Nov. 7, 2013, vol. 155, No. 4, pp. 948-962 (Cited from Specification).

Schroeder et al., "OncodriveROLE classifies cancer driver genes in loss of function and activating mode of action", Bioinformatics, 2014, vol. 30, No. 17, pp. i549-i555 (Cited from Specification).

Lundegaard et al., "NetMHC-3.0: accurate web accessible predictions of human, mouse and monkey MHC class I affinities for peptides of length 8-11", Nucleic Acids Research, May 7, 2008, vol. 36, Web Server issue, pp. W509-W512 (Cited from Specification).

Zhang et al., "Machine learning competition in immunology—Prediction of HLA class I binding peptides", Journal of Immunological Methods, 2011, vol. 374, No. (1-2), p. 1-4 (Cited from Specification).

Amalfitano et al., "Production and Characterization of Improved Adenovirus Vectors with the E1, E2b, and E3 Genes Deleted", Journal of Virology, Feb. 1998, vol. 72, No. 2, pp. 926-933 (Cited from Specification).

Heijne G.V, "A new method for predicting signal sequence cleavage sites", Nucleic Acids Research, Jun. 11, 1986, vol. 14, No. 11, pp. 4683-4690 (Cited from Specification).

Kall et al., "A Combined Transmembrane Topology and Signal Peptide Prediction Method", Journal of Molecular Biology, 2004, vol. 338, No. 5, pp. 1027-1036(Cited from Specification).

Kouchakzadeh et al., "Efficient Delivery of Therapeutic Agents by Using Targeted Albumin Nanoparticles", Advances in Protein Chemistry and Structural Biology, 2015, vol. 98, 23 pages (Cited from Specification).

First Office Action received for Japanese Patent Application Serial No. 2018-550347 dated Jan. 21, 2020, 07 pages (Including English Translation).

First Office Action received for Korean Patent Application Serial No. 10-2018-7030362 dated Aug. 30, 2019, 11 pages (Including English Translation).

Briken et al., "Intracellular trafficking pathway of newly synthesized CD1b molecules", The EMBO Journal, 2002, vol. 21, No. 4, pp. 825-834.

International Search Report and Written Opinion received for PCT Application Serial No. PCT/US2017/023894 dated Feb. 18, 2019, 13 pages.

Fukuda et al., "Cloning of cDNAs Encoding Human Lysosomal Membrane Glycoproteins, h-lamp-1 and h-lamp-2", The Journal of Biological Chemistry, Dec. 15, 1988, vol. 263, No. 35, pp. 18920-18928.

Fritsch et al., "HLA-binding properties of tumor neoepitopes in humans", Cancer Immunology Research, Jun. 2014, vol. 2, No. 6, pp. 522-529.

Zhang et al., "An adenoviral vector cancer vaccine that delivers a tumor-associated antigen/CD40-ligand fusion protein to dendritic cells", PNAS, Dec. 9, 2003, vol. 1 00, No. 25, p. 1-25.

Sloan et al., "MHC class I and class II presentation of tumor antigen in retrovirally and adenovirally transduced dendritic cells", Cancer Gene Therapy, 2002, vol. 9, No. 11, pp. 946-950.

International Preliminary Report on Patentability received for PCT Application Serial No. PCT/US2017/023894 dated Feb. 26, 2019, 08 pages.

International Search Report and Written Opinion received for Singapore Patent Application Serial No. 11201807770R dated Jan. 22, 2020, 13 pages.

Mateo et al., "An HLA-A2 polyepitope vaccine for melanoma immunotherapy", The Journal of Immunology, Oct. 1, 1999, vol. 163, No. 7, pp. 4058-4063.

Cong et al., "Cytoskeletal protein PSTPIP1 directs the PEST-type protein tyrosine phosphatase to the c-Abl kinase to mediate Abl dephosphorylation", Molecular Cell, Dec. 2000, vol. 6, pp. 1413-1423.

First Examiner's Report received for Canadian Patent Application Serial No. 3018741 dated Oct. 17, 2019, 4 pages.

Partial European Search Report received for European Patent Application Serial No. 17815840.8 dated Mar. 2, 2020, 16 pages.

Notice of Grounds for Rejection received for Korean Patent Application Serial No. 1020187030362 dated Feb. 27, 2020, 14 pages (Including English Translation).

Boyer et al., "Vaccination of Seronegative Volunteers with a Human Immunodeficiency Virus Type 1 env/rev DNA Vaccine Induces Antigen-Specific Proliferation and Lymphocyte Production of β-Chemokines", The Journal of Infectious Diseases, Feb. 2000, vol. 181, pp. 476-483.

Fejer et al., "Adenovirus-Triggered Innate Signalling Pathways", European Journal of Microbiology and Immunology, 2011, vol. 1, No. 4, pp. 279-288.

International Search Report and Written Opinion received for PCT Application Serial No. PCT/US2018028889 dated Aug. 14, 2018, 22 pages.

(56) References Cited

OTHER PUBLICATIONS

Mincheff et al., "Naked DNA and Adenoviral Immunizations for Immunotherapy of Prostate Cancer: A Phase I/II Clinical Trial", European Urology, 2000, vol. 38, 2 pages.
International Preliminary Report received in PCT Application Serial No. PCT/US2018/028889, dated Aug. 28, 2019, 9 pages.
Jones et al., "A Subset of Latency-Reversing Agents Expose HIV-Infected Resting CD4+ T-Cells to Recognition by Cytotoxic T-Lymphocytes", PLOS Pathogens, 2016, vol. 12, No. 4, e1005545, pp. 1-25.
Mincheff et al., "Naked DNA and Adenoviral Immunizations for Immunotherapy of Prostate Cancer: A Phase I/II Clinical Trial", European Urology, 2000, vol. 38, pp. 208-217.
Chu et al., "Indigenous enteric eosinophils control DCs to initiate a primary Th2 immune response in vivo" The Journal of Experimental Medicine 2014, vol. 211, pp. 1657-1672.
Kouchakzadeh Hasan et al., "Efficient Delivery of Therapeutic Agents by Using Targeted Albumin Nanoparticles", Elsevier Inc, 2015, vol. 98, pp. 121-143.
Feltquate et al., "Different T helper cell types and antibody isotypes generated by saline and gene gun DNA immunization", The journal of Immunology, 1997, vol. 158, No. 5, pp. 2278-2284.
Office Action received for Taiwanese Patent Application Serial No. 106110045 dated Jan. 4, 2021, 4 pages (Including English Translation).
Extended European search report received for European Patent Application Serial No. 17815840.8 dated Jun. 25, 2020, 14 pages.
Communication pursuant to Rules 70(2) and 70a(2) EPC received for European Patent Application Serial No. 17815840.8 dated Jul. 14, 2020, 1 page.
Decision of Refusal received for Japanese Patent Application Serial No. 2018550347 dated Aug. 25, 2020, 2 pages (Including English Translation).
Notice of Final Rejection received for Korean Patent Application Serial No. 10-2018-7030362 dated Jul. 6, 2020, 2 pages (Including English Translation).
Office Action received for Taiwanese Patent Application Serial No. 106110045 dated Sep. 14, 2020, 16 pages (Including English Translation).
Non Final Office Action received for U.S. Appl. No. 16/874,104 dated Dec. 2, 2020, 116 pages.
Sorber (NIH Medical Research Scholars Program, 2014-2015 Scholars and Abstracts, pp. 1-48 Abstract p. 39). (Year: 2014).
Xu et al., "Efficacy and mechanism-of-action of a novel superagonist interleukin-15: interieukin-15 receptor αSu/Fc fusion complex in syngeneic murine models of multiple myeloma", Cancer Research, 2013, vol. 73, No. 10, pp. 3075-3086.
Amalfitano et al., "Production and characterization of improved adenovirus vectors with the E1, E2b, and E3 genes deleted", Journal of Virology, 1998, vol. 72, No. 2, pp. 926-933.
Habib-Agahi., "Co-stimulation with 4-1BB ligand allows extended T-cell proliferation, synergizes with CD80/CD86 and can reactivate anergic T cells", International Immunology, 2007, vol. 19, No. 2, pp. 1383-1394.
Andarini et al., "Adenovirus vector-mediated in vivo gene transfer of OX40 ligand to tumor cells enhances antitumor immunity of tumor-bearing hosts", Cancer Research, 2004, vol. 64, 3281-3287.
Hodi et al., "Improved survival with ipilimumab in patients with metastatic melanoma", The New England Journal of Medicine, 2010, vol. 363, No. 8, pp. 711-723.
Office Action received for Canadian patent Application Serial No. 3061240 dated Dec. 9, 2020, 6 pages.
Notification of Reason for Refusal received for Korean Patent Application Serial No. 10-2019-7034742 dated Jan. 5, 2021, 13 pages (Including English Translation).
Notice of acceptance received for Australian Patent Application Serial No. 2018258119 dated Mar. 18, 2021, 3 pages.
Noting of loss of rights pursuant to Rule 112(1) EPC received for European Patent Application Serial No. 17815840.8 dated Feb. 18, 2021, 2 pages.
Notice of Reasons for Refusal received for Japanese Patent Application Serial No. 2019557605 dated Feb. 2, 2021, 7 pages (Including English Translation).
Examination Report No. 1 received for Australian Patent Application Serial No. 2018258119 dated Mar. 1, 2021, 4 pages.
Notice of Final Rejection received for Korean Patent Application Serial No. 10-2019-7034742 dated Jul. 8, 2021, 8 pages (Including English Translation).
Final Office Action received for U.S. Appl. No. 16/874,104 dated Apr. 4, 2021, 109 pages.
Extended European search report received for European Patent Application Serial No. 18791753.9 dated Jan. 28, 2021, 11 pages.
Non Final Office Action received for U.S. Appl. No. 16/874,104 dated Aug. 19, 2021, 51 pages.
Grant of Patent received for Korean Patent Application Serial No. KR10-2019-7034742 dated Sep. 7, 2021, 2 pages (Including English Translation).

* cited by examiner

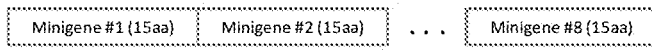
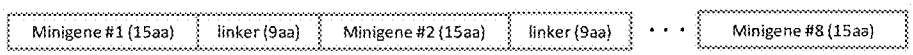
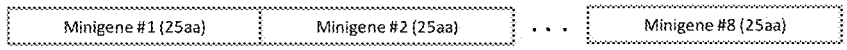
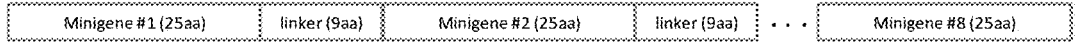
Figure 1
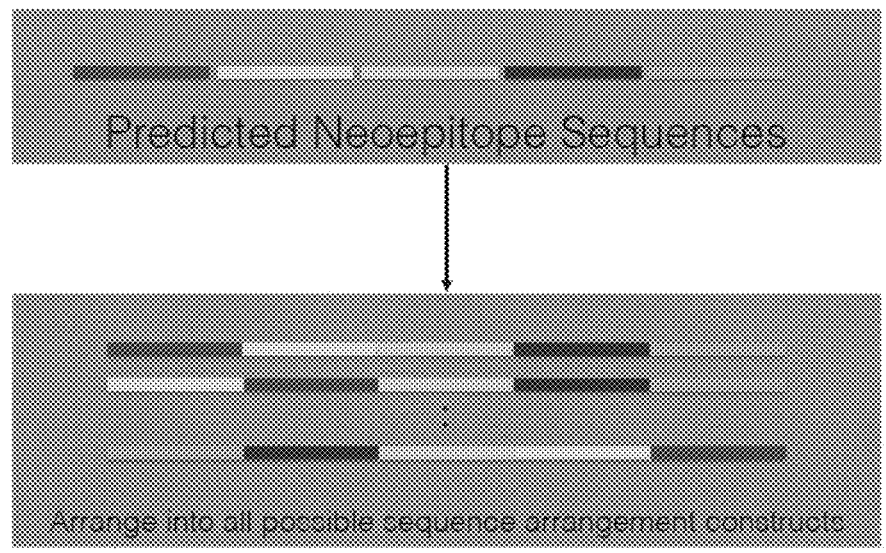
Figure 2

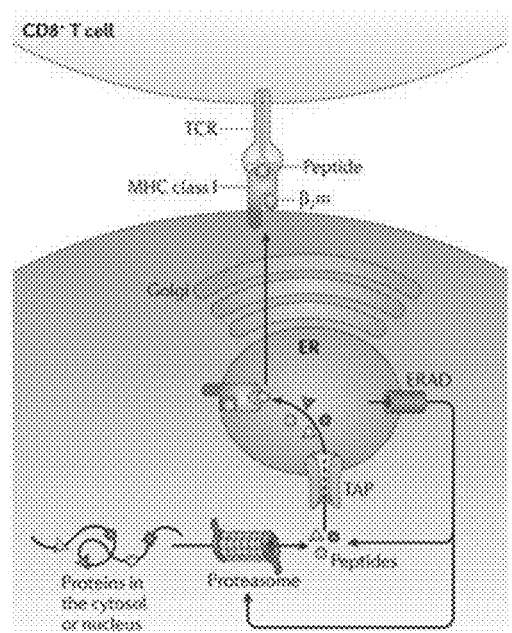
Prior Art Figure 3
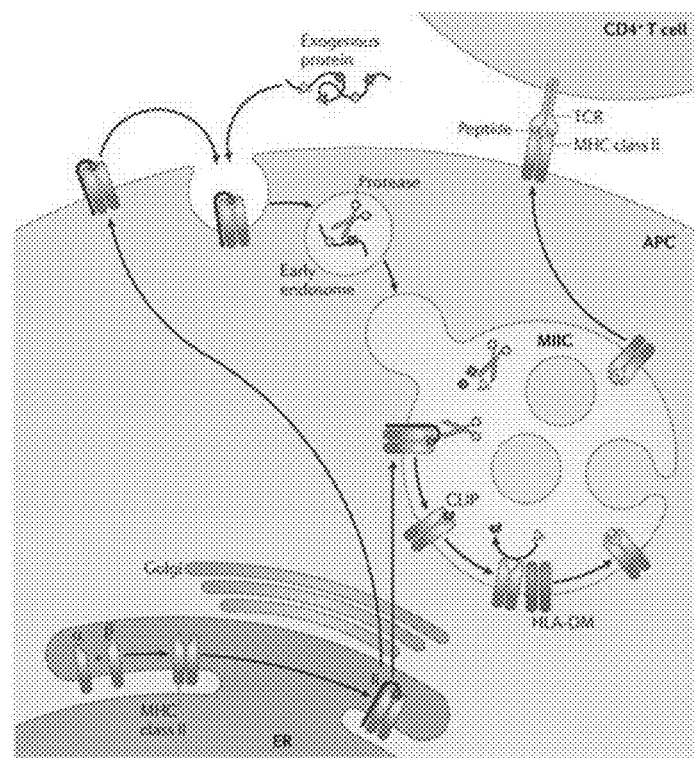
Prior Art Figure 4

MDKITQYEKSLYYCSFLEALVRDVCIAAAACVDCLDRTNTAQVMVGKCALAYQLYAAAAVVKAY
LPVNESFAFTADLRSNTGGQAAAANILAVSFAPLVQLSKNDNGTPDSVGAAAAQSNYQHITNFE
WCISILVELTRLEGAAAAYYTVFDRDNNRVSFANAVVLAAAAHSGLVTFQAFIDVMSRETTDTD
TADAAAALDLAALEDVSANCLTETLEDKNEGVAAAAVLSFVGQTRVLMINGEEVEETELMGAAA
A<u>EVSGLEQLESIINFEKLTEWTSSNV</u>AAAA*MTEQQWNFAGIEAAASAIQGNVTSIHSLLD*AAAA**E
QKLISEEDL**

Figure 5A

<u>*MQIFVKTLTGKTITLEVEPSDTIENVKAKIQDKEGIPPDQQRLIFAGKQLEDGRTLSDYNIQKESTLHLVLRL
RGGR*</u>DKITQYEKSLYYCSFLEALVRDVCIAAAACVDCLDRTNTAQVMVGKCALAYQLYAAAAVV
KAYLPVNESFAFTADLRSNTGGQAAAANILAVSFAPLVQLSKNDNGTPDSVGAAAAQSNYQHIT
NFEWCISILVELTRLEGAAAAYYTVFDRDNNRVSFANAVVLAAAAHSGLVTFQAFIDVMSRETT
DTDTADAAAALDLAALEDVSANCLTETLEDKNEGVAAAAVLSFVGQTRVLMINGEEVEETELMG
AAAA<u>EVSGLEQLESIINFEKLTEWTSSNV</u>AAAA*MTEQQWNFAGIEAAASAIQGNVTSIHSLLD*AA
AAEQKLISEEDL

Figure 5B

<u>*MQIFVKTLTGKTITLEVEPSDTIENVKAKIQDKEGIPPDQQRLIFAGKQLEDGRTLSDYNIQKESTLHLVLRL
RG*</u>DKITQYEKSLYYCSFLEALVRDVCIAAAACVDCLDRTNTAQVMVGKCALAYQLYAAAAVVKAYLPVNE
SFAFTADLRSNTGGQAAAANILAVSFAPLVQLSKNDNGTPDSVGAAAAQSNYQHITNFEWCISILVELTRL
EGAAAAYYTVFDRDNNRVSFANAVVLAAAAHSGLVTFQAFIDVMSRETTDTDTADAAAALDLAALEDVSA
NCLTETLEDKNEGVAAAAVLSFVGQTRVLMINGEEVEETELMGAAAA<u>EVSGLEQLESIINFEKLTEWTSSN
V</u>AAAA*MTEQQWNFAGIEAAASAIQGNVTSIHSLLD*AAAAEQKLISEEDL

Figure 5C

MLLLPFQLLAVLFPGGNSEDKITQYEKSLYYCSFLEALVRDVCIGPGPGCVDCLDRTNTAQVMVGKCALA
YQLYGPGPGVVKAYLPVNESFAFTADLRSNTGGQGPGPGNILAVSFAPLVQLSKNDNGTPDSVGGPGP
GQSNYQHITNFEWCISILVELTRLEGGPGPGYYTVFDRDNNRVSFANAVVLGPGPGHSGLVTFQAFIDVM
SRETTDTDTADGPGPGLDLAALEDVSANCLTETLEDKNEGVGPGPGVLSFVGQTRVLMINGEEVEETEL
MGGPGPGEVSGLEQLESIINFEKLTEWTSSNVGGPGPGMTEQQWNFAGIEAAASAIQGNVTSIHSLLD*DY*
*KDDDDKGSDYKDHDGDYKDHD*MLIPIAVGGALAGLVLIVLIAYLIGRKRSHAGYQTI

Figure 6A

MLLLPFQLLAVLFPGGNSEDKITQYEKSLYYCSFLEALVRDVCIGPGPGCVDCLDRTNTAQVMVGKCALAYQLYGPG
PGVVKAYLPVNESFAFTADLRSNTGGQGPGPGNILAVSFAPLVQLSKNDNGTPDSVGGPGPGQSNYQHITNFEWCIS
ILVELTRLEGGPGPGYYTVFDRDNNRVSFANAVVLGPGPGHSGLVTFQAFIDVMSRETTDTDTADGPGPGLDLAALE
DVSANCLTETLEDKNEGVGPGPGVLSFVGQTRVLMINGEEVEETELMGGPGPGEVSGLEQLESIINFEKLTEWTSSN
VGGPGPGMTEQQWNFAGIEAAASAIQGNVTSIHSLLD*DYKDDDDKGSDYKDHDGDYKDHD.I*MLIPIAVGGALAGLVL
IVLIAYLIG*RKRCFC*

Figure 6B

MLLLPFQLLAVLFPGGNSEDKITQYEKSLYYCSFLEALVRDVCIGPGPGCVDCLDRTNTAQVMVGKCALA
YQLYGPGPGVVKAYLPVNESFAFTADLRSNTGGQGPGPGNILAVSFAPLVQLSKNDNGTPDSVGGPGP
GQSNYQHITNFEWCISILVELTRLEGGPGPGYYTVFDRDNNRVSFANAVVLGPGPGHSGLVTFQAFIDVM
SRETTDTDTADGPGPGLDLAALEDVSANCLTETLEDKNEGVGPGPGVLSFVGQTRVLMINGEEVEETEL
MGGPGPGEVSGLEQLESIINFEKLTEWTSSNVGGPGPGMTEQQWNFAGIEAAASAIQGNVTSIHSLLD*DY*
*KDDDDKGSDYKDHDGDYKDHD*MLIPIAVGGALAGLVLIVLIAYLIG*KKHCSYQDIL*

Figure 6C

MLLLPFQLLAVLFPGGNSEALQAYHLDPQCWGVNVQPYSGSPANVAVYTALVEPHGRIMGLD
LPDGGHLTGPGPGDTDEAEDPEKMLANFESGKHKYRQTAMFTATMPPAVERLARSYLRRPAV
VYGPGPGRRYLLQNTALEVFMANRTSVMFNFPEQATVKKVVYSLPRVGVGTSYGLPQAGPGP
GKIEPDMMSMEHSFETASHDGEAGPSPEVLQGPGPGKVLMASTSYLPSQVTEMFNQGRAFA
AVRLPFCGHKNICSLTTIQKIPRLLVGPGPGMPAAELALSAFLVLVFLWVHSLRRLLECFYVSVF
SNAAIHVVQYCFGLVYYGPGPGLLELLHCPLGHCHLCSEPMFTFVYPTIFPLRETPMAGLHQRR
TSIGFVAYCGPGPGAHFRLVSKEKMPWDSIKLTFEATGPRHMSFYVRTHKGSTLSQWSLGNGI
PVGPGPGGRTQQMLIPAWQQVTPMAPAAATLTFEGMAGSQRLGDWGKMIPHSNHYNSVGP
GPGELQLVQLEGGGGSGTYRVGNAQPSLADCLDAGDLAQRLREHGAEVPTEPKEGPGPGEL
EKFRKSEEGKQRAAAPSAASSPADVQSLKKAMSSLQNDRDRLLKELKNLGPGPGGKHDRDLLI
GTAKHGLNRTDYYIMNGPQLSFLDAYRNYAQHKRTDTQAPGSGPGPGILEVDKSGPITLLVQG
HMEGEVWGLSTHPYLPICATVSDDKTLRIWDLSPSGPGPGMLTARLLLPRLLCLQGRTTSYST
AAVLPNPIPNPEICYNKLFINNEWHDAVGPGPG<u>EVSGLEQLESIINFEKLTEWTSSNVGGPGPG
MTEQQWNFAGIEAAASAIQGNVTSIHSLLD</u>*DYKDDDDKGSDYKDHGDYKDHD***IMLIPIAVGG
ALAGLVLIVLIAYLIG**RKRSHAGYQTI

Figure 7A

MLLLPFQLLAVLFPGGNSEALQAYHLDPQCWGVNVQPYSGSPANVAVYTALVEPHGRIMGLDLPDGGH
LTGPGPGDTDEAEDPEKMLANFESGKHKYRQTAMFTATMPPAVERLARSYLRRPAVVYGPGPGRRYLL
QNTALEVFMANRTSVMFNFPEQATVKKVVYSLPRVGVGTSYGLPQAGPGPGKIEPDMMSMEHSFETAS
HDGEAGPSPEVLQGPGPGKVLMASTSYLPSQVTEMFNQGRAFAAVRLPFCGHKNICSLTTIQKIPRLLVG
PGPGMPAAELALSAFLVLVFLWVHSLRRLLECFYVSVFSNAAIHVVQYCFGLVYYGPGPGLLELLHCPLG
HCHLCSEPMFTFVYPTIFPLRETPMAGLHQRRTSIGFVAYCGPGPGAHFRLVSKEKMPWDSIKLTFEATG
PRHMSFYVRTHKGSTLSQWSLGNGIPVGPGPGGRTQQMLIPAWQQVTPMAPAAATLTFEGMAGSQRL
GDWGKMIPHSNHYNSVGPGPGELQLVQLEGGGGSGTYRVGNAQPSLADCLDAGDLAQRLREHGAEVP
TEPKEGPGPGELEKFRKSEEGKQRAAAPSAASSPADVQSLKKAMSSLQNDRDRLLKELKNLGPGPGGK
HDRDLLIGTAKHGLNRTDYYIMNGPQLSFLDAYRNYAQHKRTDTQAPGSGPGPGILEVDKSGPITLLVQG
HMEGEVWGLSTHPYLPICATVSDDKTLRIWDLSPSGPGPGMLTARLLLPRLLCLQGRTTSYSTAAVLPNPI
PNPEICYNKLFINNEWHDAVGPGPG<u>EVSGLEQLESIINFEKLTEWTSSNVGGPGPGMTEQQWNFAGIEA
AASAIQGNVTSIHSLLD</u>*DYKDDDDKGSDYKDHGDYKDHD*IMLIPIAVGGALAGLVLIVLIAYLIG*RKRCFC*

Figure 7B

MLLLPFQLLAVLFPGGNSEALQAYHLDPQCWGVNVQPYSGSPANVAVYTALVEPHGRIMGLDLPDGGH
LTGPGPGDTDEAEDPEKMLANFESGKHKYRQTAMFTATMPPAVERLARSYLRRPAVVYGPGPGRRYLL
QNTALEVFMANRTSVMFNFPEQATVKKVVYSLPRVGVGTSYGLPQAGPGPGKIEPDMMSMEHSFETAS
HDGEAGPSPEVLQGPGPGKVLMASTSYLPSQVTEMFNQGRAFAAVRLPFCGHKNICSLTTIQKIPRLLVG
PGPGMPAAELALSAFLVLVFLWVHSLRRLLECFYVSVFSNAAIHVVQYCFGLVYYGPGPGLLELLHCPLG
HCHLCSEPMFTFVYPTIFPLRETPMAGLHQRRTSIGFVAYCGPGPGAHFRLVSKEKMPWDSIKLTFEATG
PRHMSFYVRTHKGSTLSQWSLGNGIPVGPGPGGRTQQMLIPAWQQVTPMAPAAATLTFEGMAGSQRL
GDWGKMIPHSNHYNSVGPGPGELQLVQLEGGGGSGTYRVGNAQPSLADCLDAGDLAQRLREHGAEVP
TEPKEGPGPGELEKFRKSEEGKQRAAAPSAASSPADVQSLKKAMSSLQNDRDRLLKELKNLGPGPGGK
HDRDLLIGTAKHGLNRTDYYIMNGPQLSFLDAYRNYAQHKRTDTQAPGSGPGPGILEVDKSGPITLLVQG
HMEGEVWGLSTHPYLPICATVSDDKTLRIWDLSPSGPGPGMLTARLLLPRLLCLQGRTTSYSTAAVLPNPI
PNPEICYNKLFINNEWHDAVGPGPG<u>EVSGLEQLESIINFEKLTEWTSSNVGGPGPGMTEQQWNFAGIEA
AASAIQGNVTSIHSLLD</u>*DYKDDDDKGSDYKDHGDYKDHD*IMLIPIAVGGALAGLVLIVLIAYLIG*KKHCSY
QDIL*

Figure 7C

SEQUENCE LISTING

<160> NUMBER OF SEQ ID NOS: 26

<210> SEQ ID NO 1
<211> LENGTH: 402
<212> TYPE: DNA
<213> ORGANISM: Artificial Sequence
<220> FEATURE:
<223> OTHER INFORMATION: Recombinant construct 1

<400> SEQUENCE: 1
ctcgaggaag cttgccgcca ccatgccatt tgccatggcc cagatcccca gcctgagcct     60
gagagctgtg ctgcctaatg tgaccgtgcg gaacgccacc agctacagat gtggcagctg    120
gttcagagag ggcaagaccc tgaacccag ccagaccagc gccgtgatgg actgggtgtg    180
gatggacacc accctgtccc tgagcctggg ccccgagaga agaaagctga ccaccgagct    240
gacaatcatc aacaatggcc tgggcgctca gtgtagcgag gccgtgaccc tgaataatgt    300
gggcgagaca gtgaccatgc cctgccccaa ggtgttcagc tgccagggcc ccgaacaagt    360
gtggggaatg gctgtgcgcg agctgtgaga tatcgcggcc gc                       402

<210> SEQ ID NO 2
<211> LENGTH: 591
<212> TYPE: DNA
<213> ORGANISM: Artificial Sequence
<220> FEATURE:
<223> OTHER INFORMATION: Artificial construct 2

<400> SEQUENCE: 2
ctcgaggaag cttgccgcca ccatgccatt tgccatggcc cagatcccca gcctgagcct     60

```
gagagctgtg ggaagcggga gtggctcagg ttcaggactg cctaatgtga ccgtgcggaa    120
cgccaccagc tacagatgtg cggaagtggg gtcaggctcc ggttctggaa gctggttcag    180
agagggcaag accctgaacc ccagccagac cagcgggtca ggaagtggta gcggctccgg    240
ggccgtgatg gactgggtgt ggatggacac caccctgtcc ctgagcggaa gtggatcagg    300
ttccggctct gggctgggcc cgagagaag aaagctgacc accgagctga caatcatcgg    360
atccgggtct ggcagtggtt caggcaacaa tggcctgggc gctcagtgta gcgaggccgt    420
gaccctgaat ggatcagggt ccggcagcgg tagtggcaat gtgggcgaga cagtgaccat    480
gccctgcccc aaggtgttca gcgggtccgg atctggtagt ggctcaggtt gccagggccc    540
cgaacaagtg tggggaatgg ctgtgcgcga gctgtgagat atcgcggccg c             591
```

<210> SEQ ID NO 3
<211> LENGTH: 642
<212> TYPE: DNA
<213> ORGANISM: Artificial Sequence
<220> FEATURE:
<223> OTHER INFORMATION: Artificial construct 3

<400> SEQUENCE: 3

```
ctcgaggaag cttgccgcca ccatgcctag cgagagccct ccatttgcca tggcccagat     60
ccccagcctg agcctgagag ctgtgtctgg cgctatggga gcccacagca tcccctgcc    120 taatgtgacc gtgcggaacg ccaccagcta cagatgtggc gtgggacctc ctggccctcc    180
tgcttccctg agctggttca gagagggcaa gaccctgaac cccagccaga ccagcatgag    240
cggcacccct ctgacagagc tgagagccgt gatggactgg gtgtggatgg acaccaccct    300
gtccctgagc agctggatct gtgtggtgtc cgccacagac ctgggccccg agaagaaaa    360 gctgaccacc gagctgacaa tcatcctgca gggcctggac tacagctgcg aggccaacaa    420
tggcctgggc gctcagtgta gcgaggccgt gaccctgaat ttcaccgtgc ccacctgttg    480
gaggcccgcc aatgtgggcg agacagtgac catgccctgc cccaaggtgt tcagcaactt    540
ctacagcaaa gtgcgggggct tcatgtgcca ggggcccgaa caagtgtggg gaatggctgt    600
gcgcgagctg aacatgaacc tgctgtgaga tatcgcggcc gc                       642
```

<210> SEQ ID NO 4
<211> LENGTH: 831
<212> TYPE: DNA
<213> ORGANISM: Artificial Sequence
<220> FEATURE:
<223> OTHER INFORMATION: Artificial Construct 4

<400> SEQUENCE: 4

```
ctcgaggaag cttgccgcca ccatgcctag cgagagccct ccatttgcca tggcccagat     60
ccccagcctg agcctgagag ctgtgtctgg cgctatggga ggaagcggga gtggctcagg    120
ttcaggagcc cacagcatcc ccctgcctaa tgtgaccgtg cggaacgcca ccagctacag    180
atgtggcgtg ggacctcctg gcggaagtgg gtcaggctcc ggttctggac tcctgcttc    240 cctgagctgg ttcagagagg gcaagaccct gaaccccagc cagaccagca tgagcggcac    300
cctggggtca ggaagtggta gcggctccgg gctgacagag ctgagagccg tgatggactg    360
ggtgtggatg gacaccaccc tgtccctgag cagctggatc tgtgtgggaa gtggatcagg    420
ttccggctct ggggtgtccg ccacagacct gggccccgag agaagaaagc tgaccaccga    480
gctgacaatc atcctgcagg gcctggacgg atccgggtct ggcagtggtt caggctacag    540
```

```
ctgcgaggcc aacaatggcc tgggcgctca gtgtagcgag gccgtgaccc tgaatttcac    600
cgtgcccacc ggatcagggt ccggcagcgg tagtggctgt tggaggcccg ccaatgtggg    660
cgagacagtg accatgccct gccccaaggt gttcagcaac ttctacagca agggtccgg     720 atctggtagt ggctcaggtg tgcggggctt catgtgccag ggccccgaac aagtgtgggg    780
aatggctgtg cgcgagctga acatgaacct gctgtgagat atcgcggccg c            831
```

```
<210> SEQ ID NO 5
<211> LENGTH: 121
<212> TYPE: PRT
<213> ORGANISM: Artificial Sequence
<220> FEATURE:
<223> OTHER INFORMATION: Artificial construct 1 protein sequence

<400> SEQUENCE: 5

Met Pro Phe Ala Met Ala Gln Ile Pro Ser Leu Ser Leu Arg Ala Val
1               5                   10                  15

Leu Pro Asn Val Thr Val Arg Asn Ala Thr Ser Tyr Arg Cys Gly Ser
            20                  25                  30

Trp Phe Arg Glu Gly Lys Thr Leu Asn Pro Ser Gln Thr Ser Ala Val
        35                  40                  45

Met Asp Trp Val Trp Met Asp Thr Thr Leu Ser Leu Ser Leu Gly Pro
    50                  55                  60

Glu Arg Arg Lys Leu Thr Thr Glu Leu Thr Ile Ile Asn Asn Gly Leu
65                  70                  75                  80

Gly Ala Gln Cys Ser Glu Ala Val Thr Leu Asn Asn Val Gly Glu Thr
                85                  90                  95

Val Thr Met Pro Cys Pro Lys Val Phe Ser Cys Gln Gly Pro Glu Gln
            100                 105                 110

Val Trp Gly Met Ala Val Arg Glu Leu
        115                 120

<210> SEQ ID NO 6
<211> LENGTH: 184
<212> TYPE: PRT
<213> ORGANISM: Artificial Sequence
<220> FEATURE:
<223> OTHER INFORMATION: Artificial construct 2 protein sequence

<400> SEQUENCE: 6

Met Pro Phe Ala Met Ala Gln Ile Pro Ser Leu Ser Leu Arg Ala Val
1               5                   10                  15

Gly Ser Gly Ser Gly Ser Gly Ser Leu Pro Asn Val Thr Val Arg
            20                  25                  30

Asn Ala Thr Ser Tyr Arg Cys Gly Ser Gly Ser Gly Ser Gly Ser
        35                  40                  45

Gly Ser Trp Phe Arg Glu Gly Lys Thr Leu Asn Pro Ser Gln Thr Ser
    50                  55                  60

Gly Ser Gly Ser Gly Ser Gly Ala Val Met Asp Trp Val Trp
65                  70                  75                  80

Met Asp Thr Thr Leu Ser Leu Ser Gly Ser Gly Ser Gly Ser
                85                  90                  95

Gly Leu Gly Pro Glu Arg Arg Lys Leu Thr Thr Glu Leu Thr Ile Ile
            100                 105                 110

Gly Ser Gly Ser Gly Ser Gly Asn Asn Gly Leu Gly Ala Gln
        115                 120                 125

Cys Ser Glu Ala Val Thr Leu Asn Gly Ser Gly Ser Gly Ser Gly Ser
```

130                 135                 140
Gly Asn Val Gly Glu Thr Val Thr Met Pro Cys Pro Lys Val Phe Ser
145                 150                 155                 160

Gly Ser Gly Ser Gly Ser Gly Cys Gln Gly Pro Glu Gln Val
                165                 170                 175

Trp Gly Met Ala Val Arg Glu Leu
            180

<210> SEQ ID NO 7
<211> LENGTH: 201
<212> TYPE: PRT
<213> ORGANISM: Artificial Sequence
<220> FEATURE:
<223> OTHER INFORMATION: Artificial construct 3 protein sequence

<400> SEQUENCE: 7

Met Pro Ser Glu Ser Pro Pro Phe Ala Met Ala Gln Ile Pro Ser Leu
1               5                   10                  15

Ser Leu Arg Ala Val Ser Gly Ala Met Gly Ala His Ser Ile Pro Leu
            20                  25                  30

Pro Asn Val Thr Val Arg Asn Ala Thr Ser Tyr Arg Cys Gly Val Gly
        35                  40                  45

Pro Pro Gly Pro Pro Ala Ser Leu Ser Trp Phe Arg Glu Gly Lys Thr
    50                  55                  60

Leu Asn Pro Ser Gln Thr Ser Met Ser Gly Thr Leu Leu Thr Glu Leu
65                  70                  75                  80

Arg Ala Val Met Asp Trp Val Trp Met Asp Thr Thr Leu Ser Leu Ser
                85                  90                  95

Ser Trp Ile Cys Val Val Ser Ala Thr Asp Leu Gly Pro Glu Arg Arg
            100                 105                 110

Lys Leu Thr Thr Glu Leu Thr Ile Ile Leu Gln Gly Leu Asp Tyr Ser
        115                 120                 125

Cys Glu Ala Asn Asn Gly Leu Gly Ala Gln Cys Ser Glu Ala Val Thr
    130                 135                 140

Leu Asn Phe Thr Val Pro Thr Cys Trp Arg Pro Ala Asn Val Gly Glu
145                 150                 155                 160

Thr Val Thr Met Pro Cys Pro Lys Val Phe Ser Asn Phe Tyr Ser Lys
                165                 170                 175

Val Arg Gly Phe Met Cys Gln Gly Pro Glu Gln Val Trp Gly Met Ala
            180                 185                 190

Val Arg Glu Leu Asn Met Asn Leu Leu
        195                 200

<210> SEQ ID NO 8
<211> LENGTH: 264
<212> TYPE: PRT
<213> ORGANISM: Artificial Sequence
<220> FEATURE:
<223> OTHER INFORMATION: Artificial construct 4 protein sequence

<400> SEQUENCE: 8

Met Pro Ser Glu Ser Pro Pro Phe Ala Met Ala Gln Ile Pro Ser Leu
1               5                   10                  15

Ser Leu Arg Ala Val Ser Gly Ala Met Gly Gly Ser Gly Ser Gly Ser
            20                  25                  30

Gly Ser Gly Ala His Ser Ile Pro Leu Pro Asn Val Thr Val Arg Asn
        35                  40                  45

Ala Thr Ser Tyr Arg Cys Gly Val Gly Pro Pro Gly Ser Gly Ser
    50                  55                  60

Gly Ser Gly Ser Gly Pro Pro Ala Ser Leu Ser Trp Phe Arg Glu Gly
65                  70                  75                  80

Lys Thr Leu Asn Pro Ser Gln Thr Ser Met Ser Gly Thr Leu Gly Ser
                85                  90                  95

Gly Ser Gly Ser Gly Ser Gly Leu Thr Glu Leu Arg Ala Val Met Asp
                100                 105                 110

Trp Val Trp Met Asp Thr Thr Leu Ser Leu Ser Ser Trp Ile Cys Val
            115                 120                 125

Gly Ser Gly Ser Gly Ser Gly Ser Gly Val Ser Ala Thr Asp Leu Gly
            130                 135                 140

Pro Glu Arg Arg Lys Leu Thr Thr Glu Leu Thr Ile Ile Leu Gln Gly
145                 150                 155                 160

Leu Asp Gly Ser Gly Ser Gly Ser Gly Tyr Ser Cys Glu Ala
                165                 170                 175

Asn Asn Gly Leu Gly Ala Gln Cys Ser Glu Ala Val Thr Leu Asn Phe
            180                 185                 190

Thr Val Pro Thr Gly Ser Gly Ser Gly Ser Gly Cys Trp Arg
                195                 200                 205

Pro Ala Asn Val Gly Glu Thr Val Thr Met Pro Cys Pro Lys Val Phe
210                 215                 220

Ser Asn Phe Tyr Ser Lys Gly Ser Gly Ser Gly Ser Gly Ser Gly Val
225                 230                 235                 240

Arg Gly Phe Met Cys Gln Gly Pro Glu Gln Val Trp Gly Met Ala Val
                245                 250                 255

Arg Glu Leu Asn Met Asn Leu Leu
                260

<210> SEQ ID NO 9
<211> LENGTH: 993
<212> TYPE: DNA
<213> ORGANISM: Artificial Sequence
<220> FEATURE:
<223> OTHER INFORMATION: MHC-I nucleic acid for MHC-I presentation

<400> SEQUENCE: 9
atggataaaa tcacgcagta cgaaaagtca ttgtactatt gttctttcct ggaggccctc      60
gttagagatg tatgcatcgc tgcagctgcc tgtgtcgact gtcttgacag aaccaacacc     120
gcccaggtaa tggttggaaa atgtgctctg gcctaccagc tgtatgcagc cgccgcagtg     180
gtcaaagcat acctgcctgt caatgaatct ttcgccttca ctgccgattt gaggagcaat     240
actggcggcc aggcagcagc cgcaaacatc ctggctgtgt ccttcgcacc tctggtgcaa     300
ctcagtaaaa acgacaacgg aactcctgac tccgtgggag cagccgccgc acagagtaac     360
taccagcaca tcacgaattt tgagtggtgc atttccatac tggttgaact gacgcgcctg     420
gagggtgcag ctgccgctta ttacacagtg ttcgatcggg acaacaatcg ggtctctttt     480
gctaatgctg tggtgctggc cgctgccgct cacagcggac tggtcacttt ccaagccttt     540
attgatgtga tgtcaaggga acaactgac acagacactg cagacgctgc cgcagccctg     600
gatctggccg ctttggaaga cgtctccgcc aactgtctca ctgagaccct ggaggacaag     660
aatgaaggtg tggccgctgc cgctgtcctg tcattcgtgg ccagacgag ggtgttgatg     720 atcaacgggg aagaagttga agaaacagaa ctgatgggtg ccgctgccgc agaggtgtcc     780
ggactcgagc agctggaatc tataattaac tttgaaaagt tgacggaatg gacttcctct     840

```
aacgtggccg ctgccgctat gacggagcaa caatggaact tcgcaggcat cgaggctgcc    900
gccagcgcca tccaaggaaa cgtaacttca atccacagcc ttctggatgc tgctgctgcc    960
gaacaaaagc tcatcagtga ggaggacttg taa                                  993
```

```
<210> SEQ ID NO 10
<211> LENGTH: 1221
<212> TYPE: DNA
<213> ORGANISM: Artificial Sequence
<220> FEATURE:
<223> OTHER INFORMATION: MHC-I nucleic acid for MHC-I presentation
      (Ubiquitin, cleavable)

<400> SEQUENCE: 10
```

```
atgcagattt ttgtgaagac actgaccgga aaaactatca ccctcgaggt ggagccttcc     60
gacactatcg aaaacgtcaa ggccaagatc caggacaagg aaggcattcc acccgatcag    120
cagcgcctta ttttgcagg taagcagctg gaagacggaa ggaccctgag cgactataat     180
atccagaaag aaagcacact ccacctcgtg ctcaggctcc gcggggcag ggataaaatc     240 acgcagtacg aaaagtcatt gtactattgt tctttcctgg aggccctcgt tagagatgta    300
tgcatcgctg cagctgcctg tgtcgactgt cttgacagaa ccaacaccgc ccaggtaatg    360
gttggaaaat gtgctctggc ctaccagctg tatgcagccg ccgcagtggt caaagcatac    420
ctgcctgtca atgaatcttt cgccttcact gccgatttga ggagcaatac tggcggccag    480
gcagcagccg caaacatcct ggctgtgtcc ttcgcacctc tggtgcaact cagtaaaaac    540
gacaacggaa ctcctgactc cgtgggagca gccgccgcac agagtaacta ccagcacatc    600
acgaattttg agtggtgcat ttccatactg gttgaactga cgcgcctgga gggtgcagct    660
gccgcttatt acacagtgtt cgatcgggac aacaatcggg tctcttttgc taatgctgtg    720
gtgctggccg ctgccgctca cagcggactg gtcactttcc aagcctttat tgatgtgatg    780
tcaagggaaa caactgacac agacactgca gacgctgccg cagccctgga tctggccgct    840
ttggaagacg tctccgccaa ctgtctcact gagaccctgg aggacaagaa tgaaggtgtg    900
gccgctgccg ctgtcctgtc attcgtgggc cagacgaggt gttgatgat caacggggaa    960 gaagttgaag aaacagaact gatgggtgcc gctgccgcag aggtgtccgg actcgagcag   1020
ctggaatcta taattaactt tgaaaagttg acggaatgga cttcctctaa cgtgccgct    1080 gccgctatga cggagcaaca atggaacttc gcaggcatcg aggctgccgc agcgccatc    1140 caaggaaacg taacttcaat ccacagcctt ctggatgctg ctgctgccga caaaagctc    1200 atcagtgagg aggacttgta a                                             1221
```

```
<210> SEQ ID NO 11
<211> LENGTH: 1215
<212> TYPE: DNA
<213> ORGANISM: Artificial Sequence
<220> FEATURE:
<223> OTHER INFORMATION: MHC-I nucleic acid for MHC-I presentation
      (Ubiquitin, non-cleavable)

<400> SEQUENCE: 11
```

```
atgcagattt ttgtgaagac actgaccgga aaaactatca ccctcgaggt ggagccttcc     60
gacactatcg aaaacgtcaa ggccaagatc caggacaagg aaggcattcc acccgatcag    120
cagcgcctta ttttgcagg taagcagctg gaagacggaa ggaccctgag cgactataat     180
atccagaaag aaagcacact ccacctcgtg ctcaggctcc gcggggataa aatcacgcag    240
```

```
tacgaaaagt cattgtacta ttgttctttc ctggaggccc tcgttagaga tgtatgcatc    300
gctgcagctg cctgtgtcga ctgtcttgac agaaccaaca ccgcccaggt aatggttgga    360
aaatgtgctc tggcctacca gctgtatgca gccgccgcag tggtcaaagc atacctgcct    420
gtcaatgaat ctttcgcctt cactgccgat ttgaggagca atactggcgg ccaggcagca    480
gccgcaaaca tcctggctgt gtccttcgca cctctggtgc aactcagtaa aaacgacaac    540
ggaactcctg actccgtggg agcagccgcc gcacagagta actaccagca catcacgaat    600
tttgagtggt gcatttccat actggttgaa ctgacgcgcc tggagggtgc agctgccgct    660
tattacacag tgttcgatcg ggacaacaat cgggtctctt ttgctaatgc gtggtgctg     720 gccgctgccg ctcacagcgg actggtcact ttccaagcct ttattgatgt gatgtcaagg    780
gaaacaactg acacagacac tgcagacgct gccgcagccc tggatctggc cgctttggaa    840
gacgtctccg ccaactgtct cactgagacc ctggaggaca gaatgaagg tgtggccgct     900 gccgctgtcc tgtcattcgt gggccagacg agggtgttga tgatcaacgg ggaagaagtt    960
gaagaaacag aactgatggg tgccgctgcc gcagaggtgt ccggactcga gcagctggaa    1020
tctataatta actttgaaaa gttgacggaa tggacttcct ctaacgtggc cgctgccgct    1080
atgacggagc aacaatggaa cttcgcaggc atcgaggctg ccgccagcgc catccaagga    1140
aacgtaactt caatccacag ccttctggat gctgctgctg ccgaacaaaa gctcatcagt    1200
gaggaggact gtaa                                                     1215

<210> SEQ ID NO 12
<211> LENGTH: 330
<212> TYPE: PRT
<213> ORGANISM: Artificial Sequence
<220> FEATURE:
<223> OTHER INFORMATION: MHC-I polypeptide for MHC-I presentation

<400> SEQUENCE: 12

Met Asp Lys Ile Thr Gln Tyr Glu Lys Ser Leu Tyr Tyr Cys Ser Phe
1               5                   10                  15

Leu Glu Ala Leu Val Arg Asp Val Cys Ile Ala Ala Ala Cys Val
            20                  25                  30

Asp Cys Leu Asp Arg Thr Asn Thr Ala Gln Val Met Val Gly Lys Cys
        35                  40                  45

Ala Leu Ala Tyr Gln Leu Tyr Ala Ala Ala Val Val Lys Ala Tyr
    50                  55                  60

Leu Pro Val Asn Glu Ser Phe Ala Phe Thr Ala Asp Leu Arg Ser Asn
65                  70                  75                  80

Thr Gly Gly Gln Ala Ala Ala Asn Ile Leu Ala Val Ser Phe Ala
            85                  90                  95

Pro Leu Val Gln Leu Ser Lys Asn Asp Asn Gly Thr Pro Asp Ser Val
            100                 105                 110

Gly Ala Ala Ala Gln Ser Asn Tyr Gln His Ile Thr Asn Phe Glu
        115                 120                 125

Trp Cys Ile Ser Ile Leu Val Glu Leu Thr Arg Leu Glu Gly Ala Ala
    130                 135                 140

Ala Ala Tyr Tyr Thr Val Phe Asp Arg Asp Asn Asn Arg Val Ser Phe
145                 150                 155                 160

Ala Asn Ala Val Val Leu Ala Ala Ala His Ser Gly Leu Val Thr
            165                 170                 175

Phe Gln Ala Phe Ile Asp Val Met Ser Arg Glu Thr Thr Asp Thr Asp
            180                 185                 190
```

```
Thr Ala Asp Ala Ala Ala Ala Leu Asp Leu Ala Ala Leu Glu Asp Val
        195                 200                 205

Ser Ala Asn Cys Leu Thr Glu Thr Leu Glu Asp Lys Asn Glu Gly Val
210                 215                 220

Ala Ala Ala Ala Val Leu Ser Phe Val Gly Gln Thr Arg Val Leu Met
225                 230                 235                 240

Ile Asn Gly Glu Glu Val Glu Glu Thr Glu Leu Met Gly Ala Ala Ala
                245                 250                 255

Ala Glu Val Ser Gly Leu Glu Gln Leu Glu Ser Ile Ile Asn Phe Glu
                260                 265                 270

Lys Leu Thr Glu Trp Thr Ser Ser Asn Val Ala Ala Ala Met Thr
                275                 280                 285

Glu Gln Gln Trp Asn Phe Ala Gly Ile Glu Ala Ala Ala Ser Ala Ile
        290                 295                 300

Gln Gly Asn Val Thr Ser Ile His Ser Leu Leu Asp Ala Ala Ala Ala
305                 310                 315                 320

Glu Gln Lys Leu Ile Ser Glu Glu Asp Leu
                325                 330
```

<210> SEQ ID NO 13
<211> LENGTH: 406
<212> TYPE: PRT
<213> ORGANISM: Artificial Sequence
<220> FEATURE:
<223> OTHER INFORMATION: MHC-I polypeptide for MHC-I presentation
      (Ubiquitin, cleavable)

<400> SEQUENCE: 13

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
50                  55                  60

Ser Thr Leu His Leu Val Leu Arg Leu Arg Gly Gly Arg Asp Lys Ile
65                  70                  75                  80

Thr Gln Tyr Glu Lys Ser Leu Tyr Tyr Cys Ser Phe Leu Glu Ala Leu
                85                  90                  95

Val Arg Asp Val Cys Ile Ala Ala Ala Cys Val Asp Cys Leu Asp
                100                 105                 110

Arg Thr Asn Thr Ala Gln Val Met Val Gly Lys Cys Ala Leu Ala Tyr
            115                 120                 125

Gln Leu Tyr Ala Ala Ala Val Val Lys Ala Tyr Leu Pro Val Asn
130                 135                 140

Glu Ser Phe Ala Phe Thr Ala Asp Leu Arg Ser Asn Thr Gly Gly Gln
145                 150                 155                 160

Ala Ala Ala Ala Asn Ile Leu Ala Val Ser Phe Ala Pro Leu Val Gln
                165                 170                 175

Leu Ser Lys Asn Asp Asn Gly Thr Pro Asp Ser Val Gly Ala Ala Ala
                180                 185                 190

Ala Gln Ser Asn Tyr Gln His Ile Thr Asn Phe Glu Trp Cys Ile Ser
            195                 200                 205

Ile Leu Val Glu Leu Thr Arg Leu Glu Gly Ala Ala Ala Ala Tyr Tyr
```

-continued

```
                210                 215                 220
Thr Val Phe Asp Arg Asp Asn Asn Arg Val Ser Phe Ala Asn Ala Val
225                 230                 235                 240

Val Leu Ala Ala Ala His Ser Gly Leu Val Thr Phe Gln Ala Phe
                245                 250                 255

Ile Asp Val Met Ser Arg Glu Thr Thr Asp Thr Asp Thr Ala Asp Ala
                260                 265                 270

Ala Ala Ala Leu Asp Leu Ala Ala Leu Glu Asp Val Ser Ala Asn Cys
            275                 280                 285

Leu Thr Glu Thr Leu Glu Asp Lys Asn Glu Gly Val Ala Ala Ala Ala
            290                 295                 300

Val Leu Ser Phe Val Gly Gln Thr Arg Val Leu Met Ile Asn Gly Glu
305                 310                 315                 320

Glu Val Glu Glu Thr Glu Leu Met Gly Ala Ala Ala Glu Val Ser
                325                 330                 335

Gly Leu Glu Gln Leu Glu Ser Ile Ile Asn Phe Glu Lys Leu Thr Glu
            340                 345                 350

Trp Thr Ser Ser Asn Val Ala Ala Ala Met Thr Glu Gln Gln Trp
            355                 360                 365

Asn Phe Ala Gly Ile Glu Ala Ala Ser Ala Ile Gln Gly Asn Val
370                 375                 380

Thr Ser Ile His Ser Leu Leu Asp Ala Ala Ala Glu Gln Lys Leu
385                 390                 395                 400

Ile Ser Glu Glu Asp Leu
                405
```

<210> SEQ ID NO 14
<211> LENGTH: 404
<212> TYPE: PRT
<213> ORGANISM: Artificial Sequence
<220> FEATURE:
<223> OTHER INFORMATION: MHC-I polypeptide for MHC-I presentation
      (Ubiquitin, non-cleavable)

<400> SEQUENCE: 14

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Asp Lys Ile Thr Gln
65                  70                  75                  80

Tyr Glu Lys Ser Leu Tyr Tyr Cys Ser Phe Leu Glu Ala Leu Val Arg
                85                  90                  95

Asp Val Cys Ile Ala Ala Ala Cys Val Asp Cys Leu Asp Arg Thr
                100                 105                 110

Asn Thr Ala Gln Val Met Val Gly Lys Cys Ala Leu Ala Tyr Gln Leu
            115                 120                 125

Tyr Ala Ala Ala Val Val Lys Ala Tyr Leu Pro Val Asn Glu Ser
        130                 135                 140

Phe Ala Phe Thr Ala Asp Leu Arg Ser Asn Thr Gly Gly Gln Ala Ala
145                 150                 155                 160
```

| | | | | | | | | | | | |
|---|---|---|---|---|---|---|---|---|---|---|---|
|Ala|Ala|Asn|Ile|Leu|Ala|Val|Ser|Phe|Ala|Pro|Leu|Val|Gln|Leu|Ser|
| | | | |165| | | |170| | | |175| | | |

Lys Asn Asp Asn Gly Thr Pro Asp Ser Val Gly Ala Ala Ala Ala Gln
            180                 185                 190

Ser Asn Tyr Gln His Ile Thr Asn Phe Glu Trp Cys Ile Ser Ile Leu
            195                 200                 205

Val Glu Leu Thr Arg Leu Glu Gly Ala Ala Ala Tyr Tyr Thr Val
            210                 215                 220

Phe Asp Arg Asp Asn Asn Arg Val Ser Phe Ala Asn Ala Val Val Leu
225                 230                 235                 240

Ala Ala Ala Ala His Ser Gly Leu Val Thr Phe Gln Ala Phe Ile Asp
            245                 250                 255

Val Met Ser Arg Glu Thr Thr Asp Thr Asp Thr Ala Asp Ala Ala Ala
            260                 265                 270

Ala Leu Asp Leu Ala Ala Leu Glu Asp Val Ser Ala Asn Cys Leu Thr
            275                 280                 285

Glu Thr Leu Glu Asp Lys Asn Glu Gly Val Ala Ala Ala Val Leu
            290                 295                 300

Ser Phe Val Gly Gln Thr Arg Val Leu Met Ile Asn Gly Glu Val
305                 310                 315                 320

Glu Glu Thr Glu Leu Met Gly Ala Ala Ala Glu Val Ser Gly Leu
            325                 330                 335

Glu Gln Leu Glu Ser Ile Ile Asn Phe Glu Lys Leu Thr Glu Trp Thr
            340                 345                 350

Ser Ser Asn Val Ala Ala Ala Met Thr Glu Gln Gln Trp Asn Phe
            355                 360                 365

Ala Gly Ile Glu Ala Ala Ala Ser Ala Ile Gln Gly Asn Val Thr Ser
            370                 375                 380

Ile His Ser Leu Leu Asp Ala Ala Ala Glu Gln Lys Leu Ile Ser
385                 390                 395                 400

Glu Glu Asp Leu

<210> SEQ ID NO 15
<211> LENGTH: 1218
<212> TYPE: DNA
<213> ORGANISM: Artificial Sequence
<220> FEATURE:
<223> OTHER INFORMATION: MHC-I nucleic acid for MHC-II presentation
      (lysosomal target)

<400> SEQUENCE: 15

```
atgctgctgc tgccattcca gctcttggcc gtgctgttcc ccggggggaa ttctgaggat      60
aagatcaccc agtatgaaaa atccttgtat tattgtagct ttctggaagc cctggtgcga     120
gatgtgtgta taggcccagg gccggggtgt gttgattgcc tcgacaggac aaataccgcc     180
caggtaatgg ttggcaaatg cgcactcgca tatcaactct acggaccagg acccggcgtg     240
gtaaaggctt atctgccagt taacgagagc tttgccttca ccgcagacct gcgctccaat     300
actggtggtc aagggcccgg accaggtaat atcctcgccg tgagcttcgc ccctctggtc     360
cagctgagta aaaatgacaa tggtactcct gatagtgtag gcggacccgg tccgggtcag     420
tccaattacc agcacattac caatttcgaa tggtgcatca gtatactggt tgaattgacc     480
agactcgagg gggcccagg cccaggctac tacactgttt tcgatcgcga caataatcgg     540
gttagcttcg ctaatgcagt agtgctgggc cccgggccag gcactccgg tctggtgacg     600 ttccaggcct tcatcgatgt aatgagccgc gagactacgg acaccgacac cgctgatggc     660
```

```
cccgggcctg gtctggatct tgcagccctg gaggatgtgt ccgctaactg tttgactgag    720
acactggagg acaagaacga gggcgtcgga ccagggcctg gtgtcctttc tttcgtcggt    780
cagacaaggg tgttgatgat caatggagaa gaggtggaag agaccgaatt gatgggaggc    840
ccagggcccg gcgaggttag cggcctggaa cagctggaga gtattatcaa ttttgaaaag    900
ctgaccgagt ggacaagctc caatgtaggc ggacctggac ccgggatgac agagcagcag    960
tggaattttg ccggtattga agctgcagcc agtgctatcc aaggcaacgt aacgagtatt    1020
cacagcctgc tcgacgacta caaagacgac gacgacaagg gcagtgacta taaggaccat    1080
gatggtgact ataaggacca cgacatcatg ctcatcccaa tcgctgtcgg aggtgctctg    1140
gccggtctcg tattgatcgt tctgatcgct tatttgatcg ggaggaagag gagtcacgca    1200
ggctaccaga ctatctag                                                  1218

<210> SEQ ID NO 16
<211> LENGTH: 1203
<212> TYPE: DNA
<213> ORGANISM: Artificial Sequence
<220> FEATURE:
<223> OTHER INFORMATION: MHC-I nucleic acid for MHC-II presentation
      (recycling endosome target)

<400> SEQUENCE: 16
atgctgctgc tgccattcca gctcttggcc gtgctgttcc cggggggaa ttctgaggat    60 aagatcaccc agtatgaaaa atccttgtat tattgtagct ttctggaagc cctggtgcga    120
gatgtgtgta taggcccagg gccggggtgt gttgattgcc tcgacaggac aaataccgcc    180
caggtaatgg ttggcaaatg cgcactcgca tatcaactct acggaccagg acccggcgtg    240
gtaaaggctt atctgccagt taacgagagc tttgccttca ccgcagacct gcgctccaat    300
actggtggtc aagggcccgg accaggtaat atcctcgccg tgagcttcgc ccctctggtc    360
cagctgagta aaaatgacaa tggtactcct gatagtgtag cggacccggt ccgggtcag    420 tccaattacc agcacattac caatttcgaa tggtgcatca gtatactggt tgaattgacc    480
agactcgagg ggggccccag cccaggctac tacactgttt tcgatcgcga caataatcgg    540
gttagcttcg ctaatgcagt agtgctgggc cccgggccag ggcactccgg tctggtgacg    600
ttccaggcct tcatcgatgt aatgagccgc gagactacgg acaccgacac cgctgatggc    660
cccgggcctg gtctggatct tgcagccctg gaggatgtgt ccgctaactg tttgactgag    720
acactggagg acaagaacga gggcgtcgga ccagggcctg gtgtcctttc tttcgtcggt    780
cagacaaggg tgttgatgat caatggagaa gaggtggaag agaccgaatt gatgggaggc    840
ccagggcccg gcgaggttag cggcctggaa cagctggaga gtattatcaa ttttgaaaag    900
ctgaccgagt ggacaagctc caatgtaggc ggacctggac ccgggatgac agagcagcag    960
tggaattttg ccggtattga agctgcagcc agtgctatcc aaggcaacgt aacgagtatt    1020
cacagcctgc tcgacgacta caaagacgac gacgacaagg gcagtgacta taaggaccat    1080
gatggtgact ataaggacca cgacatcatg ctcatcccaa tcgctgtcgg aggtgctctg    1140
gccggtctcg tattgatcgt tctgatcgct tatttgatcg ggaggaaacg ctgtttctgt    1200
taa                                                                  1203

<210> SEQ ID NO 17
<211> LENGTH: 1215
<212> TYPE: DNA
<213> ORGANISM: Artificial Sequence
```

<220> FEATURE:
<223> OTHER INFORMATION: MHC-I nucleic acid for MHC-II presentation
      (sorting endosome target)

<400> SEQUENCE: 17

```
atgctgctgc tgccattcca gctcttggcc gtgctgttcc ccggggggaa ttctgaggat      60
aagatcaccc agtatgaaaa atccttgtat tattgtagct ttctggaagc cctggtgcga     120
gatgtgtgta taggcccagg gccggggtgt gttgattgcc tcgacaggac aaataccgcc     180
caggtaatgg ttggcaaatg cgcactcgca tatcaactct acggaccagg acccggcgtg     240
gtaaaggctt atctgccagt taacgagagc tttgccttca ccgcagacct gcgctccaat     300
actggtggtc aagggcccgg accaggtaat atcctcgccg tgagcttcgc ccctctggtc     360
cagctgagta aaaatgacaa tggtactcct gatagtgtag gcggacccgg tccgggtcag     420
tccaattacc agcacattac caatttcgaa tggtgcatca gtatactggt tgaattgacc     480
agactcgagg ggggcccagg cccaggctac tacactgttt tcgatcgcga caataatcgg     540
gttagcttcg ctaatgcagt agtgctgggc cccgggccag gcactccgg tctggtgacg      600
ttccaggcct tcatcgatgt aatgagccgc gagactacgg acaccgacac cgctgatggc     660
cccgggcctg gtctggatct tgcagccctg gaggatgtgt ccgctaactg tttgactgag     720
acactggagg acaagaacga gggcgtcgga ccagggcctg gtgtcctttc tttcgtcggt     780
cagacaaggg tgttgatgat caatggagaa gaggtggaag agaccgaatt gatgggaggc     840
ccagggcccg gcgaggttag cggcctggaa cagctggaga gtattatcaa ttttgaaaag     900
ctgaccgagt ggacaagctc caatgtaggc ggacctggac ccgggatgac agagcagcag     960
tggaattttg ccggtattga agctgcagcc agtgctatcc aaggcaacgt aacgagtatt    1020
cacagcctgc tcgacgacta caaagacgac gacgacaagg gcagtgacta taaggaccat    1080
gatggtgact ataaggacca cgacatcatg ctcatcccaa tcgctgtcgg aggtgctctg    1140
gccggtctcg tattgatcgt tctgatcgct tatttgatcg ggaagaagca ctgctcatat    1200
caggacatcc tgtga                                                     1215
```

<210> SEQ ID NO 18
<211> LENGTH: 405
<212> TYPE: PRT
<213> ORGANISM: Artificial Sequence
<220> FEATURE:
<223> OTHER INFORMATION: MHC-I polypeptide for MHC-II presentation
      (lysosomal target)

<400> SEQUENCE: 18

```
Met Leu Leu Leu Pro Phe Gln Leu Leu Ala Val Leu Phe Pro Gly Gly
1               5                   10                  15

Asn Ser Glu Asp Lys Ile Thr Gln Tyr Glu Lys Ser Leu Tyr Tyr Cys
            20                  25                  30

Ser Phe Leu Glu Ala Leu Val Arg Asp Val Cys Ile G

Ala Val Ser Phe Ala Pro Leu Val Gln Leu Ser Lys Asn Asp Asn Gly
            115                 120                 125

Thr Pro Asp Ser Val Gly Gly Pro Gly Pro Gly Gln Ser Asn Tyr Gln
    130                 135                 140

His Ile Thr Asn Phe Glu Trp Cys Ile Ser Ile Leu Val Glu Leu Thr
145                 150                 155                 160

Arg Leu Glu Gly Gly Pro Gly Pro Gly Tyr Tyr Thr Val Phe Asp Arg
                165                 170                 175

Asp Asn Asn Arg Val Ser Phe Ala Asn Ala Val Val Leu Gly Pro Gly
                180                 185                 190

Pro Gly His Ser Gly Leu Val Thr Phe Gln Ala Phe Ile Asp Val Met
            195                 200                 205

Ser Arg Glu Thr Thr Asp Thr Asp Thr Ala Asp Gly Pro Gly Pro Gly
            210                 215                 220

Leu Asp Leu Ala Ala Leu Glu Asp Val Ser Ala Asn Cys Leu Thr Glu
225                 230                 235                 240

Thr Leu Glu Asp Lys Asn Glu Gly Val Gly Pro Gly Pro Gly Val Leu
                245                 250                 255

Ser Phe Val Gly Gln Thr Arg Val Leu Met Ile Asn Gly Glu Glu Val
            260                 265                 270

Glu Glu Thr Glu Leu Met Gly Gly Pro Gly Pro Gly Glu Val Ser Gly
            275                 280                 285

Leu Glu Gln Leu Glu Ser Ile Ile Asn Phe Glu Lys Leu Thr Glu Trp
            290                 295                 300

Thr Ser Ser Asn Val Gly Gly Pro Gly Pro Gly Met Thr Glu Gln Gln
305                 310                 315                 320

Trp Asn Phe Ala Gly Ile Glu Ala Ala Ala Ser Ala Ile Gln Gly Asn
                325                 330                 335

Val Thr Ser Ile His Ser Leu Leu Asp Asp Tyr Lys Asp Asp Asp Asp
            340                 345                 350

Lys Gly Ser Asp Tyr Lys Asp His Asp Gly Asp Tyr Lys Asp His Asp
            355                 360                 365

Ile Met Leu Ile Pro Ile Ala Val Gly Gly Ala Leu Ala Gly Leu Val
            370                 375                 380

Leu Ile Val Leu Ile Ala Tyr Leu Ile Gly Arg Lys Arg Ser His Ala
385                 390                 395                 400

Gly Tyr Gln Thr Ile
            405

<210> SEQ ID NO 19
<211> LENGTH: 400
<212> TYPE: PRT
<213> ORGANISM: Artificial Sequence
<220> FEATURE:
<223> OTHER INFORMATION: MHC-I polypeptide for MHC-II presentation
      (recycling endosome target)

<400

```
            50                  55                  60
Gly Lys Cys Ala Leu Ala Tyr Gln Leu Tyr Gly Pro Gly Pro Gly Val
 65                  70                  75                  80

Val Lys Ala Tyr Leu Pro Val Asn Glu Ser Phe Ala Phe Thr Ala Asp
                 85                  90                  95

Leu Arg Ser Asn Thr Gly Gly Gln Gly Pro Gly Pro Gly Asn Ile Leu
                100                 105                 110

Ala Val Ser Phe Ala Pro Leu Val Gln Leu Ser Lys Asn Asp Asn Gly
            115                 120                 125

Thr Pro Asp Ser Val Gly Gly Pro Gly Pro Gly Gln Ser Asn Tyr Gln
            130                 135                 140

His Ile Thr Asn Phe Glu Trp Cys Ile Ser Ile Leu Val Glu Leu Thr
145                 150                 155                 160

Arg Leu Glu Gly Gly Pro Gly Pro Gly Tyr Tyr Thr Val Phe Asp Arg
                165                 170                 175

Asp Asn Asn Arg Val Ser Phe Ala Asn Ala Val Val Leu Gly Pro Gly
                180                 185                 190

Pro Gly His Ser Gly Leu Val Thr Phe Gln Ala Phe Ile Asp Val Met
            195                 200                 205

Ser Arg Glu Thr Thr Asp Thr Asp Thr Ala Asp Gly Pro Gly Pro Gly
210                 215                 220

Leu Asp Leu Ala Ala Leu Glu Asp Val Ser Ala Asn Cys Leu Thr Glu
225                 230                 235                 240

Thr Leu Glu Asp Lys Asn Glu Gly Val Gly Pro Gly Pro Gly Val Leu
                245                 250                 255

Ser Phe Val Gly Gln Thr Arg Val Leu Met Ile Asn Gly Glu Glu Val
            260                 265                 270

Glu Glu Thr Glu Leu Met Gly Gly Pro Gly Pro Gly Val Ser Gly
            275                 280                 285

Leu Glu Gln Leu Glu Ser Ile Ile Asn Phe Glu Lys Leu Thr Glu Trp
            290                 295                 300

Thr Ser Ser Asn Val Gly Gly Pro Gly Pro Gly Met Thr Glu Gln Gln
305                 310                 315                 320

Trp Asn Phe Ala Gly Ile Glu Ala Ala Ala Ser Ala Ile Gln Gly Asn
                325                 330                 335

Val Thr Ser Ile His Ser Leu Leu Asp Asp Tyr Lys Asp Asp Asp
            340                 345                 350

Lys Gly Ser Asp Tyr Lys Asp His Asp Gly Asp Tyr Lys Asp His Asp
            355                 360                 365

Ile Met Leu Ile Pro Ile Ala Val Gly Gly Ala Leu Ala Gly Leu Val
            370                 375                 380

Leu Ile Val Leu Ile Ala Tyr Leu Ile Gly Arg Lys Arg Cys Phe Cys
385                 390                 395                 400
```

<210> SEQ ID NO 20
<211> LENGTH: 404
<212> TYPE: PRT
<213> ORGANISM: Artificial Sequence
<220> FEATURE:
<223> OTHER INFORMATION: MHC-I polypeptide for MHC-II presentation
      (sorting endosome target)

<400> SEQUENCE: 20

```
Met Leu Leu Leu Pro Phe Gln Leu Leu Ala Val Leu Phe Pro Gly Gly
 1               5                  10                  15
```

```
Asn Ser Glu Asp Lys Ile Thr Gln Tyr Glu Lys Ser Leu Tyr Tyr Cys
             20                  25                  30

Ser Phe Leu Glu Ala Leu Val Arg Asp Val Cys Ile Gly Pro Gly Pro
         35                  40                  45

Gly Cys Val Asp Cys Leu Asp Arg Thr Asn Thr Ala Gln Val Met Val
     50                  55                  60

Gly Lys Cys Ala Leu Ala Tyr Gln Leu Tyr Gly Pro Gly Pro Gly Val
65                  70                  75                  80

Val Lys Ala Tyr Leu Pro Val Asn Glu Ser Phe Ala Phe Thr Ala Asp
                 85                  90                  95

Leu Arg Ser Asn Thr Gly Gly Gln Gly Pro Gly Pro Gly Asn Ile Leu
             100                 105                 110

Ala Val Ser Phe Ala Pro Leu Val Gln Leu Ser Lys Asn Asp Asn Gly
         115                 120                 125

Thr Pro Asp Ser Val Gly Gly Pro Gly Pro Gly Gln Ser Asn Tyr Gln
    130                 135                 140

His Ile Thr Asn Phe Glu Trp Cys Ile Ser Ile Leu Val Glu Leu Thr
145                 150                 155                 160

Arg Leu Glu Gly Gly Pro Gly Pro Gly Tyr Tyr Thr Val Phe Asp Arg
                165                 170                 175

Asp Asn Asn Arg Val Ser Phe Ala Asn Ala Val Val Leu Gly Pro Gly
            180                 185                 190

Pro Gly His Ser Gly Leu Val Thr Phe Gln Ala Phe Ile Asp Val Met
        195                 200                 205

Ser Arg Glu Thr Thr Asp Thr Asp Thr Ala Asp Gly Pro Gly Pro Gly
210                 215                 220

Leu Asp Leu Ala Ala Leu Glu Asp Val Ser Ala Asn Cys Leu Thr Glu
225                 230                 235                 240

Thr Leu Glu Asp Lys Asn Glu Gly Val Gly Pro Gly Pro Gly Val Leu
                245                 250                 255

Ser Phe Val Gly Gln Thr Arg Val Leu Met Ile Asn Gly Glu Glu Val
            260                 265                 270

Glu Glu Thr Glu Leu Met Gly Gly Pro Gly Pro Gly Glu Val Ser Gly
        275                 280                 285

Leu Glu Gln Leu Glu Ser Ile Ile Asn Phe Glu Lys Leu Thr Glu Trp
290                 295                 300

Thr Ser Ser Asn Val Gly Gly Pro Gly Pro Gly Met Thr Glu Gln Gln
305                 310                 315                 320

Trp Asn Phe Ala Gly Ile Glu Ala Ala Ala Ser Ala Ile Gln Gly Asn
                325                 330                 335

Val Thr Ser Ile His Ser Leu Leu Asp Asp Tyr Lys Asp Asp Asp Asp
            340                 345                 350

Lys Gly Ser Asp Tyr Lys Asp His Asp Gly Asp Tyr Lys Asp His Asp
        355                 360                 365

Ile Met Leu Ile Pro Ile Ala Val Gly Gly Ala Leu Ala Gly Leu Val
    370                 375                 380

Leu Ile Val Leu Ile Ala Tyr Leu Ile Gly Lys Lys His Cys Ser Tyr
385                 390                 395                 400

Gln Asp Ile Leu
```

<210> SEQ ID NO 21
<211> LENGTH: 2712
<212> TYPE: DNA
<213> ORGANISM: Artificial Sequence
<220> FEATURE:
<223> OTHER INFORMATION: MHC-II nucleic acid for MHC-II presentation
(lysosomal target)

<400> SEQUENCE: 21

| | |
|---|---|
| atgctgctgc tgcccttcca gttgctggct gtcctctttc ccggcggcaa ctccgaggca | 60 |
| ctgcaggcct accacctgga tcctcaatgc tggggcgtga acgtgcagcc ctactccggg | 120 |
| agccctgcca atgtcgcagt ttatacagct ttggtagagc ctcatggcag aatcatgggt | 180 |
| ctcgatcttc cagacggcgg gcatctcacg ggccctggtc cgggtgatac cgatgaagct | 240 |
| gaggatccag agaaaatgct tgccaacttt gagtccggaa agcataagta tcgacagaca | 300 |
| gccatgttta ccgccaccat gccaccagcc gtcgagagac tggctagatc ctacctgagg | 360 |
| agacctgctg tggtgtacgg cccaggcccg ggcaggcgt atctgttgca gaacacagct | 420 |
| ctcgaagtct tcatggcaaa tcgcacttct gttatgttca actttcctga caagccacg | 480 |
| gtgaagaaag tggtatattc ccttcccagg gttggggtcg gcacaagcta tgggctcccc | 540 |
| caagcagggc caggaccagg gaagattgag cccgatatga tgtcaatgga acatagcttc | 600 |
| gaaacggcat cccatgacgg agaggctggc ccctccccag aagtgttgca gggccctgga | 660 |
| cctggcaagg ttctgatggc atccacttcc tacttgccct cccaggtcac tgagatgttt | 720 |
| aaccagggaa gggcatttgc agcagtcaga ttgcctttt gtggacacaa aaacatctgt | 780 |
| agcctgacaa caatccagaa gattccacga ctgctcgtag acctggacc tggcatgccc | 840 |
| gcagccgagt tggcactcag cgccttcctc gtcctcgtct ttttgtgggt gcattctttg | 900 |
| cgccgccttc tcgaatgctt ctatgtatct gtattctcta acgccgccat ccatgttgta | 960 |
| caatactgtt tcggcctcgt gtactacggt cctggccccg gactcctcga gctcctgcac | 1020 |
| tgcccacttg gtcactgtca tctgtgttcc gagccgatgt tcacgtttgt gtaccccaca | 1080 |
| attttcccac tcagagagac tcctatggct gggcttcacc agcggcgaac gtccatcggc | 1140 |
| ttcgtggcct attgtggccc aggcccaggc gcccattttc gccttgtgtc aaaggaaaag | 1200 |
| atgccgtggg acagcatcaa actgaccttc gaggcaaccg gacctaggca catgagcttc | 1260 |
| tatgtgcgca cccacaaggg ttctacccctc agccagtggt cactgggtaa tggaattcca | 1320 |
| gtgggccctg gaccgggagg taggacacag caaatgctca ttcccgcttg caacaggtt | 1380 |
| acacctatgg ctccagccgc cgccacattg acattgagg gcatggccgg atctcagagg | 1440 |
| ctgggcgact ggggaaagat gattccccac agcaaccatt acaactccgt tgggccaggc | 1500 |
| cctggtgaac ttcagctcgt ccagttggag ggcggggcg gcagcgggac atatagagtc | 1560 |
| gggaacgccc aaccatcact cgccgattgt ctggacgccg gggatcttgc ccagcgcctc | 1620 |
| agagagcatg cgcgccgaagt gcccacagaa cctaaagagg gaccaggacc cggcgagctt | 1680 |
| gaaaagttcc gcaagtctga ggagggtaag caacggccg ccgccccag tgccgccagc | 1740 |
| tcaccagcag acgtccagag cctgaagaag gccatgtcct ctctgcagaa tgacagggac | 1800 |
| cggctgctca aggaactgaa gaatctgggc cccggccctg ggggcaaaca cgaccgggat | 1860 |
| ctgctgattg ggaccgctaa gcacggtctg aatcgaactg attactacat catgaatgga | 1920 |
| cctcagctct catttctcga cgcatacaga aactacgccc agcataaacg aactgacaca | 1980 |
| caggctcctg gcagtggacc cggccctgga attctcgagg tggacaaaag cggccctatt | 2040 |
| actctcttgg tgcagggaca catggaggga gaggtctggg ggctgtctac tcatccatac | 2100 |
| ctgcccatat cgccaccgt tagtgatgac aaaactctca gaatttggga cttgtccccg | 2160 |
| tccggccccag gtcctggtat gctcaccgct cggcttttgc tcccaaggct gctctgtctt | 2220 |

-continued

```
cagggcagga ccactagtta ttcaacagcc gcagtactgc ccaatccaat cccaaacccc   2280
gagatttgtt ataataagtt gtttatcaat aacgagtggc acgacgccgt cggcccgggc   2340
cctggggaag ttagtggtct ggaacagctg gaatctatca ttaatttcga gaaactgaca   2400
gaatggactt ccagcaacgt cgggggacca ggtcctggaa tgacagagca gcagtggaat   2460
tttgccggaa ttgaggccgc tgcatctgcc atccaaggaa atgtgacatc cattcactcc   2520
ctcctcgatg attacaagga cgacgacgac aagggaagtg actacaaaga ccacgacggg   2580
gactacaagg accacgacat tatgctgatc cccatcgccg tgggcggggc cctggccggc   2640
ctcgtgctga tcgtccttat cgcctacctc atcggcagga agaggagtca cgcaggctac   2700
cagactatct ag                                                       2712
```

<210> SEQ ID NO 22
<211> LENGTH: 2697
<212> TYPE: DNA
<213> ORGANISM: Artificial Sequence
<220> FEATURE:
<223> OTHER INFORMATION: MHC-II nucleic acid for MHC-II presentation
      (recycling endosome target)

<400> SEQUENCE: 22

```
atgctgctgc tgcccttcca gttgctggct gtcctctttc ccggcggcaa ctccgaggca    60
ctgcaggcct accacctgga tcctcaatgc tggggcgtga acgtgcagcc ctactccggg   120
agccctgcca atgtcgcagt ttatacagct ttggtagagc ctcatggcag aatcatgggt   180
ctcgatcttc cagacggcgg gcatctcacg ggccctggtc cgggtgatac cgatgaagct   240
gaggatccag agaaaatgct tgccaacttt gagtccggaa agcataagta tcgacagaca   300
gccatgttta ccgccaccat gccaccagcc gtcgagagac tggctagatc ctacctgagg   360
agacctgctg tggtgtacgg cccaggcccg ggcaggcggt atctgttgca gaacacagct   420
ctcgaagtct tcatggcaaa tcgcacttct gttatgttca actttcctga caagccacg    480 gtgaagaaag tggtatattc ccttcccagg gttggggtcg gcacaagcta tgggctcccc   540
caagcagggc caggaccagg gaagattgag cccgatatga tgtcaatgga acatagcttc   600
gaaacggcat cccatgacgg agaggctggc ccctccccag aagtgttgca gggccctgga   660
cctggcaagg ttctgatggc atccacttcc tacttgccct cccaggtcac tgagatgttt   720
aaccagggaa gggcatttgc agcagtcaga ttgccttttt gtggacacaa aaacatctgt   780
agcctgacaa caatccagaa gattccacga ctgctcgtag acctggacc tggcatgccc   840 gcagccgagt tggcactcag cgccttcctc gtcctcgtct ttttgtgggt gcattctttg   900
cgccgccttc tcgaatgctt ctatgtatct gtattctcta acgccgccat ccatgttgta   960
caatactgtt tcggcctcgt gtactacggt cctggccccg gactcctcga gctcctgcac  1020
tgcccacttg gtcactgtca tctgtgttcc gagccgatgt tcacgtttgt gtacccacca  1080
attttcccac tcagagagac tcctatggct gggcttcacc agcggcgaac gtccatcggc  1140
ttcgtggcct attgtggccc aggcccaggc gcccattttc gccttgtgtc aaaggaaaag  1200
atgccgtggg acagcatcaa actgaccttc gaggcaaccg gacctaggca catgagcttc  1260
tatgtgcgca cccacaaggg ttctaccctc agccagtggt cactgggtaa tggaattcca  1320
gtgggccctg gaccgggagg taggacacag caaatgctca ttcccgcttg gcaacaggtt  1380
acacctatgg ctccagccgc cgccacattg acattcgagg gcatggccgg atctcagagg  1440
ctgggcgact ggggaaagat gattccccac agcaaccatt acaactccgt tgggccaggc  1500
```

-continued

```
cctggtgaac ttcagctcgt ccagttggag ggcgggggcg gcagcgggac atatagagtc    1560
gggaacgccc aaccatcact cgccgattgt ctggacgccg gggatcttgc ccagcgcctc    1620
agagagcatg gcgccgaagt gcccacagaa cctaaagagg gaccaggacc cggcgagctt    1680
gaaaagttcc gcaagtctga ggagggtaag caacgggccg ccgcccccag tgccgccagc    1740
tcaccagcag acgtccagag cctgaagaag gccatgtcct ctctgcagaa tgacagggac    1800
cggctgctca aggaactgaa gaatctgggc cccggccctg ggggcaaaca cgaccgggat    1860
ctgctgattg ggaccgctaa gcacggtctg aatcgaactg attactacat catgaatgga    1920
cctcagctct catttctcga cgcatacaga aactacgccc agcataaacg aactgacaca    1980
caggctcctg gcagtggacc cggccctgga attctcgagg tggacaaaag cggccctatt    2040
actctcttgg tgcagggaca catggaggga gaggtctggg ggctgtctac tcatccatac    2100
ctgcccatat gcgccaccgt tagtgatgac aaaactctca gaatttggga cttgtccccg    2160
tccggcccag gtcctggtat gctcaccgct cggcttttgc tcccaaggct gctctgtctt    2220
cagggcagga ccactagtta ttcaacagcc gcagtactgc ccaatccaat cccaaacccc    2280
gagatttgtt ataataagtt gtttatcaat aacgagtggc acgacgccgt cggcccgggc    2340
cctggggaag ttagtggtct ggaacagctg gaatctatca ttaatttcga gaaactgaca    2400
gaatggactt ccagcaacgt cggggggacca ggtcctggaa tgacagagca gcagtggaat    2460
tttgccggaa ttgaggccgc tgcatctgcc atccaaggaa atgtgacatc cattcactcc    2520
ctcctcgatg attacaagga cgacgacgac aagggaagtg actacaaaga ccacgacggg    2580
gactacaagg accacgacat tatgctgatc cccatcgccg tgggcggggc cctggccggc    2640
ctcgtgctga tcgtccttat cgcctacctc atcggcagga acgctgtttt ctgttaa      2697
```

<210> SEQ ID NO 23
<211> LENGTH: 2709
<212> TYPE: DNA
<213> ORGANISM: Artificial Sequence
<220> FEATURE:
<223> OTHER INFORMATION: MHC-II nucleic acid for MHC-II presentation
(sorting endosome target)

<400> SEQUENCE: 23

```
atgctgctgc tgcccttcca gttgctggct gtcctctttc ccggcggcaa ctccgaggca     60
ctgcaggcct accacctgga tcctcaatgc tggggcgtga acgtgcagcc ctactccggg    120
agccctgcca atgtcgcagt ttatacagct ttggtagagc tcatggcag aatcatgggt    180 ctcgatcttc cagacggcgg gcatctcacg ggccctggtc cgggtgatac cgatgaagct    240
gaggatccag agaaaatgct tgccaacttt gagtccggaa agcataagta tcgacagaca    300
gccatgttta ccgccaccat gccaccagcc gtcgagagac tggctagatc ctacctgagg    360
agacctgctg tggtgtacgg cccaggcccg ggcaggcggt atctgttgca gaacacagct    420
ctcgaagtct tcatggcaaa tcgcacttct gttatgttca actttcctga caagccacg    480 gtgaagaaag tggtatattc ccttcccagg gttggggtcg gcacaagcta tgggctcccc    540
caagcagggc caggaccagg gaagattgag cccgatatga tgtcaatgga acatagcttc    600
gaaacggcat cccatgacgg agaggctggc ccctccccag aagtgttgca gggccctgga    660
cctggcaagg ttctgatggc atccacttcc tacttgccct cccaggtcac tgagatgttt    720
aaccagggaa gggcatttgc agcagtcaga ttgccttttt gtggacacaa aaacatctgt    780
agcctgacaa caatccagaa gattccacga ctgctcgtag gacctggacc tggcatgccc    840
```

-continued

```
gcagccgagt tggcactcag cgccttcctc gtcctcgtct ttttgtgggt gcattctttg    900
cgccgccttc tcgaatgctt ctatgtatct gtattctcta acgccgccat ccatgttgta    960
caatactgtt tcggcctcgt gtactacggt cctggccccg actcctcga gctcctgcac   1020
tgcccacttg gtcactgtca tctgtgttcc gagccgatgt tcacgtttgt gtaccccaca   1080
attttcccac tcagagagac tcctatggct gggcttcacc agcggcgaac gtccatcggc   1140
ttcgtggcct attgtgggcc aggcccaggc gcccattttc gccttgtgtc aaaggaaaag   1200
atgccgtggg acagcatcaa actgaccttc gaggcaaccg gacctaggca catgagcttc   1260
tatgtgcgca cccacaaggg ttctaccctc agccagtggt cactgggtaa tggaattcca   1320
gtgggccctg gaccgggagg taggacacag caaatgctca ttcccgcttg caacaggtt   1380
acacctatgg ctccagccgc cgccacattg acattcgagg gcatggccgg atctcagagg   1440
ctgggcgact ggggaaagat gattccccac agcaaccatt acaactccgt tgggccaggc   1500
cctggtgaac ttcagctcgt ccagttggag ggcgggggcg gcagcgggac atatagagtc   1560
gggaacgccc aaccatcact cgccgattgt ctggacgccg gggatcttgc ccagcgcctc   1620
agagagcatg gcgccgaagt gcccacagaa cctaaagagg gaccaggacc cggcgagctt   1680
gaaaagttcc gcaagtctga ggagggtaag caacgggccg ccgcccccag tgccgccagc   1740
tcaccagcag acgtccagag cctgaagaag gccatgtcct ctctgcagaa tgacagggac   1800
cggctgctca aggaactgaa gaatctgggc cccggccctg ggggcaaaca cgaccgggat   1860
ctgctgattg ggaccgctaa gcacggtctg aatcgaactg attactacat catgaatgga   1920
cctcagctct catttctcga cgcatacaga aactacgccc agcataaacg aactgacaca   1980
caggctcctg gcagtggacc cggccctgga attctcgagg tggacaaaag cggccctatt   2040
actctcttgg tgcagggaca catggaggga gaggtctggg ggctgtctac tcatccatac   2100
ctgcccatat gcgccaccgt tagtgatgac aaaaactctca gaatttggga cttgtccccg   2160
tccggcccag gtcctggtat gctcaccgct cggcttttgc tcccaaggct gctctgtctt   2220
cagggcagga ccactagtta ttcaacagcc gcagtactgc ccaatccaat cccaaacccc   2280
gagatttgtt ataataagtt gtttatcaat aacgagtggc acgacgccgt cggcccgggc   2340
cctggggaag ttagtggtct ggaacagctg gaatctatca ttaatttcga gaaactgaca   2400
gaatggactt ccagcaacgt cgggggacca ggtcctggaa tgacagagca gcagtggaat   2460
tttgccggaa ttgaggccgc tgcatctgcc atccaaggaa atgtgacatc cattcactcc   2520
ctcctcgatg attacaagga cgacgacgac aagggaagtg actacaaaga ccacgacggg   2580
gactacaagg accacgacat tatgctgatc ccatcgccg tgggcggggc cctggccggc   2640
ctcgtgctga tcgtccttat cgcctacctc atcggcaaga agcactgctc atatcaggac   2700
atcctgtga                                                             2709
```

<210> SEQ ID NO 24
<211> LENGTH: 903
<212> TYPE: PRT
<213> ORGANISM: Artificial Sequence
<220> FEATURE:
<223> OTHER INFORMATION: MHC-II polypeptide for MHC-II presentation
   (lysosomal target)

<400> SEQUENCE: 24

Met Leu Leu Leu Pro Phe Gln Leu Leu Ala Val Leu Phe Pro Gly Gly
1               5                   10                  15

```
Asn Ser Glu Ala Leu Gln Ala Tyr His Leu Asp Pro Gln Cys Trp Gly
             20                  25                  30

Val Asn Val Gln Pro Tyr Ser Gly Ser Pro Ala Asn Val Ala Val Tyr
             35                  40                  45

Thr Ala Leu Val Glu Pro His Gly Arg Ile Met Gly Leu Asp Leu Pro
 50                  55                  60

Asp Gly Gly His Leu Thr Gly Pro Gly Pro Gly Asp Thr Asp Glu Ala
 65                  70                  75                  80

Glu Asp Pro Glu Lys Met Leu Ala Asn Phe Glu Ser Gly Lys His Lys
             85                  90                  95

Tyr Arg Gln Thr Ala Met Phe Thr Ala Thr Met Pro Pro Ala Val Glu
            100                 105                 110

Arg Leu Ala Arg Ser Tyr Leu Arg Arg Pro Ala Val Val Tyr Gly Pro
            115                 120                 125

Gly Pro Gly Arg Arg Tyr Leu Leu Gln Asn Thr Ala Leu Glu Val Phe
            130                 135                 140

Met Ala Asn Arg Thr Ser Val Met Phe Asn Phe Pro Glu Gln Ala Thr
145                 150                 155                 160

Val Lys Lys Val Val Tyr Ser Leu Pro Arg Val Gly Val Gly Thr Ser
            165                 170                 175

Tyr Gly Leu Pro Gln Ala Gly Pro Gly Pro Gly Lys Ile Glu Pro Asp
            180                 185                 190

Met Met Ser Met Glu His Ser Phe Glu Thr Ala Ser His Asp Gly Glu
            195                 200                 205

Ala Gly Pro Ser Pro Glu Val Leu Gln Gly Pro Gly Pro Gly Lys Val
210                 215                 220

Leu Met Ala Ser Thr Ser Tyr Leu Pro Ser Gln Val Thr Glu Met Phe
225                 230                 235                 240

Asn Gln Gly Arg Ala Phe Ala Ala Val Arg Leu Pro Phe Cys Gly His
            245                 250                 255

Lys Asn Ile Cys Ser Leu Thr Thr Ile Gln Lys Ile Pro Arg Leu Leu
            260                 265                 270

Val Gly Pro Gly Pro Gly Met Pro Ala Ala Glu Leu Ala Leu Ser Ala
            275                 280                 285

Phe Leu Val Leu Val Phe Leu Trp Val His Ser Leu Arg Arg Leu Leu
290                 295                 300

Glu Cys Phe Tyr Val Ser Val Phe Ser Asn Ala Ala Ile His Val Val
305                 310                 315                 320

Gln Tyr Cys Phe Gly Leu Val Tyr Tyr Gly Pro Gly Pro Gly Leu Leu
            325                 330                 335

Glu Leu Leu His Cys Pro Leu Gly His Cys His Leu Cys Ser Glu Pro
            340                 345                 350

Met Phe Thr Phe Val Tyr Pro Thr Ile Phe Pro Leu Arg Glu Thr Pro
            355                 360                 365

Met Ala Gly Leu His Gln Arg Thr Ser Ile Gly Phe Val Ala Tyr
            370                 375                 380

Cys Gly Pro Gly Pro Gly Ala His Phe Arg Leu Val Ser Lys Glu Lys
385                 390                 395                 400

Met Pro Trp Asp Ser Ile Lys Leu Thr Phe Glu Ala Thr Gly Pro Arg
                405                 410                 415

His Met Ser Phe Tyr Val Arg Thr His Lys Gly Ser Thr Leu Ser Gln
            420                 425                 430

Trp Ser Leu Gly Asn Gly Ile Pro Val Gly Pro Gly Pro Gly Gly Arg
```

```
                435                 440                 445
Thr Gln Gln Met Leu Ile Pro Ala Trp Gln Gln Val Thr Pro Met Ala
450                 455                 460
Pro Ala Ala Ala Thr Leu Thr Phe Glu Gly Met Ala Gly Ser Gln Arg
465                 470                 475                 480
Leu Gly Asp Trp Gly Lys Met Ile Pro His Ser Asn His Tyr Asn Ser
                485                 490                 495
Val Gly Pro Gly Pro Gly Glu Leu Gln Leu Val Gln Leu Glu Gly Gly
                500                 505                 510
Gly Gly Ser Gly Thr Tyr Arg Val Gly Asn Ala Gln Pro Ser Leu Ala
                515                 520                 525
Asp Cys Leu Asp Ala Gly Asp Leu Ala Gln Arg Leu Arg Glu His Gly
                530                 535                 540
Ala Glu Val Pro Thr Glu Pro Lys Glu Gly Pro Gly Pro Gly Glu Leu
545                 550                 555                 560
Glu Lys Phe Arg Lys Ser Glu Glu Gly Lys Gln Arg Ala Ala Ala Pro
                565                 570                 575
Ser Ala Ala Ser Ser Pro Ala Asp Val Gln Ser Leu Lys Lys Ala Met
                580                 585                 590
Ser Ser Leu Gln Asn Asp Arg Asp Arg Leu Leu Lys Glu Leu Lys Asn
                595                 600                 605
Leu Gly Pro Gly Pro Gly Gly Lys His Asp Arg Asp Leu Leu Ile Gly
                610                 615                 620
Thr Ala Lys His Gly Leu Asn Arg Thr Asp Tyr Tyr Ile Met Asn Gly
625                 630                 635                 640
Pro Gln Leu Ser Phe Leu Asp Ala Tyr Arg Asn Tyr Ala Gln His Lys
                645                 650                 655
Arg Thr Asp Thr Gln Ala Pro Gly Ser Gly Pro Gly Pro Gly Ile Leu
                660                 665                 670
Glu Val Asp Lys Ser Gly Pro Ile Thr Leu Leu Val Gln Gly His Met
                675                 680                 685
Glu Gly Glu Val Trp Gly Leu Ser Thr His Pro Tyr Leu Pro Ile Cys
                690                 695                 700
Ala Thr Val Ser Asp Asp Lys Thr Leu Arg Ile Trp Asp Leu Ser Pro
705                 710                 715                 720
Ser Gly Pro Gly Pro Gly Met Leu Thr Ala Arg Leu Leu Leu Pro Arg
                725                 730                 735
Leu Leu Cys Leu Gln Gly Arg Thr Thr Ser Tyr Ser Thr Ala Ala Val
                740                 745                 750
Leu Pro Asn Pro Ile Pro Asn Pro Glu Ile Cys Tyr Asn Lys Leu Phe
                755                 760                 765
Ile Asn Asn Glu Trp His Asp Ala Val Gly Pro Gly Pro Gly Glu Val
                770                 775                 780
Ser Gly Leu Glu Gln Leu Glu Ser Ile Ile Asn Phe Glu Lys Leu Thr
785                 790                 795                 800
Glu Trp Thr Ser Ser Asn Val Gly Gly Pro Gly Pro Gly Met Thr Glu
                805                 810                 815
Gln Gln Trp Asn Phe Ala Gly Ile Glu Ala Ala Ala Ser Ala Ile Gln
                820                 825                 830
Gly Asn Val Thr Ser Ile His Ser Leu Leu Asp Asp Tyr Lys Asp Asp
                835                 840                 845
Asp Asp Lys Gly Ser Asp Tyr Lys Asp His Asp Gly Asp Tyr Lys Asp
850                 855                 860
```

```
His Asp Ile Met Leu Ile Pro Ile Ala Val Gly Gly Ala Leu Ala Gly
865                 870                 875                 880

Leu Val Leu Ile Val Leu Ile Ala Tyr Leu Ile Gly Arg Lys Arg Ser
            885                 890                 895

His Ala Gly Tyr Gln Thr Ile
            900

<210> SEQ ID NO 25
<211> LENGTH: 898
<212> TYPE: PRT
<213> ORGANISM: Artificial Sequence
<220> FEATURE:
<223> OTHER INFORMATION: MHC-II polypeptide for MHC-II presentation
      (recycling endosome target)

<400> SEQUENCE: 25

Met Leu Leu Leu Pro Phe Gln Leu Leu Ala Val Leu Phe Pro Gly Gly
1               5                   10                  15

Asn Ser Glu Ala Leu Gln Ala Tyr His Leu Asp Pro Gln Cys Trp Gly
            20                  25                  30

Val Asn Val Gln Pro Tyr Ser Gly Ser Pro Ala Asn Val Ala Val Tyr
        35                  40                  45

Thr Ala Leu Val Glu Pro His Gly Arg Ile Met Gly Leu Asp Leu Pro
    50                  55                  60

Asp Gly Gly His Leu Thr Gly Pro Gly Pro Gly Asp Thr Asp Glu Ala
65                  70                  75                  80

Glu Asp Pro Glu Lys Met Leu Ala Asn Phe Glu Ser Gly Lys His Lys
                85                  90                  95

Tyr Arg Gln Thr Ala Met Phe Thr Ala Thr Met Pro Pro Ala Val Glu
            100                 105                 110

Arg Leu Ala Arg Ser Tyr Leu Arg Arg Pro Ala Val Val Tyr Gly Pro
        115                 120                 125

Gly Pro Gly Arg Arg Tyr Leu Leu Gln Asn Thr Ala Leu Glu Val Phe
    130                 135                 140

Met Ala Asn Arg Thr Ser Val Met Phe Asn Phe Pro Glu Gln Ala Thr
145                 150                 155                 160

Val Lys Lys Val Val Tyr Ser Leu Pro Arg Val Gly Val Gly Thr Ser
                165                 170                 175

Tyr Gly Leu Pro Gln Ala Gly Pro Gly Pro Gly Lys Ile Glu Pro Asp
            180                 185                 190

Met Met Ser Met Glu His Ser Phe Glu Thr Ala Ser His Asp Gly Glu
        195                 200                 205

Ala Gly Pro Ser Pro Glu Val Leu Gln Gly Pro Gly Pro Gly Lys Val
    210                 215                 220

Leu Met Ala Ser Thr Ser Tyr Leu Pro Ser Gln Val Thr Glu Met Phe
225                 230                 235                 240

Asn Gln Gly Arg Ala Phe Ala Ala Val Arg Leu Pro Phe Cys Gly His
                245                 250                 255

Lys Asn Ile Cys Ser Leu Thr Thr Ile Gln Lys Ile Pro Arg Leu Leu
            260                 265                 270

Val Gly Pro Gly Pro Gly Met Pro Ala Ala Glu Leu Ala Leu Ser Ala
        275                 280                 285

Phe Leu Val Leu Val Phe Leu Trp Val His Ser Leu Arg Arg Leu Leu
    290                 295                 300

Glu Cys Phe Tyr Val Ser Val Phe Ser Asn Ala Ala Ile His Val Val
```

-continued

```
                305                 310                 315                 320
            Gln Tyr Cys Phe Gly Leu Val Tyr Tyr Gly Pro Gly Pro Gly Leu Leu
                            325                 330                 335
            Glu Leu Leu His Cys Pro Leu Gly His Cys His Leu Cys Ser Glu Pro
                            340                 345                 350
            Met Phe Thr Phe Val Tyr Pro Thr Ile Phe Pro Leu Arg Glu Thr Pro
                            355                 360                 365
            Met Ala Gly Leu His Gln Arg Arg Thr Ser Ile Gly Phe Val Ala Tyr
                            370                 375                 380
            Cys Gly Pro Gly Pro Gly Ala His Phe Arg Leu Val Ser Lys Glu Lys
            385                 390                 395                 400
            Met Pro Trp Asp Ser Ile Lys Leu Thr Phe Glu Ala Thr Gly Pro Arg
                            405                 410                 415
            His Met Ser Phe Tyr Val Arg Thr His Lys Gly Ser Thr Leu Ser Gln
                            420                 425                 430
            Trp Ser Leu Gly Asn Gly Ile Pro Val Gly Pro Gly Pro Gly Gly Arg
                            435                 440                 445
            Thr Gln Gln Met Leu Ile Pro Ala Trp Gln Gln Val Thr Pro Met Ala
                            450                 455                 460
            Pro Ala Ala Ala Thr Leu Thr Phe Glu Gly Met Ala Gly Ser Gln Arg
            465                 470                 475                 480
            Leu Gly Asp Trp Gly Lys Met Ile Pro His Ser Asn His Tyr Asn Ser
                            485                 490                 495
            Val Gly Pro Gly Pro Gly Glu Leu Gln Leu Val Gln Leu Glu Gly Gly
                            500                 505                 510
            Gly Gly Ser Gly Thr Tyr Arg Val Gly Asn Ala Gln Pro Ser Leu Ala
                            515                 520                 525
            Asp Cys Leu Asp Ala Gly Asp Leu Ala Gln Arg Leu Arg Glu His Gly
                            530                 535                 540
            Ala Glu Val Pro Thr Glu Pro Lys Glu Gly Pro Gly Pro Gly Glu Leu
            545                 550                 555                 560
            Glu Lys Phe Arg Lys Ser Glu Glu Gly Lys Gln Arg Ala Ala Ala Pro
                            565                 570                 575
            Ser Ala Ala Ser Ser Pro Ala Asp Val Gln Ser Leu Lys Lys Ala Met
                            580                 585                 590
            Ser Ser Leu Gln Asn Asp Arg Asp Arg Leu Leu Lys Glu Leu Lys Asn
                            595                 600                 605
            Leu Gly Pro Gly Pro Gly Gly Lys His Asp Arg Asp Leu Leu Ile Gly
                            610                 615                 620
            Thr Ala Lys His Gly Leu Asn Arg Thr Asp Tyr Tyr Ile Met Asn Gly
            625                 630                 635                 640
            Pro Gln Leu Ser Phe Leu Asp Ala Tyr Arg Asn Tyr Ala Gln His Lys
                            645                 650                 655
            Arg Thr Asp Thr Gln Ala Pro Gly Ser Gly Pro Gly Pro Gly Ile Leu
                            660                 665                 670
            Glu Val Asp Lys Ser Gly Pro Ile Thr Leu Leu Val Gln Gly His Met
                            675                 680                 685
            Glu Gly Glu Val Trp Gly Leu Ser Thr His Pro Tyr Leu Pro Ile Cys
                            690                 695                 700
            Ala Thr Val Ser Asp Asp Lys Thr Leu Arg Ile Trp Asp Leu Ser Pro
            705                 710                 715                 720
            Ser Gly Pro Gly Pro Gly Met Leu Thr Ala Arg Leu Leu Leu Pro Arg
                            725                 730                 735
```

```
Leu Leu Cys Leu Gln Gly Arg Thr Thr Ser Tyr Ser Thr Ala Ala Val
                740                 745                 750

Leu Pro Asn Pro Ile Pro Asn Pro Glu Ile Cys Tyr Asn Lys Leu Phe
                755                 760                 765

Ile Asn Asn Glu Trp His Asp Ala Val Gly Pro Gly Pro Gly Glu Val
770                 775                 780

Ser Gly Leu Glu Gln Leu Glu Ser Ile Ile Asn Phe Glu Lys Leu Thr
785                 790                 795                 800

Glu Trp Thr Ser Ser Asn Val Gly Gly Pro Gly Pro Gly Met Thr Glu
                805                 810                 815

Gln Gln Trp Asn Phe Ala Gly Ile Glu Ala Ala Ala Ser Ala Ile Gln
                820                 825                 830

Gly Asn Val Thr Ser Ile His Ser Leu Leu Asp Asp Tyr Lys Asp Asp
                835                 840                 845

Asp Asp Lys Gly Ser Asp Tyr Lys Asp His Asp Gly Asp Tyr Lys Asp
850                 855                 860

His Asp Ile Met Leu Ile Pro Ile Ala Val Gly Gly Ala Leu Ala Gly
865                 870                 875                 880

Leu Val Leu Ile Val Leu Ile Ala Tyr Leu Ile Gly Arg Lys Arg Cys
                885                 890                 895

Phe Cys

<210> SEQ ID NO 26
<211> LENGTH: 902
<212> TYPE: PRT
<213> ORGANISM: Artificial Sequence
<220> FEATURE:
<223> OTHER INFORMATION: MHC-II polypeptide for MHC-II presentation
      (sorting endosome target)

<400> SEQUENCE: 26

Met Leu Leu Leu Pro Phe Gln Leu Leu Ala Val Leu Phe Pro Gly Gly
1               5                   10                  15

Asn Ser Glu Ala Leu Gln Ala Tyr His Leu Asp Pro Gln Cys Trp Gly
                20                  25                  30

Val Asn Val Gln Pro Tyr Ser Gly Ser Pro Ala Asn Val Ala Val Tyr
                35                  40                  45

Thr Ala Leu Val Glu Pro His Gly Arg Ile Met Gly Leu Asp Leu Pro
            50                  55                  60

Asp Gly Gly His Leu Thr Gly Pro Gly Pro Gly Asp Thr Asp Glu Ala
65                  70                  75                  80

Glu Asp Pro Glu Lys Met Leu Ala Asn Phe Glu Ser Gly Lys His Lys
                85                  90                  95

Tyr Arg Gln Thr Ala Met Phe Thr Ala Thr Met Pro Pro Ala Val Glu
                100                 105                 110

Arg Leu Ala Arg Ser Tyr Leu Arg Arg Pro Ala Val Val Tyr Gly Pro
            115                 120                 125

Gly Pro Gly Arg Arg Tyr Leu Leu Gln Asn Thr Ala Leu Glu Val Phe
        130                 135                 140

Met Ala Asn Arg Thr Ser Val Met Phe Asn Phe Pro Glu Gln Ala Thr
145                 150                 155                 160

Val Lys Lys Val Val Tyr Ser Leu Pro Arg Val Gly Val Gly Thr Ser
                165                 170                 175

Tyr Gly Leu Pro Gln Ala Gly Pro Gly Pro Gly Lys Ile Glu Pro Asp
                180                 185                 190
```

```
Met Met Ser Met Glu His Ser Phe Glu Thr Ala Ser His Asp Gly Glu
        195                 200                 205

Ala Gly Pro Ser Pro Glu Val Leu Gln Gly Pro Gly Pro Gly Lys Val
    210                 215                 220

Leu Met Ala Ser Ser Tyr Leu Pro Ser Gln Val Thr Glu Met Phe
225                 230                 235                 240

Asn Gln Gly Arg Ala Phe Ala Ala Val Arg Leu Pro Phe Cys Gly His
                245                 250                 255

Lys Asn Ile Cys Ser Leu Thr Thr Ile Gln Lys Ile Pro Arg Leu Leu
                260                 265                 270

Val Gly Pro Gly Pro Gly Met Pro Ala Ala Glu Leu Ala Leu Ser Ala
            275                 280                 285

Phe Leu Val Leu Val Phe Leu Trp Val His Ser Leu Arg Arg Leu Leu
    290                 295                 300

Glu Cys Phe Tyr Val Ser Val Phe Ser Asn Ala Ala Ile His Val Val
305                 310                 315                 320

Gln Tyr Cys Phe Gly Leu Val Tyr Tyr Gly Pro Gly Pro Gly Leu Leu
                325                 330                 335

Glu Leu Leu His Cys Pro Leu Gly His Cys His Leu Cys Ser Glu Pro
            340                 345                 350

Met Phe Thr Phe Val Tyr Pro Thr Ile Phe Pro Leu Arg Glu Thr Pro
            355                 360                 365

Met Ala Gly Leu His Gln Arg Arg Thr Ser Ile Gly Phe Val Ala Tyr
    370                 375                 380

Cys Gly Pro Gly Pro Gly Ala His Phe Arg Leu Val Ser Lys Glu Lys
385                 390                 395                 400

Met Pro Trp Asp Ser Ile Lys Leu Thr Phe Glu Ala Thr Gly Pro Arg
                405                 410                 415

His Met Ser Phe Tyr Val Arg Thr His Lys Gly Ser Thr Leu Ser Gln
                420                 425                 430

Trp Ser Leu Gly Asn Gly Ile Pro Val Gly Pro Gly Pro Gly Gly Arg
    435                 440                 445

Thr Gln Gln Met Leu Ile Pro Ala Trp Gln Val Thr Pro Met Ala
    450                 455                 460

Pro Ala Ala Ala Thr Leu Thr Phe Glu Gly Met Ala Gly Ser Gln Arg
465                 470                 475                 480

Leu Gly Asp Trp Gly Lys Met Ile Pro His Ser Asn His Tyr Asn Ser
                485                 490                 495

Val Gly Pro Gly Pro Gly Glu Leu Gln Leu Val Gln Leu Glu Gly Gly
            500                 505                 510

Gly Gly Ser Gly Thr Tyr Arg Val Gly Asn Ala Gln Pro Ser Leu Ala
            515                 520                 525

Asp Cys Leu Asp Ala Gly Asp Leu Ala Gln Arg Leu Arg Glu His Gly
    530                 535                 540

Ala Glu Val Pro Thr Glu Pro Lys Glu Gly Pro Gly Pro Gly Glu Leu
545                 550                 555                 560

Glu Lys Phe Arg Lys Ser Glu Glu Gly Lys Gln Arg Ala Ala Ala Pro
                565                 570                 575

Ser Ala Ala Ser Ser Pro Ala Asp Val Gln Ser Leu Lys Lys Ala Met
                580                 585                 590

Ser Ser Leu Gln Asn Asp Arg Asp Arg Leu Leu Lys Glu Leu Lys Asn
                595                 600                 605
```

-continued

```
Leu Gly Pro Gly Pro Gly Gly Lys His Asp Arg Asp Leu Leu Ile Gly
        610             615             620
Thr Ala Lys His Gly Leu Asn Arg Thr Asp Tyr Tyr Ile Met Asn Gly
625             630              635             640
Pro Gln Leu Ser Phe Leu Asp Ala Tyr Arg Asn Tyr Ala Gln His Lys
            645             650             655
Arg Thr Asp Thr Gln Ala Pro Gly Ser Gly Pro Gly Pro Gly Ile Leu
            660             665             670
Glu Val Asp Lys Ser Gly Pro Ile Thr Leu Leu Val Gln Gly His Met
            675             680             685
Glu Gly Glu Val Trp Gly Leu Ser Thr His Pro Tyr Leu Pro Ile Cys
        690             695             700
Ala Thr Val Ser Asp Asp Lys Thr Leu Arg Ile Trp Asp Leu Ser Pro
705             710             715             720
Ser Gly Pro Gly Pro Gly Met Leu Thr Ala Arg Leu Leu Leu Pro Arg
            725             730             735
Leu Leu Cys Leu Gln Gly Arg Thr Thr Ser Tyr Ser Thr Ala Ala Val
            740             745             750
Leu Pro Asn Pro Ile Pro Asn Pro Glu Ile Cys Tyr Asn Lys Leu Phe
            755             760             765
Ile Asn Asn Glu Trp His Asp Ala Val Gly Pro Gly Pro Gly Glu Val
        770             775             780
Ser Gly Leu Glu Gln Leu Glu Ser Ile Ile Asn Phe Glu Lys Leu Thr
785             790             795             800
Glu Trp Thr Ser Ser Asn Val Gly Gly Pro Gly Pro Gly Met Thr Glu
            805             810             815
Gln Gln Trp Asn Phe Ala Gly Ile Glu Ala Ala Ala Ser Ala Ile Gln
            820             825             830
Gly Asn Val Thr Ser Ile His Ser Leu Leu Asp Asp Tyr Lys Asp Asp
            835             840             845
Asp Asp Lys Gly Ser Asp Tyr Lys Asp His Asp Gly Asp Tyr Lys Asp
        850             855             860
His Asp Ile Met Leu Ile Pro Ile Ala Val Gly Gly Ala Leu Ala Gly
865             870             875             880
Leu Val Leu Ile Val Leu Ile Ala Tyr Leu Ile Gly Lys Lys His Cys
            885             890             895
Ser Tyr Gln Asp Ile Leu
            900
```

SEQUENCE ARRANGEMENTS AND SEQUENCES FOR NEOEPITOPE PRESENTATION

This application claims priority to US provisional applications with the Ser. Nos. 62/313,621, filed 25 Mar. 2016, 62/312,974, filed 24 Mar. 2016, and 62/314,366, filed 28 Mar. 2016, all of which are incorporated by reference herein.

FIELD OF THE INVENTION

The field of the invention is compositions and methods of improved neoepitope-based immune therapeutics, especially as it relates to preparation of recombinant viral therapeutics for cancer therapy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer immunotherapies targeting certain antigens common to a specific cancer have led to remarkable responses in some patients. Unfortunately, many patients failed to respond to such immunotherapy despite apparent expression of the same antigen. One possible reason for such failure could be that various effector cells of the immune system may not have been present in sufficient quantities, or may have been exhausted. Moreover, intracellular antigen processing and HLA variability among patients may have led to insufficient processing of the antigen and/or antigen display, leading to a therapeutically ineffective or lacking response.

To increase the selection of targets for immune therapy, random mutations have more recently been considered since some random mutations in tumor cells may give rise to unique tumor specific antigens (neoepitopes). As such, and at least conceptually, neoepitopes may provide a unique precision target for immunotherapy. Additionally, it has been shown that cytolytic T-cell responses can be triggered by very small quantities of peptides (e.g., Sykulev et al., *Immunity*, Volume 4, Issue 6, p 565-571, 1 Jun. 1996). Moreover, due to the relatively large number of mutations in many cancers, the number of possible targets is relatively high. In view of these findings, the identification of cancer neoepitopes as therapeutic targets has attracted much attention. Unfortunately, current data appear to suggest that all or almost all cancer neoepitopes are unique to a patient and specific tumor and fail to provide any specific indication as to which neoepitope may be useful for an immunotherapeutic agent that is therapeutically effective.

To overcome at least some of the problems associated with large numbers of possible targets for immune therapy, the neoepitopes can be filtered for the type of mutation (e.g., to ascertain missense or nonsense mutation), the level of transcription to confirm transcription of the mutated gene, and to confirm protein expression. Moreover, the so filtered neoepitope may be further analyzed for specific binding to the patient's HLA system as described in WO 2016/172722. While such system advantageously reduces the relatively large number of potential neoepitopes, the significance of these neoepitopes with respect to treatment outcome remains uncertain. Still further, and especially where multiple peptides are to be expressed in an antigen presenting cell (e.g., dendritic cell), processing of precursor proteins to generate the neoepitopes is not fully understood and contributes as such to the lack of predictability of therapeutic success.

Thus, even though multiple methods of identification and delivery of neoepitopes to various cells are known in the art, all or almost all of them suffer from various disadvantages. Consequently, it would be desirable to have improved systems and methods for neoepitope selection and production that increases the likelihood of a therapeutic response in immune therapy.

SUMMARY OF THE INVENTION

The inventive subject matter is directed to various immune therapeutic compositions and methods, and especially recombinant viral expression systems, in which multiple selected neoepitopes are combined to form a rational-designed polypeptide with a trafficking signal to increase antigen processing and presentation and to so maximize therapeutic effect.

In one aspect of the inventive subject matter, the inventors contemplate a method of generating an expression vector for immune therapy. In preferred aspects, such method includes a step of constructing a recombinant nucleic acid that has a sequence that encodes a polytope that is operably linked to a promoter to drive expression of the polytope, wherein the polytope comprises multiple filtered neoepitope sequences. Most typically, the polytope includes one or more trafficking elements to directs the expressed polytope to a specific sub-cellular location, such as the cytoplasm, the proteasome, the recycling endosome, the sorting endosome, the lysosome, or the extracellular membrane. Alternatively, the trafficking element may also direct the polytope to the extracellular space for secretion.

Most preferably, the viral expression vector is an adenoviral expression vector having E1 and E2b genes deleted, and the promoter is a constitutive promoter. Alternatively, the promoter may also be an inducible promoter, and especially inducible under conditions that are common in a tumor microenvironment. Thus, suitable promoters may be inducible by hypoxia, IFN-gamma, and/or IL-8.

With respect to appropriate trafficking element it is contemplated that all know trafficking elements are suitable, however, preferred trafficking elements include cleavable ubiquitin, non-cleavable ubiquitin, a CD1b leader sequence, a CD1a tail, a CD1c tail, and a LAMP1-transmembrane sequence. Furthermore, it is contemplated that the filtered neoepitope sequences are filtered by comparing tumor versus matched normal of the same patient, by determination to have binding affinity to an MHC complex of equal or less than 200 nM, and/or the filtered neoepitope sequences are filtered against known human SNP and somatic variations.

It is further contemplated that the filtered neoepitope sequences have an arrangement within the polytope such that the polytope has a likelihood of a presence and/or strength of hydrophobic sequences or signal peptides that is below a predetermined threshold. Contemplated filtered neoepitope sequences may bind to MHC-I (typically with an affinity of less than 200 nM) while the trafficking element directs the polytope to the cytoplasm or proteasome, or may bind to MHC-I (typically with an affinity of less than 200 nM) while the trafficking element directs the polytope to the recycling endosome, sorting endosome, or lysosome, or may bind to MHC-II (typically with an affinity of less than 200 nM) while the trafficking element directs the polytope to the recycling endosome, sorting endosome, or lysosome.

In still further contemplated aspects, the recombinant nucleic acid may further include a sequence that encodes a second polytope, wherein the second polytope comprises a second trafficking element that directs the second polytope to a different sub-cellular location and wherein the second polytope comprises a second plurality of filtered neoepitope sequences (e.g., at least some of the plurality of filtered neoepitope sequences and some of the second plurality of filtered neoepitope sequences are identical).

Where desired, the recombinant nucleic acid may also comprises a sequence that encodes one or more co-stimulatory molecules (e.g., CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, LFA3), one or more immune stimulatory cytokines (e.g., IL-2, IL-12, IL-15, IL-15 super agonist (ALT803), IL-21, IPS1, and LMP1), and/or one or more proteins that interferes with or down-regulates checkpoint inhibition (e.g., antibody or an antagonist of CTLA-4, PD-1, TIM1 receptor, 2B4, or CD160).

Viewed from a different perspective, the inventors also contemplate a recombinant expression vector for immune therapy that comprises a sequence that encodes a polytope (e.g., comprising a plurality of filtered neoepitope sequences) operably linked to a promoter to drive expression of the polytope. Most typically, the polytope includes a trafficking element that directs the polytope to a sub-cellular location (e.g., cytoplasm, recycling endosome, sorting endosome, lysosome, extracellular membrane), or the trafficking element directs the polytope to an extracellular space for secretion of the polytope.

Preferred recombinant expression vectors are adenoviral expression vectors, especially having the E1 and E2b genes deleted. Such and other expression vectors may have a constitutive promoter, or an inducible promoter (preferably induced by hypoxia, IFN-gamma, or IL-8). As noted above it is contemplated that the trafficking element is a cleavable ubiquitin, a non-cleavable ubiquitin, a CD1b leader sequence, a CD1a tail, a CD1c tail, and/or a LAMP1-transmembrane sequence.

With respect to the filtered neoepitope sequences it is contemplated that the sequences are filtered by comparing tumor versus matched normal of the same patient, filtered to have binding affinity to an MHC complex of equal or less than 200 nM, and/or filtered against known human SNP and somatic variations. Furthermore, the filtered neoepitope sequences have preferably an arrangement within the polytope such that the polytope has a likelihood of a presence and/or strength of hydrophobic sequences or signal peptides that is below a predetermined threshold to so avoid misdirecting the polytope.

For example, the filtered neoepitope sequences may bind to MHC-I (typically with an affinity of less than 200 nM) while the trafficking element directs the polytope to the cytoplasm or proteasome, or the filtered neoepitope sequences may bind to MHC-I (typically with an affinity of less than 200 nM) while the trafficking element directs the polytope to the recycling endosome, sorting endosome, or lysosome, or the filtered neoepitope sequences may bind to MHC-II (typically with an affinity of less than 200 nM) and wherein the trafficking element directs the polytope to the recycling endosome, sorting endosome, or lysosome.

Additionally, it is contemplated that the recombinant nucleic acid may further include a sequence that encodes a second polytope, wherein the second polytope comprises a second trafficking element that directs the second polytope to a different sub-cellular location and wherein the second polytope comprises a second plurality of filtered neoepitope sequences. For example, at least some of the plurality of filtered neoepitope sequences and some of the second plurality of filtered neoepitope sequences are identical. Where desired, the recombinant nucleic acid may further comprise a sequence that encodes one or more co-stimulatory molecules (e.g., CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, LFA3), one or more immune stimulatory cytokines (e.g., IL-2, IL-12, IL-15, IL-15 super agonist (ALT803), IL-21, IPS1, and LMP1), and/or one or more proteins that interferes with or down-regulates checkpoint inhibition (e.g., antibody or an antagonist of CTLA-4, PD-1, TIM1 receptor, 2B4, or CD160).

Therefore, the inventors also contemplate a recombinant virus that includes the recombinant vector as described herein. Most typically, the virus is a replication deficient virus (e.g., adenovirus, preferably with deleted E1 and E2b gene). Such virus may then be included in a pharmaceutical composition that is typically formulated for injection or intranasal administration. While not limiting to the inventive subject matter, such recombinant virus may then be used in the treatment of cancer, and/or in the manufacture of a medicament for treatment of cancer.

Consequently, the inventors also contemplate a method of treating an individual that typically includes a step of transfecting a cell of the individual with a recombinant virus, wherein the recombinant virus comprises a sequence that encodes a polytope operably linked to a promoter to drive expression of the polytope in the cell. The polytope comprises a trafficking element that directs the polytope to a sub-cellular location selected from the group consisting of cytoplasm, recycling endosome, sorting endosome, lysosome, and extracellular membrane, or the trafficking element directs the polytope to an extracellular space. Most typically, the polytope in such methods comprises a plurality of filtered neoepitope sequences.

With respect to the recombinant virus, the promoter, the trafficking element, and the filtered neoepitope sequences, the same considerations as noted above apply. As also noted above it is contemplated that the recombinant nucleic acid further may comprise a sequence that encodes a second polytope, wherein the second polytope comprises a second trafficking element that directs the second polytope to a different sub-cellular location and that the second polytope comprises a second plurality of filtered neoepitope sequences.

In further contemplated methods, a step of transfecting another cell of the individual with a second recombinant virus may be included, wherein the second recombinant virus comprises a second sequence that encodes a second polytope operably linked to a promoter to drive expression of the second polytope in the another cell, wherein the second polytope comprises a second trafficking element that directs the polytope to a second sub-cellular location selected from the group consisting of cytoplasm, recycling endosome, sorting endosome, lysosome, and extracellular membrane, or wherein the trafficking element directs the polytope to an extracellular space, and wherein the subcellular location and the second sub-cellular location are distinct, and wherein the second polytope comprises a second plurality of filtered neoepitope sequences. For example, at least some of the plurality of filtered neoepitope sequences and some of the second plurality of filtered neoepitope sequences may be identical.

Contemplated recombinant viruses in such methods may further comprises a sequence that encodes one or more co-stimulatory molecules (e.g., CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, LFA3), one or more immune stimulatory cytokines (e.g., IL-2, IL-12, IL-15, IL-15 super agonist (ALT803), IL-21, IPS1, and LMP1), and/or one or more proteins that interferes with or down-regulates checkpoint inhibition (e.g., antibody or an antagonist of CTLA-4, PD-1, TIM1 receptor, 2B4, or CD160).

Viewed from yet another perspective, the inventors also contemplate a method of biasing an immune response against a neoepitope in an individual towards a CD4+ biased immune response. Such method will typically include a step of transfecting a cell of the individual with a recombinant virus, wherein the recombinant virus comprises a sequence that encodes a polytope operably linked to a promoter to drive expression of the polytope in the cell, wherein the polytope comprises the neoepitope. Most typically, the polytope comprises a trafficking element that directs the polytope to a sub-cellular location selected from the group consisting of a recycling endosome, a sorting endosome, and a lysosome. In a further step, the polytope is expressed from the sequence, trafficked, and proteolytically processed to present the neoepitope on a MHC-II complex and to thereby stimulate CD4+ T-cells.

Suitable neoepitope may be calculated to bind to MHC-I (typically with an affinity of less than 200 nM) or to bind to MHC-II (typically with an affinity of less than 200 nM), and/or suitable trafficking elements include a CD1b leader sequence, a CD1a tail, a CD1c tail, and a LAMP1-transmembrane sequence. As noted above, the recombinant virus may further comprise a sequence that encodes at least one of a co-stimulatory molecule, an immune stimulatory cytokine, and a protein that interferes with or down-regulates checkpoint inhibition.

Likewise, the inventors also contemplate a method of biasing an immune response against a neoepitope in an individual towards a CD8+ biased immune response. Such method will typically include a step of transfecting a cell of the individual with a recombinant virus, wherein the recombinant virus comprises a sequence that encodes a polytope operably linked to a promoter to drive expression of the polytope in the cell, wherein the polytope comprises the neoepitope. Most typically, the polytope comprises a trafficking element that directs the polytope to the proteasome. In a further step, the polytope is expressed from the sequence, trafficked, and proteolytically processed to present the neoepitope on a MHC-I complex and to thereby stimulate CD8+ T-cells.

Suitable neoepitope may be calculated to bind to MHC-I (typically with an affinity of less than 200 nM) or to bind to MHC-II (typically with an affinity of less than 200 nM), and/or suitable trafficking elements include a CD1b leader sequence, a CD1a tail, a CD1c tail, and a LAMP1-transmembrane sequence. As noted above, the recombinant virus may further comprise a sequence that encodes at least one of a co-stimulatory molecule, an immune stimulatory cytokine, and a protein that interferes with or down-regulates checkpoint inhibition.

In yet another aspect of the inventive subject matter, the inventors contemplate a method of generating a polytope for immune therapy. Such method preferably comprises a step of obtaining a plurality of neoepitope sequences, and generating a set of polytope sequences, each having a distinct linear arrangement of the plurality of neoepitope sequences. In another step, for each of the polytope sequences a score is calculated that is representative for a likelihood of presence and/or strength of hydrophobic sequences or signal peptides, and in yet another step, the score is used to rank the polytope sequences. The linear arrangement of the plurality of neoepitope sequences is then selected on the basis of the rank.

Most preferably, the score is calculated using at least one of a weight matrix and a neural network prediction, and/or the neoepitope sequences are filtered by at least one of MHC binding strength, known human SNP and somatic variations, and comparing tumor versus matched normal of the same patient. Typically, each of the polytope sequences comprises at least five neoepitope sequences.

Various objects, features, aspects and advantages of the inventive subject matter will become more apparent from the following detailed description of preferred embodiments, along with the accompanying drawing in which like numerals represent like components.

BRIEF DESCRIPTION OF THE DRAWING

FIG. 1 is a schematic representation of various neoepitope arrangements.

FIG. 2 is an exemplary and partial schematic for selecting preferred arrangements of neoepitopes.

Prior Art FIG. 3 is a schematic illustration of antigen processing in the cytoplasm and MHC-I presentation.

Prior Art FIG. 4 is a schematic illustration of antigen processing in the lysosomal and endosomal compartment and MHC-II presentation.

FIGS. 5A-5C are exemplary sequence arrangements for class I antigen processing in the cytoplasm and MHC-I presentation.

FIGS. 6A-6C are exemplary sequence arrangements for class I antigen processing in the cytoplasm and MHC-II presentation.

FIGS. 7A-7C are exemplary sequence arrangements for class II antigen processing in the cytoplasm and MHC-II presentation.

DETAILED DESCRIPTION

Figure 8:
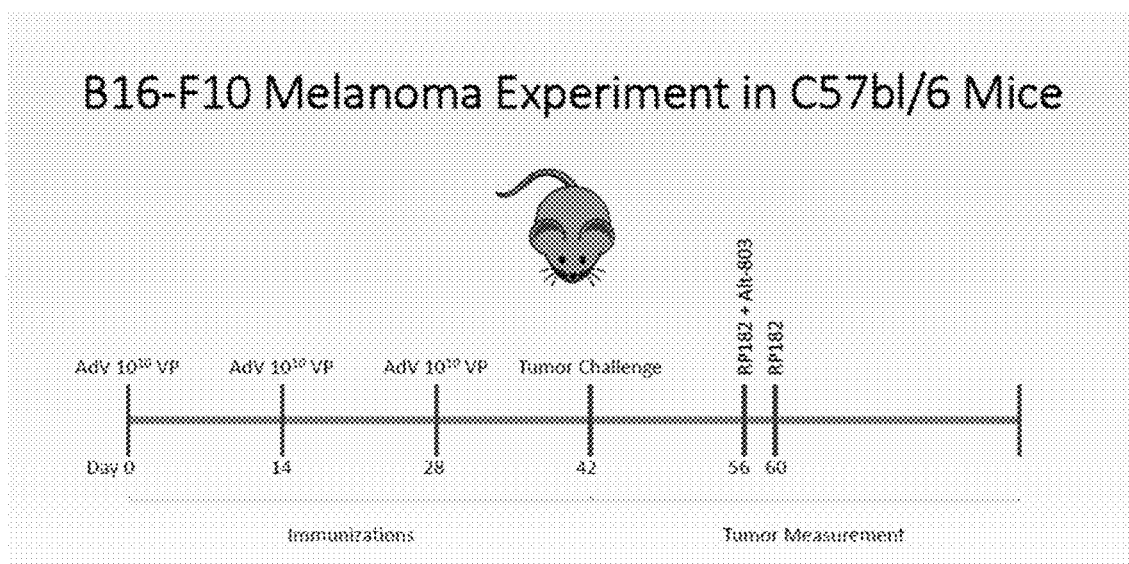
FIG. 8 is an exemplary prophylactic vaccination schedule for B16-F10 melanoma.

The inventors have discovered that neoepitope-based immune therapy can be further improved by targeting expressed patient- and tumor specific neoepitopes towards processing and/or specific cell surface presentation or even secretion, and that neoepitope-based therapy can still further be augmented using checkpoint inhibition, immune stimulation via cytokines, and/or inhibitors of myeloid derived suppressor cells (MDCS), T-regulatory cells (Tregs), or M2 macrophages. Most preferably, such therapeutic entities will be expressed in vivo from a recombinant nucleic acid, and especially suitable recombinant nucleic acid include plasmids and viral nucleic acids. Where a viral nucleic acid is employed, it is particularly preferred that the nucleic acid is delivered via infection of the patient or patient cells by the virus.

Viewed from a different perspective, it should be appreciated that the compositions and methods presented herein will include one or more neoepitopes that are specific to the patient and the tumor in the patient to allow for targeted treatment. Moreover, such treatment may advantageously be tailored to achieve one or more specific immune reactions, including a CD4+ biased immune response, a CD8+ biased immune response, antibody biased immune response, and/or a stimulated immune response (e.g., reducing checkpoint inhibition and/or by activation of immune competent cells using cytokines). Most typically, such effects are in achieved in the context of the neoepitopes originating from the recombinant nucleic acid.

Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a content filter through which silent and other non-relevant (e.g., non-expressed) mutations are eliminated. It should also be appreciated that neoepitope sequences can be defined as sequence stretches with relatively short length (e.g., 8-12 mers or 14-20 mers) wherein such stretches will include the change(s) in the amino acid sequences. Most typically, but not necessarily, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic wild type or normal (i.e., from corresponding healthy tissue of the same patient) amino acid and N is a changed amino acid (relative to wild type or relative to matched normal). Therefore, the neoepitope sequences contemplated herein include sequence stretches with relatively short length (e.g., 5-30 mers, more typically 8-12 mers, or 14-20 mers) wherein such stretches include the change(s) in the amino acid sequences. Where desired, additional amino acids may be placed upstream or downstream of the changed amino acid, for example, to allow for additional antigen processing in the various compartments (e.g., for proteasome processing in the cytosol, or specific protease processing in the endosomal and/or lysosomal compartments) of a cell.

Thus, it should be appreciated that a single amino acid change may be presented in numerous neoepitope sequences that include the changed amino acid, depending on the position of the changed amino acid. Advantageously, such sequence variability allows for multiple choices of neoepitopes and as such increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 8-12 amino acids, or 14-20 amino acids, with the changed amino acid preferably centrally located or otherwise situated in a manner that improves its binding to MHC. For example, where the epitope is to be presented by the MHC-I complex, a typical neoepitope length will be about 8-12 amino acids, while the typical neoepitope length for presentation via MHC-II complex will have a length of about 14-20 amino acids. As will be readily appreciated, since the position of the changed amino acid in the neoepitope may be other than central, the actual peptide sequence and with that actual topology of the neoepitope may vary considerably, and the neoepitope sequence with a desired binding affinity to the MHC-I or MHC-II presentation and/or desired protease processing will typically dictate the particular sequence.

Of course, it should be appreciated that the identification or discovery of neoepitopes may start with a variety of biological materials, including fresh biopsies, frozen, or otherwise preserved tissue or cell samples, circulating tumor cells, exosomes, various body fluids (and especially blood), etc. Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and in some cases protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination of the same patient. Therefore, data sets suitable for use herein include unprocessed or processed data sets, and exemplary preferred data sets include those having BAM format, SAM format, GAR format, FASTQ format, or FASTA format, as well as BAM-BAM, SAMBAM, and VCF data sets. However, it is especially preferred that the data sets are provided in BAM format or as BAMBAM diff objects as is described in US2012/0059670A1 and US2012/0066001A1. Moreover, it should be noted that the data sets are reflective of a tumor and a matched normal sample of the same patient. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor and/or metastatic site, etc. In most cases, the matched normal sample of the patient is blood, or a non-diseased tissue from the same tissue type as the tumor.

Likewise, the computational analysis of the sequence data may be performed in numerous manners. In most preferred methods, however, analysis is performed in silico by location-guided synchronous alignment of tumor and normal samples as, for example, disclosed in US 2012/0059670 and US 2012/0066001 using BAM files and BAM servers. Such analysis advantageously reduces false positive neoepitopes and significantly reduces demands on memory and computational resources.

For example, contemplated methods of processing enables BamBam to efficiently calculate overall copy number and infer regions of structural variation (for example, chromosomal translocations) in both tumor and germline genomes; to efficiently calculate overall and allele-specific copy number; infer regions exhibiting loss of heterozygosity (LOH); and discover both somatic and germline sequence variants (for example, point mutations) and structural rearrangements (for example, chromosomal fusions. Furthermore, by comparing the two genome sequences at the same time, BamBam can also immediately distinguish somatic from germline sequence variants, calculate allele-specific copy number alterations in the tumor genome, and phase germline haplotypes across chromosomal regions where the allelic proportion has shifted in the tumor genome. By bringing together all of these analyses into a single tool, researchers can use BamBam to discover many types of genomic alterations that occurred within a patient's tumor genome, often to specific gene alleles, that help to identify potential drivers of tumorigenesis.

To determine if a variant discovered is somatic (that is, a variant sequence found only in the tumor) or a germline (that is, a variant sequence that is inherited or heritable) variant requires that we compare the tumor and matched normal genomes in some way. This can be done sequentially, by summarizing data at every genomic position for both tumor and germline and then combining the results for analysis. Unfortunately, because whole-genome BAM files are hundreds of gigabytes in their compressed form (1-2 terabytes uncompressed), the intermediate results that would need to be stored for later analysis will be extremely large and slow to merge and analyze.

To avoid this issue, BamBam reads from two files at the same time, constantly keeping each BAM file in synchrony with the other and piling up the genomic reads that overlap every common genomic location between the two files. For each pair of pileups, BamBam runs a series of analyses listed above before discarding the pileups and moving to the next common genomic location. By processing these massive BAM files with this method, the computer's RAM usage is minimal and processing speed is limited primarily by the speed that the filesystem can read the two files. This enables BamBam to process massive amounts of data quickly, while being flexible enough to run on a single computer or across a computer cluster. Another important benefit to processing these files with BamBam is that its output is fairly minimal, consisting only of the important differences found in each file. This produces what is essentially a whole-genome diff between the patient's tumor and germline genomes, requiring much less disk storage than it would take if all genome information was stored for each file separately.

BamBam is a computationally efficient method for surveying large sequencing datasets to produce a set of high-quality genomic events that occur within each tumor relative to its germline. These results provide a glimpse into the chromosomal dynamics of tumors, improving our understanding of tumors' final states and the events that led to them. An exemplary scheme of BamBam Data Flow is shown at FIG. 1.

One particular exemplary embodiment of the invention is creation and use of a differential genetic sequence object. As used herein, the object represents a digital object instantiated from the BamBam techniques and reflects a difference between a reference sequence (for example, a first sequence) and an analysis sequence (for example, a second sequence).

Dataset Synchronization Via the Reference Genome; All short reads are aligned to the same reference genome, making the reference genome a natural way of organizing sequence data from multiple, related samples. BamBam takes in two short read sequencing datasets, one from the tumor and the other a matched normal ("germline") from the same patient, and the reference genome, and reads these datasets such that all sequences in both datasets overlapping the same genomic position are available to be processed at the same time. This is the most efficient method for processing such data, while also enabling complex analyses that would be difficult or impossible to accomplish in a serialized manner, where each dataset is processed by itself, and results are only merged afterwards.

Such a method is easily extendible to more than two related sequencing datasets. For example, if three samples, matched normal, tumor, and relapse, were sequenced, this method could be used to search for changes specific to the tumor & the relapse sample, and changes specific only to the relapse, suggesting the relapse tumor has changed somewhat from the original tumor from which it had presumably derived. Also, one could use this same method to determine the inherited portions of a child's genome given sequenced samples from child, father, and mother.

Somatic and Germline Variant Calling: Because BamBam keeps the sequence data in the pair of files in sync across the genome, a complex mutation model that requires sequencing data from both tumor and germline BAM files as well as the human reference can be implemented easily. This model aims to maximize the joint probability of both the germline genotype (given the germline reads and the reference nucleotide) and the genotype of the tumor (given the germline genotype, a simple mutation model, an estimate of the fraction of contaminating normal tissue in the tumor sample, and the tumor sequence data).

To find the optimal tumor and germline genotype, we aim to maximize the likelihood defined by $$P(D_g, D_t, G_g, G_t | \alpha, r) = P(D_g | G_g) P(G_g | r) P(D_t | G_g, G_t, \alpha) P(G_t | G_g) \qquad (1)$$

$$P(D_{\downarrow g}, D_{\downarrow t}, G_{\downarrow g}, G_{\downarrow t} \neg | \alpha, r) = P(D_{\downarrow g} \neg | G_{\downarrow g}) P(G_{\downarrow g} | r) P(D_{\downarrow t} \neg | G_{\downarrow g}, G_{\downarrow t}, \alpha) P(G_{\downarrow t} \neg | G_{\downarrow g}) \qquad (1)$$

where r is the observed reference allele, α the fraction of normal contamination, and the tumor and germline genotypes are defined by Gt=(t1, t2) and Gg=(g1, g2) where t1, t2, g1, g2ε{A, T, C, G}. The tumor and germline sequence data are defined as a set of reads Dt={dt1, dt2, . . . , dtm} and Dg={dg1, dg2, . . . , dgm}, respectively, with the observed bases dti, dgiε{A, T, C, G}. All data used in the model must exceed user-defined base and mapping quality thresholds.

The probability of the germline alleles given the germline genotype is modeled as a multinomial over the four nucleotides:

$$P(D_g | G_g) = \frac{n!}{n_A! n_T! n_G! n_C!} \prod_i^n P(d_g^i | G_g)$$

where n is the total number of germline reads at this position and nA, nG, nC, nT are the reads supporting each observed allele. The base probabilities, P(dgi|Gg), are assumed to be independent, coming from either of the two parental alleles represented by the genotype Gg, while also incorporating the approximate base error rate of the sequencer. The prior on the germline genotype is conditioned on the reference base as $$P(G_g|r=a)=\{\mu_{aa},\mu_{ab},\mu_{bb}\},$$

where μaa is the probability that the position is homozygous reference, μab is heterozygous reference, and μbb is homozygous non-reference. At this time, the germline prior does not incorporate any information on known, inherited SNPs.

The probability of the set of tumor reads is again defined as multinomial $$P(D_t | D_t, G_g, \alpha) = \frac{n!}{n_A!n_T!n_G!n_C!}\prod_i^n P(d_g^i | G_t, G_g, \alpha)$$

where m is the total number of germline reads at this position and mA, mG, mC, mT are the reads supporting each observed allele in the tumor dataset, and the probability of each tumor read is a mixture of base probabilities derived from both tumor and germline genotypes that is controlled by the fraction of normal contamination, α, as $$P(d_t^i|G_t,G_g,\alpha)=\alpha P(d_t^i|G_t)+(1-\alpha)P(d_t^i|G_g)$$

and the probability of the tumor genotype is defined by a simple mutation model from on the germline genotype $$P(G_t|G_g)=\max[P(t_1|g_1)P(t_2|g_2),P(t_1|g_2)P(t_2|g_1)],$$

where the probability of no mutation (for example, $t_1=g_1$) is maximal and the probability of transitions (that is, A→G, T→C) are four times more likely than transversions (that is, A→T, T→G). All model parameters, α, μaa, μab, μbb, and base probabilities, $P(d^i|G)$, for the multinomial distributions are user-definable.

The tumor and germline genotypes, $G_t^{max}$, $G_g^{maxi}$, selected are those that maximize (1), and the posterior probability defined by $$\frac{P(D_g, D_t, G_g^{max}, G_t^{max} | \alpha, r)}{\sum_{i,j} P(D_g, D_t, G_g = i, G_t = j | \alpha, r)}$$

can be used to score the confidence in the pair of inferred genotypes. If the tumor and germline genotypes differ, the putative somatic mutation(s) will be reported along with its respective confidence.

Maximizing the joint likelihood of both tumor and germline genotypes helps to improve the accuracy of both inferred genotypes, especially in situations where one or both sequence datasets have low coverage of a particular genomic position. Other mutation calling algorithms, such as MAQ and SNVMix, that analyze a single sequencing dataset are more likely to make mistakes when the non-reference or mutant alleles have low support (Li, H., et al. (2008) Mapping short DNA sequencing reads and calling variants using mapping quality scores, Genome Research, 11, 1851-1858; Goya, R. et al. (2010) SNVMix: predicting single nucleotide variants from next-generation sequencing of tumors, Bioinformatics, 26, 730-736).

In addition to collecting allele support from all reads at a given genomic position, information on the reads are collected (such as which strand, forward or reverse, the read maps to, the position of the allele within the read, the average quality of the alleles, etc.) and used to selectively filter out false positive calls. We expect a random distribution of strands and allele positions for all of the allele supporting a variant, and if the distribution is skewed significantly from this random distribution (that is, all variant alleles are found near the tail end of a read), then this suggest that the variant call is suspect.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Viewed from a different perspective, a patient- and cancer-specific in silico collection of sequences can be established that encode neoepitopes having a predetermined length of, for example, between 5 and 25 amino acids and include at least one changed amino acid. Such collection will typically include for each changed amino acid at least two, at least three, at least four, at least five, or at least six members in which the position of the changed amino acid is not identical. Such collection advantageously increases potential candidate molecules suitable for immune therapy and can then be used for further filtering (e.g., by subcellular location, transcription/expression level, MHC-I and/or II affinity, etc.) as is described in more detail below.

For example, and using synchronous location guided analysis to tumor and matched normal sequence data, the inventors previously identified various cancer neoepitopes from a variety of cancers and patients, including the following cancer types: BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC. Exemplary neoepitope data for these cancers can be found in International application PCT/US16/29244, incorporated by reference herein.

Depending on the type and stage of the cancer, as well as the patient's immune status it should be recognized that not all of the identified neoepitopes will necessarily lead to a therapeutically equally effective reaction in a patient. Indeed, it is well known in the art that only a fraction of neoepitopes will generate an immune response. To increase likelihood of a therapeutically desirable response, the initially identified neoepitopes can be further filtered. Of course, it should be appreciated that downstream analysis need not take into account silent mutations for the purpose of the methods presented herein. However, preferred mutation analyses will provide in addition to the particular type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation.

In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, at least 30%, at least 40%, or at least 50% of expression level of the corresponding matched normal sequence, thus ensuring that the (neo) epitope is at least potentially 'visible' to the immune system. Consequently, it is generally preferred that the omics analysis also includes an analysis of gene expression (transcriptomic analysis) to so help identify the level of expression for the gene with a mutation.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using RNAseq, qPCR and/or rtPCR based methods, although various alternative methods (e.g., solid phase hybridization-based methods) are also deemed suitable. Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)). Consequently, it should be appreciated that the above methods will provide patient and tumor specific neoepitopes, which may be further filtered by sub-cellular location of the protein containing the neoepitope (e.g., membrane location), the expression strength (e.g., overexpressed as compared to matched normal of the same patient), etc.

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database and other filtering options as described above, the patient and tumor specific neoepitopes may be filtered to remove those known sequences, yielding a sequence set with a plurality of neoepitope sequences having substantially reduced false positives.

Once the desired level of filtering for the neoepitope is accomplished (e.g., neoepitope filtered by tumor versus normal, and/or expression level, and/or sub-cellular location, and/or patient specific HLA-match, and/or known variants), a further filtering step is contemplated that takes into account the gene type that is affected by the neoepitope. For example, suitable gene types include cancer driver genes, genes associated with regulation of cell division, genes associated with apoptosis, and genes associated with signal transduction. However, in especially preferred aspects, cancer driver genes are particularly preferred (which may span by function a variety of gene types, including receptor genes, signal transduction genes, transcription regulator genes, etc.). In further contemplated aspects, suitable gene types may also be known passenger genes and genes involved in metabolism.

With respect to the identification or other determination (e.g., prediction) of a gene as being a cancer driver gene, various methods and prediction algorithms are known in the art, and are deemed suitable for use herein. For example, suitable algorithms include MutsigCV (*Nature* 2014, 505 (7484):495-501), ActiveDriver (*Mol Syst Biol* 2013, 9:637), MuSiC (*Genome Res* 2012, 22(8):1589-1598), Oncodrive-Clust (*Bioinformatics* 2013, 29(18):2238-2244), OncodriveFM (*Nucleic Acids Res* 2012, 40(21):e169), OncodriveFML (*Genome Biol* 2016, 17(1):128), Tumor Suppressor and Oncogenes (TUSON) (*Cell* 2013, 155(4): 948-962), 20/20+ (https://github.com/KarchinLab/2020plus), and oncodriveROLE (*Bioinformatics* (2014) 30 (17): i549-i555). Alternatively, or additionally, identification of cancer driver genes may also employ various sources for known cancer driver genes and their association with specific cancers. For example, the Intogen Catalog of driver mutations (2016.5; URL: www.intogen.org) contains the results of the driver analysis performed by the Cancer Genome Interpreter across 6,792 exomes of a pan-cancer cohort of 28 tumor types.

Nevertheless, despite filtering, it should be recognized that not all neoepitopes will be visible to the immune system as the neoepitopes also need to be processed where present in a larger context (e.g., within a polytope) and presented on the MHC complex of the patient. In that context, it must be appreciated that only a fraction of all neoepitopes will have sufficient affinity for presentation. Consequently, and especially in the context of immune therapy it should be apparent that neoepitopes will be more likely effective where the neoepitopes are properly processed, bound to, and presented by the MHC complexes. Viewed from another perspective, treatment success will be increased with an increasing number of neoepitopes that can be presented via the MHC complex, wherein such neoepitopes have a minimum affinity to the patient's HLA-type. Consequently, it should be appreciated that effective binding and presentation is a combined function of the sequence of the neoepitope and the particular HLA-type of a patient. Therefore, HLA-type determination of the patient tissue is typically required. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each subtype being determined to at least 2-digit or at least 4-digit depth. However, greater depth (e.g., 6 digit, 8 digit) is also contemplated.

Once the HLA-type of the patient is ascertained (using known chemistry or in silico determination), a structural solution for the HLA-type is calculated and/or obtained from a database, which is then used in a docking model in silico to determine binding affinity of the (typically filtered) neoepitope to the HLA structural solution. As will be further discussed below, suitable systems for determination of binding affinities include the NetMHC platform (see e.g., Nucleic Acids Res. 2008 Jul. 1; 36(Web Server issue): W509-W512.). Neoepitopes with high affinity (e.g., less than 100 nM, less than 75 nM, less than 50 nM) for a previously determined HLA-type are then selected for therapy creation, along with the knowledge of the patient's MHC-I/II subtype.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types. For example, in one preferred method according to the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, URL: www.allelefrequencies.net). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in WO 2017/035392, incorporated by reference herein.

Once patient and tumor specific neoepitopes and HLA-type are identified, further computational analysis can be performed by in silico docking neoepitopes to the HLA and determining best binders (e.g., lowest $K_D$, for example, less than 500 nM, or less than 250 nM, or less than 150 nM, or less than 50 nM), for example, using NetMHC. It should be appreciated that such approach will not only identify specific neoepitopes that are genuine to the patient and tumor, but also those neoepitopes that are most likely to be presented on a cell and as such most likely to elicit an immune response with therapeutic effect. Of course, it should also be appreciated that thusly identified HLA-matched neoepitopes can be biochemically validated in vitro prior to inclusion of the nucleic acid encoding the epitope as payload into the virus as is further discussed below.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), Rank-Pep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type. Moreover, where desired, binding of corresponding wild type sequences (i.e., neoepitope sequence without amino acid change) can be calculated to ensure high differential affinities. For example, especially preferred high differential affinities in MHC binding between the neoepitope and its corresponding wild type sequence are at least 2-fold, at least 5-fold, at least 10-fold, at least 100-fold, at least 500-fold, at least 1000-fold, etc.).

Binding affinity, and particularly differential binding affinity may also be determined in vitro using various systems and methods. For example, antigen presenting cells of a patient or cells with matched HLA-type can be transfected with a nucleic acid (e.g., viral, plasmid, linear DNA, RNA, etc.) to express one or more neoepitopes using constructs as described in more detail below. Upon expression and antigen processing, the neoepitopes can then be identified in the MHC complex on the outside of the cell, either using specific binders to the neoepitope or using a cell based system (e.g., PBMC of the patient) in which T cell activation or cytotoxic NK cell activity can be observed in vitro. Neoepitopes with differential activity (elicit a stronger signal or immune response as compared to the corresponding wild type epitope) will then be selected for therapy creation.

Upon identification of desired neoepitopes, one or more immune therapeutic agents may be prepared using the sequence information of the neoepitope. Among other agents, it is especially preferred that the patient may be treated with a virus that is genetically modified with a nucleic acid construct as further discussed below that leads to expression of at least one of the identified neoepitopes to initiate an immune response against the tumor. For example, suitable viruses include adenoviruses, adeno-associated viruses, alphaviruses, herpes viruses, lentiviruses, etc. However, adenoviruses are particularly preferred. Moreover, it is further preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933).

Regardless of the type of recombinant virus it is contemplated that the virus may be used to infect patient (or non-patient) cells ex vivo or in vivo. For example, the virus may be injected subcutaneously or intravenously, or may be administered intranasally or via inhalation to so infect the patients cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially immune competent cells.

Most typically, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc.

In this context, it should be appreciated that the inventors have discovered that the manner of neoepitope arrangement and rational-designed trafficking of the neoepitopes can have a substantial impact on the efficacy of various immune therapeutic compositions. For example, single neoepitopes can be expressed individually from the respective recombinant constructs that are delivered as a single plasmid, viral expression construct, etc. Alternatively, multiple neoepitopes can be separately expressed from individual promoters t form individual mRNA that are then individually translated into the respective neoepitopes, or from a single mRNA comprising individual translation starting points for each neoepitope sequence (e.g., using 2A or IRES signals). Notably, while such arrangements are generally thought to allow for controlled delivery of proper neoepitope peptide, efficacy of such expression systems has been less than desirable (data not shown).

In contrast, where multiple neoepitopes were expressed from a single transcript to so form a single transcript that is then translated into a single polytope (i.e., polypeptide with a series of concatemerically linked neoepitopes, optionally with intervening linker sequences) expression, processing, and antigen presentation was found to be effective. Notably, the expression of polytopes requires processing by the appropriate proteases (e.g., proteasome, endosomal proteases, lysosomal proteases) within a cell to yield the neoepitope sequences, and polytopes led to improved antigen processing and presentation for most neoepitopes as compared to expression of individual neoepitopes, particularly where the individual neoepitopes had a relatively short length (e.g., less than 25 amino acids; results not shown). Moreover, such approach also allows rational design of protease sensitive sequence motifs between the neoepitope peptide sequences to so assure or avoid processing by specific proteases as the proteasome, endosomal proteases, and lysosomal proteases have distinct cleavage preferences. Therefore, polytopes may be designed that include not only linker sequences to spatially separate neoepitopes, but also sequence portions (e.g., between 3-15 amino acids) that will be preferentially cleaved by a specific protease.

Therefore, the inventors contemplate recombinant nucleic acids and expression vectors (e.g., viral expression vectors) that comprise a nucleic acid segment that encodes a polytope wherein the polytope is operably coupled to a desired promoter element, and wherein individual neoepitopes are optionally separated by a linker and/or protease cleavage or recognition sequence. For example, FIG. 1 exemplarily illustrates various contemplated arrangements for neoepitopes for expression from an adenoviral expression system (here: AdV5, with deletion of E1 and E2b genes). Here, Construct 1 exemplarily illustrates a neoepitope arrangement that comprises eight neoepitopes ('minigene') with a total length of 15 amino acids in concatemeric series without intervening linker sequences, while Construct 2 shows the arrangement of Construct 1 but with inclusion of nine amino acid linkers between each neoepitope sequence. Of course, and as already noted above, it should be recognized that the exact length of the neoepitope sequence is not limited to 15 amino acids, and that the exact length may vary considerably. However, in most cases, where neoepitope sequences of between 8-12 amino acids are flanked by additional amino acids, the total length will typically not exceed 25 amino acids, or 30 amino acids, or 50 amino acids. Likewise, it should be noted that while FIG. 1 denotes G-S linkers, various other linker sequences are also suitable for use herein. Such relatively short neoepitopes are especially beneficial where presentation of the neoepitope is intended to be via the MHC-I complex.

In this context, it should be appreciated that suitable linker sequences will provide steric flexibility and separation of two adjacent neoepitopes. However, care must be taken to as to not chose amino acids for the linker that could be immunogenic/form an epitope that is already present in a patient. Consequently, it is generally preferred that the polytope construct is filtered once more for the presence of epitopes that could be found in a patient (e.g., as part of normal sequence or due to SNP or other sequence variation). Such filtering will apply the same technology and criteria as already discussed above.

Similarly, Construct 3 exemplarily illustrates a neoepitope arrangement that includes eight neoepitopes in concatemeric series without intervening linker sequences, and Construct 4 shows the arrangement of Construct 3 with inclusion of nine amino acid linkers between each neoepitope sequence. As noted above, it should be recognized that the exact length of such neoepitope sequences is not limited to 25 amino acids, and that the exact length may vary considerably. However, in most cases, where neoepitope sequences of between 14-20 amino acids are flanked by additional amino acids, the total length will typically not exceed 30 amino acids, or 45 amino acids, or 60 amino acids. Likewise, it should be noted that while FIG. 1 denotes G-S linkers for these constructs, various other linker sequences are also suitable for use herein. Such relatively long neoepitopes are especially beneficial where presentation of the neoepitope is intended to be via the MHC-II complex.

In this example, it should be appreciated that the 15-aa minigenes are MHC Class I targeted tumor mutations selected with 7 amino acids of native sequence on either side, and that the 25-aa minigenes are MHC Class II targeted tumor mutations selected with 12 amino acids of native sequence on either side. The exemplary 9 amino acid linkers are deemed to have sufficient length such that "unnatural" MHC Class I epitopes will not form between adjacent minigenes. Polytope sequences tended to be processed and presented more efficiently than single neoepitopes (data not shown), and addition of amino acids beyond 12 amino acids for MHC-I presentation and addition of amino acids beyond 20 amino acids for MHC-I presentation appeared to allow for somewhat improved protease processing.

To maximize the likelihood that customized protein sequences remain intracellular for processing and presentation by the HLA complex, neoepitope sequences may be arranged in a manner to minimize hydrophobic sequences that may direct trafficking to the cell membrane or into the extracellular space. Most preferably, hydrophobic sequence or signal peptide detection is done either by comparison of sequences to a weight matrix (see e.g., *Nucleic Acids Res.* 1986 Jun. 11; 14(11): 4683-4690) or by using neural networks trained on peptides that contain signal sequences (see e.g., *Journal of Molecular Biology* 2004, Volume 338, Issue 5, 1027-1036). FIG. 2 depicts an exemplary scheme of arrangement selection in which a plurality of polytope sequences are analyzed. Here, all positional permutations of all neoepitopes are calculated to produce a collection of arrangements. This collection is then processed through a weight matrix and/or neural network prediction to generate a score representing the likelihood of presence and/or strength of hydrophobic sequences or signal peptides. All positional permutations are then ranked by score, and the permutation(s) with a score below a predetermined threshold or lowest score for likelihood of presence and/or strength of hydrophobic sequences or signal peptides is/are used to construct a customized neoepitope expression cassette.

With respect to the total number of neoepitope sequences in a polytope it is generally preferred that the polytope comprise at least two, or at least three, or at least five, or at least eight, or at least ten neoepitope sequences. Indeed, the payload capacity of the recombinant DNA is generally contemplated the limiting factor, along with the availability of filtered and appropriate neoepitopes. Therefore, adenoviral expression vectors, and particularly Adv5 are especially preferred as such vectors can accommodate up to 14 kb in recombinant payload.

In still further contemplated aspects of the inventive subject matter, it should be noted that the neoepitopes/polytopes can be directed towards a specific sub-cellular compartment (e.g., cytosol, endosome, lysosome), and with that, towards a particular MHC presentation type. Such directed expression, processing, and presentation is particularly advantageous as contemplated compositions may be prepared that direct an immune response towards a $CD8^+$ type response (where the polytope is directed to the cytoplasmic space) or towards a $CD4^+$ type response (where the polytope is directed to the endosomal/lysosomal compartment). Moreover, it should be recognized that polytopes that would ordinarily be presented via the MHC-I pathway can be presented via the MHC-II pathway (and thereby mimick cross-presentation of neoepitopes). Therefore, it should be appreciated that neoepitope and polytope sequences may be designed and directed to one or both MHC presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmatic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane.

Moreover, it is contemplated that proteolytic degradation of the polytope can also be enhanced using various methods, and especially contemplated methods include addition of a cleavable or non-cleavable ubiquitin moiety to the N-terminus, and/or placement of one or more destabilizing amino acids (e.g., N, K, C, F, E, R, Q) to the N-terminus of the polytope where the presentation is directed towards MHC-I. On the other hand, where presentation is directed towards MHC-II, cleavage sites for particular endosomal or lysosomal proteases can be engineered into the polytope to so facilitate of promote antigen processing.

Therefore, in contemplated aspects of the inventive subject matter, signal and/or leader peptides may be used for trafficking neoepitopes and/or polytopes to the endosomal and lysosomal compartment, or for retention in the cytoplasmic space. For example, where the polytope is to be exported to the endosomal and lysosomal compartment, a leader peptide such as the CD1b leader peptide may be employed to sequester the (nascent) protein from the cytoplasm. Additionally, or alternatively, targeting presequences and/or targeting peptides can be employed. The presequences of the targeting peptide may be added to the N-terminus and/or C-terminus and typically comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus.

In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[LI] or DXXLL consensus motifs. All of these signals are recognized by components of protein coats peripherally associated with the cytosolic face of membranes. YXXØ and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., Immunology, 122, 522-531). For example, lysosomal targeting can be achieved using a LAMP1-TM (transmembrane) sequence, while recycling endosomes can be targeted via the CD1a tail targeting sequence, and sorting endosomes can be targeted via the CD1c tail targeting sequence as is shown in more detail further below.

In still further contemplated aspects, the polytope may also be designed as a chimeric polytope that includes at least a portion of, and more typically an entire tumor associated antigen (e.g., CEA, PSMA, PSA, MUC1, AFP, MAGE, HER2, HCC1, p62, p90, etc.). Most notably, tumor associated antigens are generally processed and presented via the MHC-II pathway. Therefore, instead of using compartment specific signal sequences and/or leader sequences, the processing mechanism for tumor associated antigens can be employed for MHC-II targeting.

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein such that the protein is retained in the cell facing the cytosol. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

In still further contemplated aspects of the inventive subject matter, the polytope may also comprise one or more transmembrane segments that will direct the neoepitope after processing to the outside of the cell membrane to so be visible to immune competent cells. There are numerous transmembrane domains known in the art, and all of those are deemed suitable for use herein, including those having a single alpha helix, multiple alpha helices, alpha/beta barrels, etc. For example, contemplated transmembrane domains can comprise comprises the transmembrane region(s) of the alpha, beta, or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, or PAG/Cbp. Where a fusion protein is desired, it is contemplated that the recombinant chimeric gene has a first portion that encodes the transmembrane region(s), wherein the first portion is cloned in frame with a second portion that encodes the inhibitory protein. It should be noted that such presentation will not result in MHC-complex presentation and as such provides a neoepitope presentation independent of MHC/T-cell receptor interaction, which may further open additional avenues for immune recognition and trigger antibody production against the neoepitopes.

Alternatively, or additionally, the polytope may also be designed to include signal sequences for protein export of one or more neoepitope to thereby force a transfected cell to produce and secrete one or more neoepitopes. For example, the SPARC leader sequence may be added to a neoepitope or polytope sequence, leading to in vivo secretion of the neoepitope or polytope sequence into the extracellular space. Advantageously, such secreted neoepitopes or polytopes are then taken up by immune competent cells, and especially antigen presenting cells and dendritic cells, that in turn process and display the neoepitopes, typically via MHC-II pathways.

Alternatively, or additionally, the neoepitope or polytope may also be administered as peptide, optionally bound to a carrier protein to so act as a peptide vaccine. Among other suitable carrier proteins, human albumin or lactoferrin are particularly preferred. Such carrier proteins may be in native conformation, or pretreated to form nanoparticles with exposed hydrophobic domains (see e.g., *Adv Protein Chem Struct Biol*. 2015; 98:121-43) to which the neoepitope or polytope can be coupled. Most typically, coupling of the neoepitope or polytope to the carrier protein will be non-covalent. Similar to the secreted neoepitopes or polytopes, carrier protein-bound neoepitopes or polytopes will be taken up by the immune competent cells, and especially antigen presenting cells and dendritic cells, that in turn process and display the neoepitopes, typically via MHC-II pathways.

Therefore, it should be appreciated that immune therapeutic compositions may be prepared that can deliver one or more neoepitopes to various sub-cellular locations, and with that generate distinct immune responses. For example, Prior Art FIG. 3 schematically illustrates a scenario where the polytope is predominantly processed in the proteasome of the cytoplasm and presented via the MHC-I complex, which is recognized by the T-cell receptor of a $CD8^+$ T-cell. Consequently, targeting polytope processing to the cytosolic compartment will skew the immune response towards a $CD8^+$ type response. On the other hand, Prior Art FIG. 4 schematically illustrates a scenario where the polytope is predominantly processed in the endosomal compartment and presented via the MHC-II complex, which is recognized by the T-cell receptor of a $CD4^+$ T-cell. Consequently, targeting polytope processing to the endosomal or lysosomal compartment will skew the immune response towards a $CD4^+$ type response. In addition, it should be appreciated that such targeting methods allow for specific delivery of a polytope or neoepitope peptide to an MHC subtype having the highest affinity with the peptide, even if that peptide would otherwise not be presented by that MHC subtype. Therefore, and as noted earlier, peptides for MHC-I presentation will generally be designed to have 8-12 amino acids (plus additional amino acids for flexibility in protease processing), while peptides for MHC-II presentation will be designed to have 14-20 amino acids (plus additional amino acids for flexibility in protease processing). In the examples below, further amino acids were added to allow for processing flexibility in the cytoplasmic, proteasome, or endosomal compartments.

In still further contemplated aspects of the inventive subject matter, it should be noted that trafficking modes of the neoepitope or polytope may be combined to accommodate one or more specific purposes. For example, sequential administration of the same neoepitopes or polytope with different targeting may be particularly beneficial in a prime-boost regimen where in a first administration the patient in inoculated with a recombinant virus to infect the patients cells, leading to antigen expression, processing, and presentation (e.g., predominantly MHC-I presentation) that will result in a first immune response originating from within a cell. The second administration of the same neoepitopes bound to albumin may then be employed as a boost as the so delivered protein is taken up by antigen presenting cells, leading in most cases to a distinct antigen presentation (e.g., predominantly MHC-II presentation). Where the same neoepitopes or polytope is trafficked to the cell surface for cell surface bound MHC-independent presentation, ADCC responses or NK mediated cell killing may be promoted. In still further contemplated aspects, and as illustrated in the examples below, immunogenicity of neoepitopes may be enhanced by cross presentation or MHC-II directed presentation. Notably, as cancer cell neoepitopes are typically internally generated and recycled, and with that preferentially presented via the MHC-I system, contemplated systems and methods now allow for presentation of such neoepitopes via MHC-II, which may be more immunogenic as is shown in more detail below. In addition, multiple and distinct trafficking of the same neoepitopes or polytopes may advantageously increase or supplement an immune response due to the stimulation of various and distinct components of the cellular and humoral immune system.

Of course, it should be appreciated that multiple and distinct trafficking of the same neoepitopes or polytopes may be achieved in numerous manners. For example, differently trafficked neoepitopes or polytopes may be administered separately using the same (e.g., viral expression vector) or different (e.g., viral expression vector and albumin bound) modality. Similarly, and especially where the therapeutic agent is an expression system (e.g., viral or bacterial), the recombinant nucleic acid may include two distinct portions that encode the same, albeit differently trafficked neoepitope or polytope (e.g., first portion trafficked to first location (e.g., cytosol or endosomal or lysosomal), second portion trafficked to a second, distinct location (e.g., cytosol or endosomal or lysosomal, secreted, membrane bound)). Likewise, a first administration may employ viral delivery of cytoplasm targeted neoepitopes or polytope, while a second administration is typically at least a day, two days, four days, a week, or two weeks after the first administration and may employ viral delivery of endosomal or lysosomal targeted or secreted neoepitopes or polytope.

Additionally, it is contemplated that the expression construct (e.g., recombinant viral expression vector or plasmid) may further encode at least one, more typically at least two, even more typically at least three, and most typically at least four co-stimulatory molecules to enhance the interaction between the infected cells (e.g., antigen presenting cells) and T-cells. For example, suitable co-stimulatory molecules include CD80, CD86, CD30, CD40, CD30L, CD40L, ICOS-L, B7-H3, B7-H4, CD70, OX40L, 4-1BBL, while other stimulatory molecules with less defined (or understood) mechanism of action include GITR-L, TIM-3, TIM-4, CD48, CD58, TL1A, ICAM-1, LFA3, and members of the SLAM family. However, especially preferred molecules for coordinated expression with the cancer-associated sequences include CD80 (B7-1), CD86 (B7-2), CD54 (ICAM-1) and CD11 (LFA-1). In addition to co-stimulatory molecules, the inventors also contemplate that one or more cytokines or cytokine analogs may be expressed from the recombinant nucleic acid, and especially preferred cytokines and cytokine analogs include IL-2, IL-15, and IL-a5 super-agonist (ALT-803). Moreover, it should be appreciated that expression of the co-stimulatory molecules and/or cytokines will preferably be coordinated such that the neoepitopes or polytope are expressed contemporaneously with one or more co-stimulatory molecules and/or cytokines. Thus, it is typically contemplated that the co-stimulatory molecules and/or cytokines are produced from a single transcript (which may or may not include the sequence portion encoding the polytope), for example, using an internal ribosome entry site or 2A sequence, or from multiple transcripts.

Likewise, it is contemplated that the viral vector may also include a sequence portion that encodes one or more peptide ligands that bind to a checkpoint receptor. Most typically, binding will inhibit or at least reduce signaling via the receptor, and particularly contemplated receptors include CTLA-4 (especially for $CD8^+$ cells), PD-1 (especially for $CD4^+$ cells), TIM1 receptor, 2B4, and CD160. For example, suitable peptide binders can include antibody fragments and especially scFv, but also small molecule peptide ligands (e.g., isolated via RNA display or phage panning) that specifically bind to the receptors. Once more, it should be appreciated that expression of the peptide molecules will preferably be coordinated such that the neoepitopes or polytope are expressed contemporaneously with one or more of the peptide ligands. Thus, it is typically contemplated that the peptide ligands are produced from a single transcript (which may or may not include the sequence portion encoding the polytope), for example, using an internal ribosome entry site or 2A sequence, or from multiple transcripts.

It should be appreciated that all of the above noted co-stimulatory genes and genes coding for inhibitory proteins that interfere with/down-regulate checkpoint inhibition are well known in the art, and sequence information of these genes, isoforms, and variants can be retrieved from various public resources, including sequence data bases accessible at the NCBI, EMBL, GenBank, RefSeq, etc. Moreover, while the above exemplary stimulating molecules are preferably expressed in full length form as expressed in human, modified and non-human forms are also deemed suitable so long as such forms assist in stimulating or activating T-cells. Therefore, muteins, truncated forms and chimeric forms are expressly contemplated herein.

Consequently, contemplated expression constructs will preferably include a sequence portion that encodes one or more polytopes, wherein at least one, and more typically at least two, or all of the polytopes will include a trafficking signal that will result in preferential trafficking of the polytope to at least one, and more typically at least two different sub-cellular locations. For example, the first polytope may be directed towards the cytoplasm (and may include an additional cleavable or non-cleavable ubiquitin) while the second polytope may be directed towards the endosomal or lysosomal compartment. Or the first polytope may be directed towards the endosomal or lysosomal compartment while the second polytope may be directed towards the cell membrane or be secreted. As noted before, the encoded polytope will comprise at least two neoepitopes, optionally separated by a linker. Moreover, such contemplated expression constructs will also include a sequence portion that encodes one or more co-stimulatory molecules and/or cytokines, and may also include one or more inhibitory proteins that interfere with/down-regulate checkpoint inhibition. Most typically, the expression construct will also include regulatory sequences operably coupled to the above sequence portions to drive contemporaneous expression of the polytope and the co-stimulatory molecules, cytokines, and/or inhibitory proteins. Suitable promoter elements are known in the art, and especially preferred promoters include the constitutive and inducible promoters discussed above.

Where the expression construct is a viral expression construct (e.g., an adenovirus, and especially AdV with E1 and E2b deleted), it is contemplated that the recombinant viruses may then be individually or in combination used as a therapeutic vaccine in a pharmaceutical composition, typically formulated as a sterile injectable composition with a virus titer of between $10^6$-$10^{13}$ virus particles, and more typically between $10^9$-$10^{12}$ virus particles per dosage unit. Alternatively, virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody.

Where desired, additional therapeutic modalities may be employed which may be neoepitope based (e.g., synthetic antibodies against neoepitopes as described in WO 2016/172722), alone or in combination with autologous or allogenic NK cells, and especially haNK cells or taNK cells (e.g., both commercially available from NantKwest, 9920 Jefferson Blvd. Culver City, Calif. 90232). Where haNK or taNK cells are employed, it is particularly preferred that the haNK cell carries a recombinant antibody on the CD16 variant that binds to a neoepitope of the treated patient, and where taNK cells are employed it is preferred that the chimeric antigen receptor of the taNK cell binds to a neoepitope of the treated patient. The additional treatment modality may also be independent of neoepitopes, and especially preferred modalities include cell-based therapeutics such as activated NK cells (e.g., aNK cells, commercially available from NantKwest, 9920 Jefferson Blvd. Culver City, Calif. 90232), and non cell-based therapeutics such as chemotherapy and/or radiation. In still further contemplated aspects, immune stimulatory cytokines, and especially IL-2, IL15, and IL-21 may be administered, alone or in combination with one or more checkpoint inhibitors (e.g., ipilimumab, nivolumab, etc.). Similarly, it is still further contemplated that additional pharmaceutical intervention may include administration of one or more drugs that inhibit immune suppressive cells, and especially MDSCs Tregs, and M2 macrophages. Thus, suitable drugs include IL-8 or interferon-γ inhibitors or antibodies binding IL-8 or interferon-γ, as well as drugs that deactivate MDSCs (e.g., NO inhibitors, arginase inhibitors, ROS inhibitors), that block development of or differentiation of cells to MDSCs (e.g., IL-12, VEGF-inhibitors, bisphosphonates), or agents that are toxic to MDSCs (e.g., gemcitabine, cisplatin, 5-FU). Likewise, drugs like cyclophosphamide, daclizumab, and anti-GITR or anti-OX40 antibodies may be used to inhibit Tregs.

To trigger overexpression or transcription of stress signals, it is also contemplated that the chemotherapy and/or radiation for the patient may be done using a low-dose regimen, preferably in a metronomic fashion. For example, it is generally preferred that such treatment will use doses effective to affect at least one of protein expression, cell division, and cell cycle, preferably to induce apoptosis or at least to induce or increase the expression of stress-related genes (and particularly NKG2D ligands). Thus, in further contemplated aspects, such treatment will include low dose treatment using one or more chemotherapeutic agents. Most typically, low dose treatments will be at exposures that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Additionally, where advantageous, such low-dose regimen may be performed in a metronomic manner as described, for example, in U.S. Pat. Nos. 7,758,891, 7,771,751, 7,780,984, 7,981,445, and 8,034,375.

With respect to the particular drug used in such low-dose regimen, it is contemplated that all chemotherapeutic agents are deemed suitable. Among other suitable drugs, kinase inhibitors, receptor agonists and antagonists, anti-metabolic, cytostatic and cytotoxic drugs are all contemplated herein. However, particularly preferred agents include those identified to interfere or inhibit a component of a pathway that drives growth or development of the tumor. Suitable drugs can be identified using pathway analysis on omics data as described in, for example, WO 2011/139345 and WO 2013/062505. Most notably, so achieved expression of stress-related genes in the tumor cells will result in surface presentation of NKG2D, NKP30, NKP44, and/or NKP46 ligands, which in turn activate NK cells to specifically destroy the tumor cells. Thus, it should be appreciated that low-dose chemotherapy may be employed as a trigger in tumor cells to express and display stress related proteins, which in turn will trigger NK-cell activation and/or NK-cell mediated tumor cell killing. Additionally, NK-cell mediated killing will be associated with release of intracellular tumor specific antigens, which is thought to further enhance the immune response.

Consequently, the inventors contemplate various methods of treatment of cancer in a patient in which a recombinant nucleic acid is administered to the patient (preferably in form of viral transfection in vivo) wherein the recombinant nucleic acid comprises a sequence portion that encodes one or more polytopes. Most preferably, at least one, and more typically at least two, or all of the polytopes include a trafficking signal that will result in preferential trafficking (e.g., at least 70%, more typically at least 80%, and most typically at least 90% of all expressed polytope is found in the targeted sub-cellular compartment) of the polytope to at least one, or at least two different sub-cellular locations. For example, the first polytope may be directed towards the cytoplasm (and may include an additional cleavable or non-cleavable ubiquitin) while the second polytope may be directed towards the endosomal or lysosomal compartment. Or the first polytope may be directed towards the endosomal or lysosomal compartment while the second polytope may be directed towards the cell membrane or be secreted. As discussed above, the encoded polytope will comprise at least two neoepitopes, optionally separated by a linker.

In at least some of the contemplated methods, contemplated expression constructs will also include a sequence portion that encodes one or more co-stimulatory molecules and/or cytokines, and may also include one or more inhibitory proteins that interfere with/down-regulate checkpoint inhibition. Therefore, expression of the polytope may be accompanied by expression of the co-stimulatory molecules, cytokines, and/or inhibitory proteins. Thus, the expression construct will include regulatory sequences operably coupled to the above sequence portions to drive contemporaneous expression of the polytope and the co-stimulatory molecules, cytokines, and/or inhibitory proteins.

As will be readily appreciated, the same (or different) polytopes may be targeted in contemplated methods to different sub-cellular compartments at the same time or in subsequent administrations, for example, using different expression constructs that are administered contemporaneously or temporally spaced apart. Consequently, and due to the possibility of targeting different compartments (and even extracellular space), contemplated compositions and methods may also be employed to trigger a $CD8^+$ biased immune response (stimulation of cytotoxic T cells), to trigger a $CD4^+$ biased immune response (producing Th1 and/or Th2 cytokine to stimulate B-cells, antibody production, and memory cells), an antibody biased immune response, and/or a stimulated immune response (at least partial reversal of checkpoint inhibition and/or increased activation of NK and T cell cytotoxicity). Thus, and viewed from a different perspective, where a patient has insufficient activity of NK and T cell cytotoxicity against a tumor, contemplated compositions and methods may be employed to support or increase such activity by targeting polytopes towards the cytoplasmic antigen presentation pathway to so increase MHC-I presentation and enhance a $CD8^+$ biased immune response. On the other hand, where a patient has an insufficient $CD4^+$ type immune response, contemplated compositions and methods may be employed to support or increase such activity by targeting polytopes towards the endosomal and/or lysosomal antigen presentation pathway to so increase MHC-II presentation, and with that enhance a $CD4^+$ biased immune response.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

EXAMPLES

Exemplary Sequence Arrangements

Neoepitope sequences were determined in silico by location-guided synchronous alignment of tumor and normal samples as, for example, disclosed in US 2012/0059670 and US 2012/0066001 using BAM files and BAM servers. Specifically, DNA analysis of the tumor was from the B16-F10 mouse melanoma line and matched normal was blood from C57bl/6 parental mouse DNA. The results were filtered for expression by RNA sequencing of this tumor cell line. Neoepitopes that were found expressed were further analyzed for binding affinity towards murine MHC-I (here: Kb) and MHC-II (here: I-Ab). Selected binders (with affinity of equal or less than 200 nM) were further analyzed after a further step of dbSNP filtering using positional permutations of all neoepitopes that were then processed through a weight matrix and neural network prediction to generate a score representing the likelihood of presence and/or strength of hydrophobic sequences or signal peptides. The best scoring arrangement (lowest likelihood of hydrophobic sequences or signal peptides) for the polytope (not shown) was used for further experiments. Neoepitopes were prioritized by detection in RNAseq or other quantitative system that yielded expression strength for a specific gene harboring the neoepitope mutation.

Table 1 shows exemplary neoepitopes that were expressed as determined by RNAseq along with gene name and mutated amino acid and position of the mutated amino acid. The neoepitope listed with * was discarded after dbSNP filtering as that neoepitope occurred as variant Rs71257443 in 28% of the population.

TABLE 1

| Gene | Position | Neoepitope-a | Neoepitope-b |
|---|---|---|---|
| VIPR2 | V73M | GETVTMPCP | |
| LILRB3 | T187N | VGPVNPSHR* | |
| FCRL1 | R286C | GLGAQCSEA | |
| FAT4 | S1613L | RKLTTELTI | PERRKLTTE |
| PIEZO2 | T2356M | MDWVWMDTT | VWMDTTLSL |
| SIGLEC14 | A292T | GKTLNPSQT | REGKTLNPS |
| SIGLEC1 | D1143N | VRNATSYRC | NVIVRNATS |
| SLC4A11 | Q678P | FAMAQIPSL | AQIPSLSLR |

Table 2 shows further examples of neoepitopes in which the position of the mutated amino acid was changed, and shows further alternate sequences for MHC-I presentation (9-mer) and MHC-II presentation (15-mer). The neoepitope sequence for MHC-II presentation was back-translated to the corresponding nucleic acid sequence, which is also shown in Table 2.

mutant epitopes were identified in the B16F10 melanoma cell line. Candidate neoepitopes were further filtered as described above using sequencing data analysis and binding analysis to murine MHC I (H2-Kb, H2-Dd) and MHC II (I-Ab). Nine distinct polytope constructs were then prepared for testing various trafficking schemes, and each construct was prepared as the corresponding recombinant nucleic acid under the control of a CMV promoter. Each construct was cloned into an AdV5 expression vector that had deleted E1 and E2b genes, and the resulting recombinant virus was then used for transfection of mice as is further discussed below.

More specifically, three polytope constructs included MHC I binding neoepitopes for MHC-I presentation and were therefore targeted to the cytoplasmic compartment. While one construct had an unmodified N-terminus, another construct had an N-terminal non-cleavable ubiquitin, and yet another construct had an N-terminal cleavable ubiquitin. Ubiquitination was used to target the proteasome in the cytosol. Three further polytope constructs included MHC I binding neoepitopes for MHC-II presentation and were therefore targeted to the lysosomal/endosomal compartments compartment. While one construct had lysosomal targeting sequence, another construct had a recycling endosomal targeting sequence, and yet another construct had a sorting endosomal targeting sequence. Three additional polytope constructs included MHC II binding neoepitopes for MHC-II presentation and were also targeted to the lysosomal/endosomal compartments compartment. Once more, one construct had lysosomal targeting sequence,

TABLE 2

| Gene | Change | Neoepitope-a | Neoepitope-b | Extended 15 mer | Nucleotide Sequence |
|---|---|---|---|---|---|
| SLC4A11 | Q678P | FAMAQIPSL | AQIPSLSLR | PFAMAQIPSLSLRAV | CCCTTCGCCATGGCCC AGATCCCCAGCCTGA GCCTGAGGGCCGTG |
| SIGLEC1 | D1143N | VRNATSYRC | NVTVRNATS | LPNVTVRNATSYRCG | CTGCCCAACGTGACC GTGAGGAACGCCACC AGCTACAGGTGCGGC |
| SIGLEC14 | A292T | GKTLNPSQT | REGKTLNPS | SWFREGKTLNPSQTS | AGCTGGTTCAGGGAG GGCAAGACCCTGAAC CCCAGCCAGACCAGC |
| PIEZO2 | T2356M | MDWVWMDTT | VWMDTTLSL | AVMDWVWMDTTLSLS | GCCGTGGATGGACTGG GTGTGGATGGACACC ACCCTGAGCCTGAGC |
| FAT4 | S1613L | RKLTTELTI | PERRKLTTE | LGPERRKLTTELTII | CTGGGCCCCGAGAGG AGGAAGCTGACCACC GAGCTGACCATCATC |
| FCRL1 | R286C | GLGAQCSEA | | NNGLGAQCSEAVTLN | AACAACGGCCTGGGC GCCCAGTGCAGCGAG GCCGTGACCCTGAAC |
| VIPR2 | V73M | GETVTMPCP | | NVGETVTMPCPKVFS | AACGTGGGCGAGACC GTGACCATGCCCTGC CCCAAGGTGTTCAGC |
| FLRT2 | R346W | EQVWGMAVR | | CQGPEQVWGMAVREL | TGCCAGGGCCCCGAG CAGGTGTGGGGCATG GCCGTGAGGGAGCT G |

Sequence Trafficking

Model cancer: Murine B16-F10 melanoma (derived from C57/B16 mouse) was used tumors were screened in a tumor versus normal manner as described above, and expressed another construct had a recycling endosomal targeting sequence, and yet another construct had a sorting endosomal targeting sequence. These nine constructs had sequence arrangements as follows.

In the following exemplary sequences, for MHC-I presentation, ubiquitin (cleavable and non-cleavable) were used for proteasome targeting, while the CD1b leader peptide was used as an export leader peptide for trafficking the polypeptide out of the cytosol for all MHC-II directed sequences. LAMP1-TM/cytoplasmic tail was used as a lysosomal targeting sequence, while LAMP1-TM/CD1a tail was used as a recycling endosomes targeting sequence, and LAMP1-TM/CD1c tail was used as a sorting endosomes targeting domain.

It should further be noted that various internal controls were also used in the above polypeptides to account for expression and presentation. More specifically, the SIINFEKL peptide was used as an internal control for a MHC I restricted (Kb) peptide epitope, while the Esat6 peptide was used as an internal control for a secreted protein for MHC II presentation. FLAG-tag was used as an internal control epitope for detection of expression, and cMYC used as an internal control Tag for simple protein detection.

Exemplary Constructs for MHC-I Epitopes Directed to MHC-I Presentation (Traffic Through Proteasome, Cytoplasmic Targeting):

Polyepitope only: 12aa-A$^{m}$-12aa-AAAA-12aa-B$^{m}$-12aa-AAAA-(12aa-X$^{m}$-12aa-AAAA)$_n$-SIINFEKL-AAAA-Esat6-cMYC. FIG. 5A exemplarily depicts the polypeptide structure of such arrangement where the SIINFEKL motif is underlined, the Esat6 motif is in italics, and where the cMY motif is in bold type font. The nucleotide sequence for FIG. 5A is SEQ ID NO: 9, and the polypeptide sequence for FIG. 5A is SEQ ID NO: 12.

Polyepitope and cleavable ubiquitin GGR N-terminus: Ubiquitin-GGR-12aa-A$^{m}$-12aa-AAAA-12aa-B$^{m}$-12aa-AAAA-(12aa-X$^{m}$-12aa-AAAA)$_n$-SIINFEKL-AAAA-Esat6-cMYC. FIG. 5B exemplarily depicts the polypeptide structure of such arrangement where the cleavable ubiquitin moiety is italics and underlined, the SIINFEKL motif is underlined, the Esat6 motif is in italics, and where the cMY motif is in bold type font. The nucleotide sequence for FIG. 5B is SEQ ID NO: 10, and the polypeptide sequence for FIG. 5B is SEQ ID NO: 13.

Polyepitope and non-cleavable ubiquitin G N-terminus: Ubiquitin-G-12aa-A$^{m}$-12aa-AAAA-12aa-B$^{m}$-12aa-AAAA-(12aa-X$^{m}$-12aa-AAAA)$_n$-SIINFEKL-AAAA-Esat6-cMYC. FIG. 5C exemplarily depicts the polypeptide structure of such arrangement where the cleavable ubiquitin moiety is italics and underlined, the SIINFEKL motif is underlined, the Esat6 motif is in italics, and where the cMY motif is in bold type font. The nucleotide sequence for FIG. 5C is SEQ ID NO: 11, and the polypeptide sequence for FIG. 5C is SEQ ID NO: 14.

Exemplary Constructs for MHC-I Epitopes Directed to MHC-II Presentation (Export from Cytoplasm, Traffic Through Endo/Lysosome):

Lysosomal targeting of Kb epitope peptides: (CD1b leader peptide)-20aa-A$^{m}$-20aa-GPGPG-20aa B$^{m}$-20aa-GPGPG-(20aa-X$^{m}$-20aa-GPGPG-)$_n$-Esat6-FlagTag-LAMP1TM/cytoplasmic tail. FIG. 6A exemplarily depicts the polypeptide structure of such arrangement where the CD1b leader peptide moiety is bold, the Esat6 motif is in underlined, the Flag-tag motif is italics, and where the LAMP1TM/cytoplasmic tail is in bold/underline type font. The nucleotide sequence for FIG. 6A is SEQ ID NO: 15, and the polypeptide sequence for FIG. 6A is SEQ ID NO: 18.

Recycling lysosome targeting of Kb epitope peptides: (CD1b leader peptide)-20aa-A$^{m}$-20aa-GPGPG-20aa B$^{m}$-20aa-GPGPG-(20aa-X$^{m}$-20aa-GPGPG-)$_n$-Esat6-FlagTag-LAMP1TM/CD1a tail. FIG. 6B exemplarily depicts the polypeptide structure of such arrangement where the CD1b leader peptide moiety is bold, the Esat6 motif is in underlined, the Flag-tag motif is italics, and where the LAMP1TM motif is in bold/underline type font, and the CD1a targeting motif is underline/italics. The nucleotide sequence for FIG. 6B is SEQ ID NO: 16, and the polypeptide sequence for FIG. 6B is SEQ ID NO: 19.

Sorting endosome targeting of Kb epitope peptides: (CD1b leader peptide)-20aa-A$^{m}$-20aa-GPGPG-20aa B$^{m}$-20aa-GPGPG-(20aa-X$^{m}$-20aa-GPGPG-)$_n$-Esat6-FlagTag-LAMP1TM/CD1c tail. FIG. 6C exemplarily depicts the polypeptide structure of such arrangement where the CD1b leader peptide moiety is bold, the Esat6 motif is in underlined, the Flag-tag motif is italics, and where the LAMP1TM motif is in bold/underline type font, and the CD1c targeting motif is underline/italics. The nucleotide sequence for FIG. 6C is SEQ ID NO: 17, and the polypeptide sequence for FIG. 6C is SEQ ID NO: 20.

Exemplary Constructs for MHC-II Epitopes Directed to MHC-II Presentation (Export from Cytoplasm, Traffic Through Endo/Lysosome):

Lysosomal targeting of IAb epitope peptides: (CD1b leader peptide)-20aa-A$^{m}$-20aa-GPGPG-20aa B$^{m}$-20aa-GPGPG-(20aa-X$^{m}$-20aa-GPGPG-)$_n$-Esat6-FlagTag-LAMP1TM/cytoplasmic tail. FIG. 7A exemplarily depicts the polypeptide structure of such arrangement where the CD1b leader peptide moiety is bold, the SIINFEKL and Esat6 motifs are underlined, the Flag-tag motif is italics, and where the LAMP1TM/cytoplasmic tail is in bold/underline type font. The nucleotide sequence for FIG. 7A is SEQ ID NO: 21, and the polypeptide sequence for FIG. 7A is SEQ ID NO: 24.

Recycling lysosome targeting of IAb epitope peptides: (CD1b leader peptide)-20aa-A$^{m}$-20aa-GPGPG-20aa B$^{m}$-20aa-GPGPG-(20aa-X$^{m}$-20aa-GPGPG-)$_n$-Esat6-FlagTag-LAMP1TM/CD1a tail. FIG. 7B exemplarily depicts the polypeptide structure of such arrangement where the CD1b leader peptide moiety is bold, the SIINFEKL and Esat6 motifs are underlined, the Flag-tag motif is italics, where the LAMP1TM motif is in bold/underline type font, and where the CD1a tail is in bold/italics. The nucleotide sequence for FIG. 7B is SEQ ID NO: 22, and the polypeptide sequence for FIG. 7B is SEQ ID NO: 25.

Sorting endosome targeting of IAb epitope peptides: (CD1b leader peptide)-20aa-A$^{m}$-20aa-GPGPG-20aa B$^{m}$-20aa-GPGPG-(20aa-X$^{m}$-20aa-GPGPG-)$_n$-Esat6-FlagTag-LAMP1TM/CD1c tail. FIG. 7C exemplarily depicts the polypeptide structure of such arrangement where the CD1b leader peptide moiety is bold, the SIINFEKL and Esat6 motifs are underlined, the Flag-tag motif is italics, where the LAMP1TM motif is in bold/underline type font, and where the CD1c tail is in bold/italics. The nucleotide sequence for FIG. 7C is SEQ ID NO: 23, and the polypeptide sequence for FIG. 7C is SEQ ID NO: 26.

In Vivo Vaccination

FIG. 8 depicts an exemplary in vivo vaccination experiment where nine groups of C57bl/6 mice were immunized with nine distinct recombinant Ad5 viruses comprising the sequence arrangements substantially as described above Immunization followed a biweekly schedule of administration with distinct routes for separate groups of animals (subcutaneous and intravenous) as is schematically shown in FIG. 8. Tumor challenge with B16-F10 melanoma cells was at day 42, followed by administration of an M2 macrophage suppressive drug (RP 182) and IL-15 superagonist (Alt-803). FIGS. 9A-9C depict exemplary results for subcutaneous administration, while FIGS. 10A-10C depict exemplary results for intravenous administration.

Figure 9A:
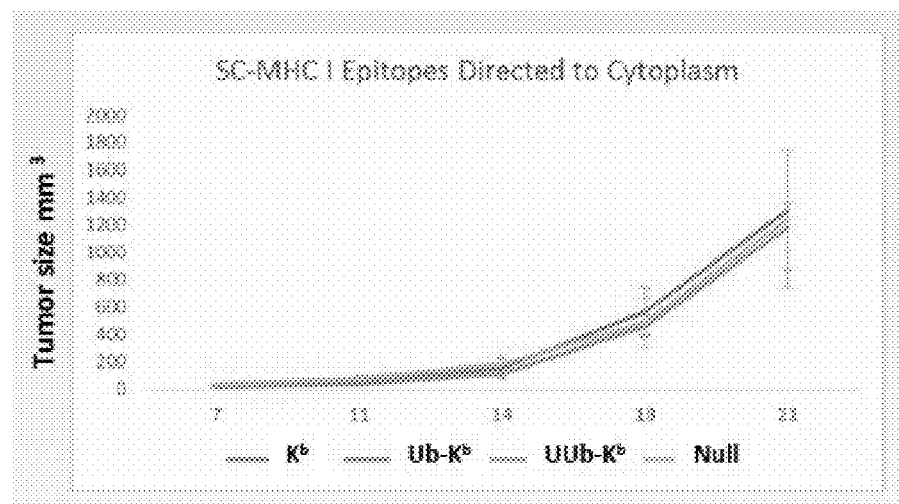
FIGS. 9A-9C are graphs depicting exemplary results for the anti-tumor vaccination using subcutaneous injection of the vaccine.
Figure 9B:
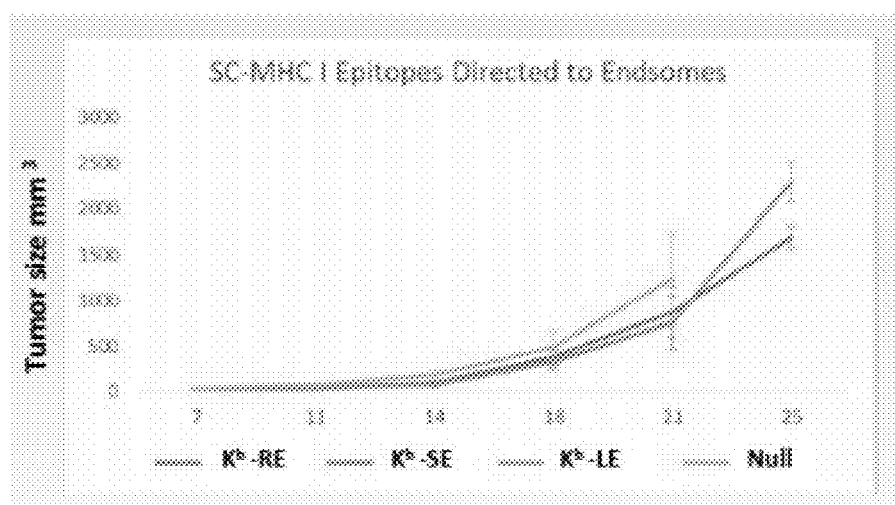
Figure 9C:
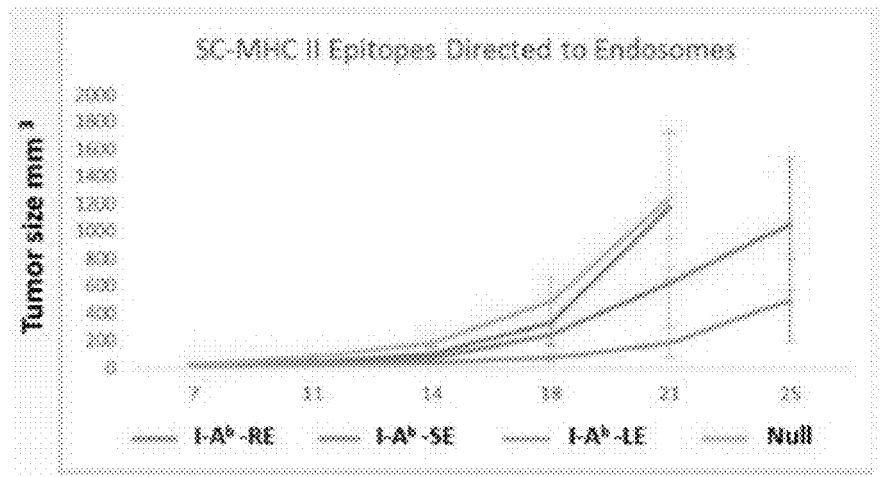

Notably, subcutaneous injection of adenovirus encoding Class I polytopes directed to the cytoplasm and MHC-I presentation did not provide a significant immune protection, regardless of the presence or absence of ubiquitination as can be taken from FIG. 9A. On the other hand, where the Class I polytopes were directed to the endosomal and lysosomal compartments for processing and presentation via MHC-II, some protective immunity was observed for direction to the recycling endosomal compartment and lysosomal compartment as is evident from FIG. 9B. Even stronger immune protection was observed when Class II polytopes were directed to the endosomal and lysosomal compartments for processing and presentation via MHC-II. Here, the strongest protection was observed for lysosomal and sorting endosomal compartments as is shown in FIG. 9C.

Figure 10A:
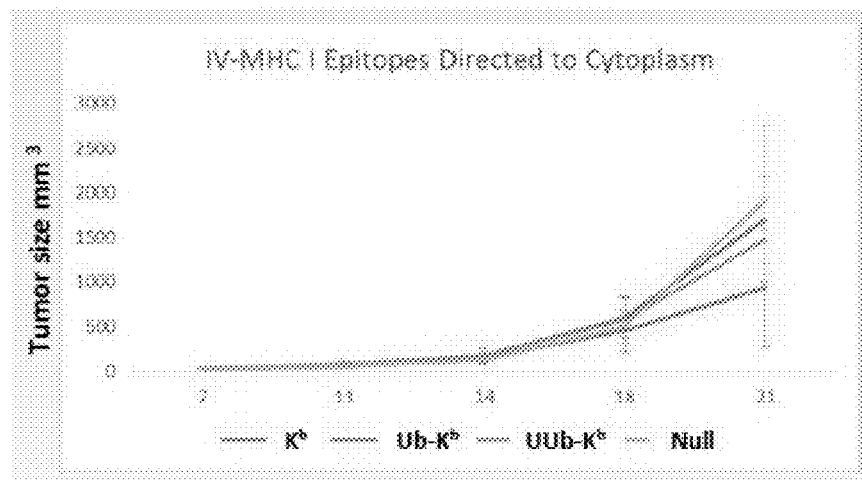
FIGS. 10A-10C are graphs depicting exemplary results for the anti-tumor vaccination using intravenous injection of the vaccine.
Figure 10B:
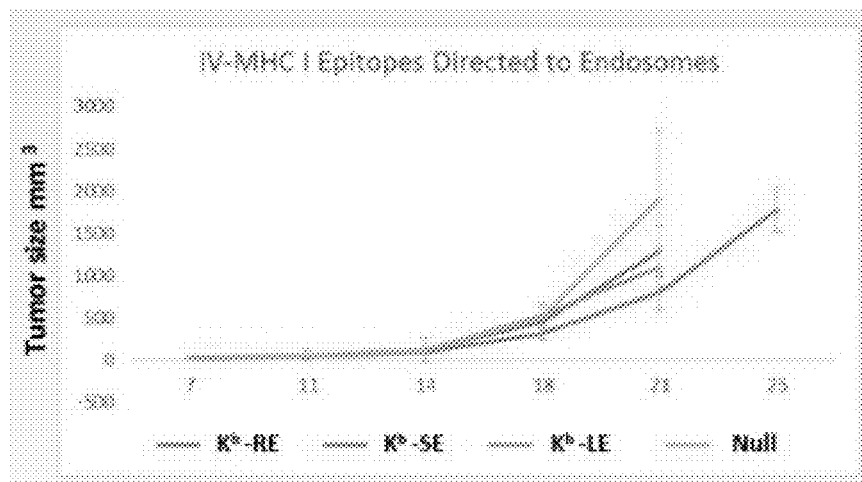
Figure 10C:
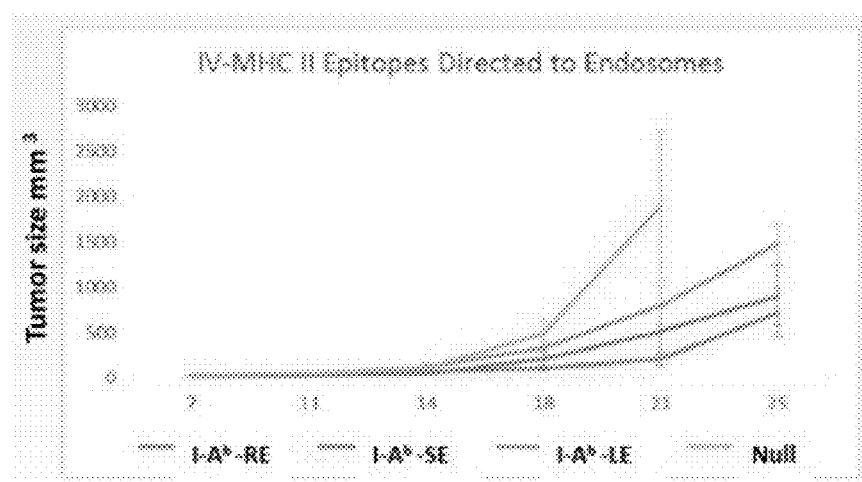

When immunization was performed with the same viral constructs, albeit via intravenous injection, protective effect of neoepitope vaccination was observed for Class I neoepitopes directed to the cytoplasm where the polytope included cleavable ubiquitin, and some protective effect was observed where the polytope included non-cleavable ubiquitin as can be seen from FIG. 10A. Notably, when the Class I polytopes were directed to the endosomal and lysosomal compartment, stronger protective effect was observed in all vaccinations as is shown in FIG. 10B. Moreover, strong protective effect was observed when Class II polytopes were directed to the endosomal and lysosomal compartments for processing and presentation via MHC-II. Here, the strongest protection was observed for recycling and sorting endosomal compartments as is shown in the graph of FIG. 10C.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of eliciting an immune response against a tumor in a subject, the method comprising:
   determining a common sequence location within first and second sequence datasets, wherein the first sequence dataset comprises sequence data from a tumor in the subject, and wherein the second sequence dataset comprises sequence data from a matched normal tissue in the subject;
   generating at least one pair of sequence pileups from the first and second sequence datasets that overlap at the common sequence location;
   determining genotypes for healthy tissue and suspected diseased tissue at the common sequence location as a function of the at least one pair of sequence pileups;
   identifying a sequence difference at the common sequence location and between genotypes;
   filtering out false positives based on reads in the at least one pair of sequence pileups to thus generate at least one patient specific neoepitope;
   immunizing the subject in need thereof with IL-15, RP-182, and a recombinant adenovirus;
   wherein the recombinant adenovirus comprises a nucleic acid sequence encoding the at least one patient specific neoepitopes operably linked to a trafficking element that directs the nucleic acid sequence to a sub-cellular location selected from the group consisting of recycling endosome, sorting endosome, and lysosome.

2. The method of claim 1, wherein the at least one patient specific neoepitope is filtered for MHC binding of less than or equal to 200 nM.

3. The method of claim 1, wherein the recombinant nucleic acid further comprises a sequence of at least one additional neoepitope, wherein the additional neoepitope is operably linked to a trafficking element that directs the additional neoepitope to a different sub-cellular location than the at least one patient specific neoepitope.

4. The method of claim 1, wherein the recombinant adenovirus further comprises a sequence encoding a protein selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, LFA3, IL-2, IL-12, IL-15, IL-15 super agonist (ALT803), IL-21, IPS1, LMP1, an anti-CTLA-4 antibody, an anti-PD-1 antibody, an anti-TIM1 receptor antibody, an anti-2B4 antibody, and an anti-CD160 antibody.

\* \* \* \* \*